United States Patent
Grenning et al.

(10) Patent No.: US 11,008,283 B2
(45) Date of Patent: *May 18, 2021

(54) METHODS AND COMPOSITIONS FOR TERPENOID TRICYCLOALKANE SYNTHESIS

(71) Applicant: University of Florida Research Foundation, Inc., Gainesville, FL (US)

(72) Inventors: Alexander James Grenning, Gainesville, FL (US); Sarah Scott, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,902

(22) Filed: Sep. 8, 2020

(65) Prior Publication Data

US 2020/0399206 A1 Dec. 24, 2020

Related U.S. Application Data

(63) Continuation of application No. 16/567,643, filed on Sep. 11, 2019, now Pat. No. 10,894,763, which is a continuation of application No. 16/383,425, filed on Apr. 12, 2019, now Pat. No. 10,487,047, which is a continuation of application No. 15/981,833, filed on May 16, 2018, now Pat. No. 10,287,239.

(51) Int. Cl.
| | |
|---|---|
| *C07C 255/31* | (2006.01) |
| *C07C 253/30* | (2006.01) |
| *C07D 227/04* | (2006.01) |
| *C07C 255/47* | (2006.01) |

(52) U.S. Cl.
CPC .......... *C07C 253/30* (2013.01); *C07C 255/31* (2013.01); *C07C 255/47* (2013.01); *C07D 227/04* (2013.01); *C07C 2603/30* (2017.05); *C07C 2603/78* (2017.05)

(58) Field of Classification Search
CPC .................................................. C07C 255/31
See application file for complete search history.

(56) References Cited

U.S. PATENT DOCUMENTS

| | | |
|---|---|---|
| 8,314,246 B2 | 11/2012 | Jamison et al. |
| 8,865,930 B2 | 10/2014 | Noel et al. |
| 8,946,472 B2 | 2/2015 | Berti et al. |
| 9,394,174 B2 | 7/2016 | Plata et al. |
| 2005/0250963 A1 | 11/2005 | Figueras et al. |
| 2017/0044282 A1 | 2/2017 | Howdle et al. |

FOREIGN PATENT DOCUMENTS

| | | |
|---|---|---|
| WO | 2010019489 A2 | 2/2010 |
| WO | 2015162419 A1 | 10/2015 |

OTHER PUBLICATIONS

Brown et al. Aust. J. Chem. 1977, 30, 1747-1755 (Year: 1977).
Scott et al., An Enyne Cope Rearrangement Enables Polycycloalkane Synthesis from Abundant Starting Materials by a Simple Strategy 2017.
Lahtigui et al., Assembly of Terpenoid Cores by a Simple, Tunable Strategy, Angew. Chem. 2016, 128, 16024-16028.
Alcaide et al., The Allenic Pauson-Khand Reaction in Synthesis, Eur. J. Org. Chem. 2004, 33773383.
Mukai et al., Rh(I)-Catalyzed Intramolecular Allenic Pauson-Khand Reaction: Construction of a Bicyclo[5.3.0]dec-1,7-dien-9-one Skeleton, Org. Lett., vol. 4, No. 10, 1755-1758, 2002.
Ghantous et al., What made sesquiterpene lactones reach cancer clinical trials? Drug Discov. Today 2010, 15, 668.
Ganem et al., Paclitaxel from Primary Taxanes: A Perspective on Creative Invention in Organozirconium Chemistry, J. Org. Chem. 2007, 72 , 3981.
Jansen et al., Synthesis of medicinally relevant terpenes: reducing the cost and time of drug discoveryFuture Med. Chem. 2014, 6, 1127.
Urabe et al., Convergent Strategies in Total Syntheses of Complex Terpenoids, M. Chem. Rev. 2015, 115, 9207.
Maimone et al., Modern synthetic efforts toward biologically active terpenes P. S. Nat Chem Biol 2007, 3 (7), 396.
Miller et al., Total Synthesis of (-)-Heptemerone B and (-)-Guanacastepene E, J. Am. Chem. Soc. 2006, 128, 17057.
McLeod, M. C., et al., Probing chemical space with alkaloid-inspired libraries, Nat. Chem. 2014, 6, 133-140.
Navaratne et al., Deconjugative alkylation/Heck reaction as a simple platform for dihydronaphthalene synthesis, Org. Biomol. Chem. 2017, 15, 69.
Ning et al., Ion-Pair-Catalyzed Sodium Borohydride Reduction in Aprotic Organic Solvents. Asian Journal of Organic Chemistry 2015, 4 (4), 333-336.
Pacheco, et al., Electrophilic Fluorodesilylation of Allenylmethylsilanes: A Novel Entry to 2-Fluoro-1,3-dienes, Org. Lett. 2005, 7(7), 1267.
Pascual-ahuir et al., GEPOL: An Improved Description of Molecular Surfaces. III. A New Algorithm for the Computation of a Solvent-Excluding Surface. J. Comput. Chem. 1994, 15, 1127-1138.
Peng et al., Stereoselective Total Syntheses of Guanacastepenes N and O, Org. Lett. 2015, 17, 3486.
Pettit et al., Antineoplastic agents. 46. The isolation and structure of dolatriol, J. Am. Chem. Soc. 1976, 98, 4677.

(Continued)

*Primary Examiner* — Matthew P Coughlin
(74) *Attorney, Agent, or Firm* — Thomas Horstemeyer, LLP

(57) ABSTRACT

In one aspect, the disclosure relates to methods for preparation of intermediates useful for the preparation of terpenoid cores. In a further aspect, the disclosed methods pertain to the preparation of compounds comprising a terpenoid core or scaffold, such as 6/7/5 tricycloalkanes. The disclosed methods utilize abundant starting materials and simple reaction sequences that can be used to tunably and scalably assemble common terpenoid cores. In various aspects, the present disclosure pertains to compounds prepared using the disclosed methods. This abstract is intended as a scanning tool for purposes of searching in the particular art and is not intended to be limiting of the present disclosure.

19 Claims, 7 Drawing Sheets

(56) References Cited

OTHER PUBLICATIONS

Rao et al., Diterpenes from the brown alga Dictyota divaricata of the indian ocean, Phytochemistry 1991, 30, 1971.
Rudi et al., Chelodane, Barekoxide, and Zaatirin—Three New Diterpenoids from the Marine Sponge Chelonaplysilla arecta, J. Nat. Prod. 1992, 55, 1408.
Rudroff, et al. Modern Developments in Biotransformations, Tetrahedron 2016, 72(46), 7212.
Shipe et al., Convergent, Enantioselective Syntheses of Guanacastepenes A and E Featuring a Selective Cyclobutane Fragmentation, J. Am. Chem. Soc. 2006, 128, 7025.
Spa-dari et al., Aphidicolin: a specific inhibitor of nuclear DNA replication in eukaryotes, Trends Biochem. Sci. 1982, 7, 29.
Stanek et al., Organocatalytic α-Allylation of α-Branched Aldehydes by Synergistic Catalysis of Brønsted Acids and Amines. Eur. J. Org. Chem. 2016, 2016 (28), 4768-4772.
Tejedor et al., Propargyl Claisen rearrangement: allene synthesis and beyond, Chem. Soc. Rev. 2013, 42, 458.
Tremblay et al., Characterization of an abeo-Taxane: Brevifoliol and Derivatives, J. Nat. Prod. 2004, 67, 838.
Rattanachaikunsoponet al., Contents and antibacterial activity of flavonoids extracted from leaves of Psidium guajava, J. Med. Plants Res. 2010, 4, 2379.
Vertesaljai et al., Knoevenagel Adducts as Trimethylenemethane Dipole Surrogates, Angew. Chem. Int. Ed. 2016, 55, 317.
Vertesaljai et al., Complex Hydroindoles by an Intramolecular Nitrile-Intercepted Allylic Alkylation Cascade Reaction, Org. Lett., 2018, 20, 1970-1973.
Volcho et al., Competing Michael and Knoevenagel reactions of terpenoids with malononitrile on basic Cs-beta zeolite. J. Mol. Catal. A: Chem. 2003, 195 (1), 263-274.
Vyas, et al., Copper(I)-Catalyzed Regioselective Propargylic Substitution Involving Si—B Bond Activation, M. Org. Lett. 2011, 13 (16), 4462.
Wang, G., et al., Terpenoids As Therapeutic Drugs and Pharmaceutical Agents, In Nat. Prod.; Humana Press Inc., 2005; pp. 197-227.
Wang et al., An Organocatalytic Asymmetric Allylic Alkylation Allows Enantioselective Total Synthesis of Hydroxymetasequirin-A and Metasequirin-B Tetramethyl Ether Diacetates. Org. Lett. 2014, 16 (3), 976-979.
Wei et al., Caribenols A and B, Sea Whip Derived Norditerpenes with Novel Tricarbocyclic Skeletons, J. Org. Chem. 2007, 72, 7386.
Wen et al., A Redox Economical Synthesis of Bioactive 6,12-Guaianolides, Org. Lett. 2013, 15, 2644.
Zhang et al., A deconjugative alkylation/Diels-Alder cycloaddition strategy to synthesize 2-substituted bicyclic scaffolds, In press. Tetrahedron vol. 73, Issue 29, Jul. 20, 2017, pp. 4076-4083 DOI: 10.1016/j.tet.2016.11.055.
Zhao et al., The M06 Suite of Density Functionals for Main Group Thermochemistry, Thermochemical Kinetics, Noncovalent Interactions, Excited States, and Transition Elements: Two New Functionals and Systematic Testing of Four M06-Class Functionals and 12 Other Function. Theor. Chem. Am. 2008, 120, 215-241.
Zhao et al., Rapid and efficient Knoevenagel condensation catalyzed by a novel protic ionic liquid under ultrasonic irradiation, Royal Society of Chemistry, vol. 3, pg. 11691-11696, 2013.
Zhuang et al., Chiral Bronsted acid catalyzed enantioselective intermolecular allylic aminations. Organic & Biomolecular Chemistry 2014, 12 (26), 4590-4593.
Yuan et al., PdCl2-catalyzed efficient allylation and benzylation of heteroarenes under ligand, base/acid, and additive-free conditions, Chem. Commun. 2011, 47, 5289-5291.
Almarasson, et al., Crystal engineering of the composition of pharmaceutical phases. Do pharmaceutical co-crystals represent a new path to improved medicines?, The Royal Society of Chemistry, 1889-1896, 2004.
Aubert et al., Transition Metal Catalyzed Cycloisomerizations of 1,n-Allenynes and -Allenenes, Chem. Rev. 2011, 111, 1954-1993.

Balthaser, B. R., et al., Remodeling of the Natural Product Fumagillol Employing a Reaction Discovery Approach, Nat Chem., 3(12): 969-973, 2011.
Black et al., 1256. Allenes. Part X. The Claisen—Cope rearrangement of propargyl vinyl systems, J. Chem. Soc. 1965, 6784-6788.
Black et al., Alkynes, Allenes, and Alkenes in [3,3]-Sigmatropy: Functional Diversity and Kinetic Monotony. A Theoretical Analysis, J. Am. Chem. Soc. 1998, 120 , 5622-5627.
Brummond et al., A General Synthetic Route to Differentially Functionalized Angularly and Linearly Fused [6-7-5] Ring Systems: A Rh(I)-Catalyzed Cyclocarbonylation Reaction, J. Org. Chem. 2008, 73, 5064.
Bubnov et al., Allylzine Bromide: Reductive Trans-L,3-Diallylation of Isoquinoline and Intramolecular Cyclization of 2,4-Dizinc Derivative, Russian Chemical Bulletin vol. 46 (11), 1975-1977, 1997.
Chan et al., Bi(OTf)3 catalyzed disproportionation reaction of cinnamyl alcohols. Tetrahedron 2017, 73 (24), 3368-3376.
Che et al., Construction of All-Carbon Quaternary Center by R2AlCl-Mediated Ring-Opening Reaction of Oxacycles, Org. Lett. 2010, 12, 488-491.
Cordier et al., Natural products as an inspiration in the diversity-oriented synthesis of bioactive compound libraries, Nat. Prod. Rep. 2008, 25, 719-737.
Craig, II et al., Enantioselective, convergent synthesis of the ineleganolide core by a tandem annulation cascade, Chem. Sci. 2017, 8, 507.
Cueto et al., Aspergilloxide, a Novel Sesterterpene Epoxide from a Marine-Derived Fungus of the Genus *Aspergillus*, Org. Lett. 2002, 4, 1583.
Duh et al., A novel cytotoxic norditerpenoid from the Formosan soft coral Sinularia inelegans, Tetrahedron Lett. 1999, 40, 6033.
Fereyduni et al., Factors Governing and Application of the Cope Rearrangement of 3,3-Dicyano-1,5-dienes and Related Studies. Org. Lett. 2017, 19 (15), 4130-4133.
Fischer, et al., Indium-Mediated Allenylation of Aldehydes and Its Application in Carbohydrate Chemistry: Efficient Synthesis of D-Ribulose and 1-Deoxy-D-ribulose, Eur. J. Org. Chem. 2011, 2011 (9), 1645.
Fulmer, et al. NMR Chemical Shifts of Trace Impurities: Common Laboratory Solvents, Organics, and Gases in Deuterated Solvents Relevant to the Organometallic Chemist, Organometallics 2010, 29, 2176.
Gampe et al., Total Syntheses of Guanacastepenes N and O**, Angew. Chem. Int. Ed. 2011, 50, 2962.
Grenning, Synlett, Simplifying Complex Scaffold Synthesis: Knoevenagel Adduct Allyl Anions as Easily Generated Multifunctional Reagents, 2017, 28, 633.
Vertesalijai et al., Knoevenagel Adducts as Trimethylenemethane Dipole Surrogates, Angewandte Chemie International Edition; vol. 55(1), p. 317-320, 2016.
Ghorai et al., A Route to Highly Functionalized β-Enaminoesters via a Domino Ring-Opening Cyclization/Decarboxylative Tautomerization Sequence of Donor-Acceptor Cyclopropanes with Substituted Malononitriles. Org. Lett. 2014, 16 (8), 2204-2207.
Grimme et al., A Consistent and Accurate ab Initio Parametrization of Density Functional Dispersion Correction (DFT-D) for the 94 Elements H-Pu. J. Chem. Phys. 2010, 132, 154104.
Grimme et al., Effect of the Damping Function in Dispersion Corrected Density Functional Theory. J. Comput. Chem., 32, 1456-1465, 2011.
Grossman et al., Selective Monoalkylation of Diethyl Malonate, Ethyl Cyanoacetate, and Malononitrile Using a Masking Group for the Second Acidic Hydrogen, J. Org. Chem. 1997, 62, 5235.
Gunduz et al., Clinical review of grayanotoxin/mad honey poisoning past and present, Clin. Toxicol. 2008, 46, 437.
Hayamizu et al., Diastereoselective Protonation on Radical Anions of Electron-Deficient Alkenes via Photoinduced Electron Transfer. The Journal of Organic Chemistry 2004, 69 (15), 4997-5004.
Hirose et al., Total Synthesis of (+)-Achalensolide Based on the Rh(I)-Catalyzed Allenic Pauson-Khand-Type Reaction, Org. Chem. 2008, 73, 1061.
Huang, M., et al., Terpenoids: natural products for cancer therapy, Expert Opin. Investig. Drugs 2012, 21, 1801.

(56) References Cited

OTHER PUBLICATIONS

Huigens III et al., A Ring Distortion Strategy to Construct Stereochemically Complex and Structurally Diverse Compounds from Natural Products Nat. Chem. 2013, 5, 195-202.

Huntsman et al., The Thermal Rearrangement of 1-Alken-5-yncs and 1,2,5-Alkatrienes1, J. Am. Chem. Soc. 1966, 88, 5846.

Iimura et al., Enantioselective Total Synthesis of Guanacastepene N Using an Uncommon 7-Endo Fleck Cyclization as a Pivotal Step, J. Am. Chem. Soc. 2006, 128, 13095.

Ilardi et al., [3,3]-Sigmatropic rearrangements: recent applications in the total synthesis of natural products, Chem. Soc. Rev. 2009, 38, 3133-3148.

Inokuchi et al., E- or Z-Selective Knoevenagel Condensation of Acetoacetic Derivatives: Effect of Acylated Substituent, that is, TEMPO and Amines, as an Auxiliary, and New Accesses to Trisubstituted E- and Z-2-Alkenals and Furans, Journal of Organic Chemistry, vol. 71, p. 947-953, 2006.

Jørgensen et al., 14-Step Synthesis of (+)-Ingenol from (+)-3-Carene, Science 2013, 341, 878.

Juvale et al., Investigation of chalcones and benzochalcones as inhibitors of breast cancer resistance protein. Biorg. Med. Chem. 2012, 20 (1), 346-355.

Kappe et al., Synthetic applications of furan Diels-Alder chemistry Tetrahedron 1997, 53, 14179.

Kazi et al., CBr4 as a Halogen Bond Donor Catalyst for the Selective Activation of Benzaldehydes to Synthesize α,β-Unsaturated Ketones. Org. Lett. 2017, 19 (5), 1244-1247.

Kolesnikov et al., Atom- and Step-Economical Preparation of Reduced Knoevenagel Adducts Using CO as a Deoxygenative Agent, Organic Letters, vol. 16(19), p. 5068-5071, 2014.

Lahtigui et al., Assembly of Terpenoid Cores by a Simple, Tunable Strategy, Angew. Chem. Int. Ed. 2016, 55 (51), 15792.

Le et al., Bifunctional Ligand Promoted Pd-Catalyzed Asymmetric Allylic Etherification/Amination, Acta Chimica Sinica 2013, 71, 1239-1242.

Li et al., Selective Mono- and Di-Allylation and Allenylation of Chlorosilanes Using Indium, Journal of Organometallic Chemistry vol. 693(25) 3771-3779, 2008.

Li et al., Graphene-supported ZnO nanoparticles: An efficient heterogeneous catalyst for the Claisen-Schmidt condensation reaction without additional base. Tetrahedron Lett. 2017, 58 (42), 3984-3988.

Lin et al., Metal-Catalyzed Acyl Transfer Reactions of Enol Esters: Role of Y5(OiPr)13O and (thd)2Y(OiPr) as Transesterification Catalysts. Org. Lett. 2000, 2 (7), 997-1000.

Liu et al., Enantioselective γ-Alkylation of α,β-Unsaturated Malonates and Ketoesters by a Sequential Ir-Catalyzed Asymmetric Allylic Alkylation/Cope Rearrangement, J. Am. Chem. Soc. 2016, 138, 5234.

Longstreet, et al., Improved Synthesis of Mono- and Disubstituted 2-Halonicotinonitriles from Alkylidene Malononitriles, Org. Lett. 2013, 15 (20), 5298.

Mandal et al., Total Synthesis of Guanacastepene A: A Route to Enantiomeric Control, J. Org. Chem. 2005, 70, 10619.

Marković et al., The isolation and synthesis of neodolastane diterpenoids, Nat. Prod. Rep. 2015, 32, 230.

Meng et al., Electrophilic Addition of Allylic Carbocations to 2-Cyclopropylidene-2-arylethanols: A Strategy to 3-Oxabicyclo[3.2.0]heptanes. Adv. Synth. Catal. 2013, 355 (13), 2637-2650.

Michalak et al., Construction of the Tricyclic 5-7-6 Scaffold of Fungi-Derived Diterpenoids. Total Synthesis of (±)-Heptemerone G and an Approach to Danishefsky's Intermediate for Guanacastepene A Synthesis, J. Org. Chem. 2010, 75, 8337.

Miertuš et al., Approximate Evaluations of the Electrostatic Free Energy and Internal Energy Changes in Solution Processes. Chem. Phys. 1982, 65, 239-245.

Miertuš et al., Electrostatic Interaction of a Solute with a Continuum. A Direct Utilizaion of Ab Initio Molecular Potential for the Prevision of Solvent Effects. Chem. Phys. 1981, 55, 117-129.

METHODS AND COMPOSITIONS FOR TERPENOID TRICYCLOALKANE SYNTHESIS

CROSS-REFERENCE TO RELATED APPLICATIONS

This application is continuation of, and claims priority to, co-pending U.S. patent application Ser. No. 16/567,643, filed Sep. 11, 2019, and which U.S. patent application Ser. No. 16/567,643 is a continuation of, and claims priority to, U.S. application Ser. No. 16/383,425, now U.S. Pat. No. 10,487,047, filed Apr. 12, 2019, and which U.S. patent application Ser. No. 16/383,425 is a continuation of, and claims priority to, U.S. application Ser. No. 15/981,833, now U.S. Pat. No. 10,287,239, filed May 16, 2018 which application is incorporated herein fully by this reference.

BACKGROUND

Structurally complex terpenoid natural products have been recognized as important therapeutic agents. For example, taxol and ingenol are clinically used for the treatment of cancer and actinic keratosis, respectively. In addition to these important drugs, a multitude of related cycloheptane-containing terpenoid natural products have promising, but underexplored medicinal potential. For instance, englerin A and its analogs are being actively investigated for the treatment of renal cancer, phorbol and its esters have been intensely studied due to their potent biological activities, as have pseudoguaianolide natural products. Numerous other natural product classes, including abeo-taxane, neodolastane, cyathane, and icetexane, and individual natural products, such as anthecularin, sandresolide B, frondosin A, and liphagal display promising biological activities. The combination of the polycyclic carbon-framework's rigidity and differences resulting from the substitution and oxidation patterns thereon provide a rich array of potential biological activities. Other therapeutically and chemically interesting terpenoids are shown in FIG. 1.

Facile and systematic access to diverse substitution and oxidation patterns about carbocyclic frameworks would advance drug design and development. Accordingly, simplifying access to complex terpenoid scaffolds for application in the drug discovery process is a major goal of modern organic chemistry (e.g., see Huang, M., et al., *Expert Opin. Investig. Drugs* 2012, 21, 1801; Ghantous, A., et al., *Drug Discov. Today* 2010, 15, 668; and Wang, G., et al., In *Nat. Prod.*; Humana Press Inc., 2005; pp 197-227). For example, natural product analogs can be accessed by (a) semisynthesis (see Ganem, B.; Franke, R. R. *J. Org. Chem.* 2007, 72, 3981), (b) "total" or de novo synthesis (e.g., see Jansen, D. J.; Shenvi, R. A. *Future Med. Chem.* 2014, 6, 1127; Urabe, D.; Asaba, T.; Inoue, M. *Chem. Rev.* 2015, 115, 9207; and Maimone, T. J.; Baran, P. S. *Nat Chem Biol* 2007, 3 (7), 396), and by (c) diversity-oriented synthesis (e.g., see Cordier, C., et al., *Nat. Prod. Rep.* 2008, 25, 719; Huigens III, R. W., et al., *Nat. Chem.* 2013, 5, 195; Balthaser, B. R., et al., *Nat Chem* 2011, 3, 969; and McLeod, M. C., et al., *Nat. Chem.* 2014, 6, 133). However, many of these synthetic approaches are laborious and require complex reaction sequences, frequently use starting materials that are costly and rare; and/or are not easily scalable. Currently available synthetic routes do not provide methods that allow facile preparation of diverse terpenoid scaffolds that can be derivatized for biological evaluation.

Despite advances in research directed towards preparation of terpenoid cores and scaffolds, there remain a scarcity of methods for preparation of terpenoid cores that utilize abundant starting materials and simple reaction sequences that can be used to tunably and scalably assemble common terpenoid cores. Moreover, in view of the limitations of current methods, there are limited compounds comprising a terpenoid core that can be easily derivatized for biological evaluation. These needs and other needs are satisfied by the present disclosure.

SUMMARY

In accordance with the purpose(s) of the disclosure, as embodied and broadly described herein, the disclosure, in one aspect, relates to methods for preparation of intermediates useful for the preparation of terpenoid cores. In a further aspect, the disclosed methods pertain to the preparation of compounds comprising a terpenoid core or scaffold, such as 6/7/5 tricycloalkanes. The disclosed methods utilize abundant starting materials and simple reaction sequences that can be used to tunably and scalably assemble common terpenoid cores. In various aspects, the present disclosure pertains to compounds prepared using the disclosed methods.

Disclosed are compounds having a formula represented by a structure:

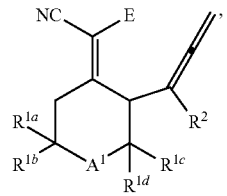

wherein E is —CN or —(C=O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C=O)OR$^{11}$; or wherein R$^{1a}$ and R$^{1c}$ are covalently bonded and, together with more intermediate carbons, comprise —CH$_2$CH$_2$—, or —CH=CH—; wherein m is an integer selected from 0, 1, 2, and 3; and wherein R$^{11}$ is C1-C6 alkyl; wherein R$^2$ is hydrogen, C1-C6 alkyl, aryl, or —(CH$_2$)$_n$(C=O)OR$^{12}$; wherein n is an integer selected from 0, 1, 2, and 3; and wherein R$^{12}$ is C1-C6 alkyl; wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C=O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_q$C=O)OR$^{30}$; wherein R$^{31}$ is C1-C6 alkyl; and wherein q is an integer selected from 0, 1, 2, and 3; and wherein R$^{22}$ is C1-C6 alkyl, or —(C=O)OR$^{32}$; and wherein R$^{32}$ is C1-C6 alkyl.

Also disclosed herein are compounds having a formula represented by a structure:

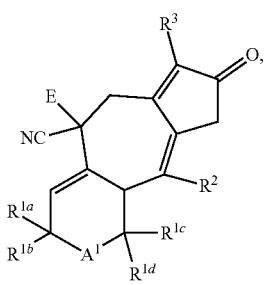

wherein E is —CN or —(C=O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C=O)OR$^{11}$; or wherein R$^{1a}$ and R$^{1c}$ are covalently bonded and, together with more intermediate carbons, comprise —CH$_2$CH$_2$—, or —CH=CH—; wherein m is an integer selected from 0, 1, 2, and 3; and wherein R$^{11}$ is C1-C6 alkyl; wherein R$^2$ is hydrogen, C1-C6 alkyl, aryl, or —(CH$_2$)$_n$(C=O)OR$^{12}$; wherein n is an integer selected from 0, 1, 2, and 3; and wherein R$^{12}$ is C1-C6 alkyl; wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C=O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_q$C=O)OR$^{30}$; wherein R$^{31}$ is C1-C6 alkyl; and wherein q is an integer selected from 0, 1, 2, and 3; and wherein R$^{22}$ is C1-C6 alkyl, or —(C=O)OR$^{32}$; and wherein R$^{32}$ is C1-C6 alkyl; wherein R$^3$ is hydrogen, C1-C6 alkyl, aryl, trimethylsilyl, or —(CH$_2$)$_r$(C=O)OR$^{15}$; wherein r is an integer selected from 0, 1, 2, and 3; and wherein R$^{15}$ is C1-C6 alkyl.

Also disclosed herein are methods of synthesizing an allenyne precursor to a terpenoid scaffold, the method comprising: reacting a γ-allenyl Knoevenagel adduct and a propargyl electrophile in the presence of a metal hydride; wherein the γ-allenyl Knoevenagel adduct has a formula represented by a structure:

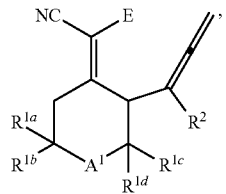

wherein E is —CN or —(C=O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C=O)OR$^{11}$; or wherein R$^{1a}$ and R$^{1c}$ are covalently bonded and, together with more intermediate carbons, comprise —CH$_2$CH$_2$—, or —CH=CH—; wherein m is an integer selected from 0, 1, 2, and 3; and wherein R$^{11}$ is C1-C6 alkyl; wherein R$^2$ is hydrogen, C1-C6 alkyl, aryl, or —(CH$_2$)$_n$(C=O)OR$^{12}$; wherein n is an integer selected from 0, 1, 2, and 3; and wherein R$^{12}$ is C1-C6 alkyl; wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C=O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_q$C=O)OR$^{30}$; wherein R$^{31}$ is C1-C6 alkyl; and wherein q is an integer selected from 0, 1, 2, and 3; and wherein R$^{22}$ is C1-C6 alkyl, or —(C=O)OR$^{32}$; and wherein R$^{32}$ is C1-C6 alkyl; and, wherein the propargyl electrophile has a formula represented by a structure:

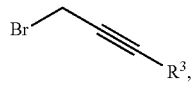

wherein R$^3$ is hydrogen, C1-C6 alkyl, aryl, trimethylsilyl, or —(CH$_2$)$_r$(C=O)OR$^{15}$; wherein r is an integer selected from 0, 1, 2, and 3; and wherein R$^{15}$ is C1-C6 alkyl; thereby synthesizing the allenyne precursor to the terpenoid scaffold; wherein the allenyne precursor to the terpenoid scaffold has a formula represented by a structure:

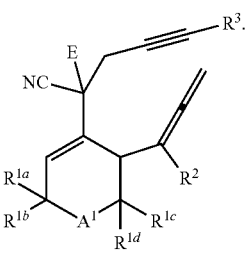

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 3A shows a generalized reaction scheme used to prepare 1,7-allenyne having structure 5 as shown in the figure. FIG. 3B shows specific representative 1,7 allenynes prepared, with the reaction sequences used and percent yield indicated by the compound labels beneath the product structure. The compound labels shown in FIGS. 3A-3B, i.e., 2a-2e, 3a-3f, 4a-4f, etc., refer to the compound labels used in the Examples herein below. In the reactions shown in FIGS. 3A-3B, the standard protocol was as follows: about 300 mg to about 2 g of 1,5-eyne substrate 3a-3f, toluene (0.1 M), 150° C., then swap toluene for THF (0.5 M), add NaH (1.1 equivalent), and propargyl bromide derivative (1.5 equivalents). In the figures and herein throughout, "rt" indicates room temperature.

FIG. 4A shows an exemplary 1,5-enyne that does not undergo [3,3] rearrangement. FIG. 4B shows a specific representative reaction sequence for 1,5-enynes that do undergo [3,3] rearrangement. FIG. 4C shows specific representative compounds that are prepared from 1,5-enynes that undergo [3,3] rearrangement. The compound labels shown in FIGS. 4A-4C, i.e., 3h-3k, 2d, 5hd-5kd, etc., refer to the compound labels used in the Examples herein below. In the reactions shown in FIGS. 4A-4C, the standard protocol was as follows: about 300 mg of 1,5-eyne substrate 3h-3k, toluene (0.1 M), 150° C., then swap toluene for THF (0.5 M), add NaH (1.1 equivalent), and propargyl bromide derivative 2d (1.5 equivalents).

FIG. 5A shows a generalized reaction scheme used to prepare allene/tethered π-systems having structures 7a, 7b, and 7c as shown in the figure with the substitutions and product yields as indicated in the figure. FIG. 5B show a specific representative reaction sequence used to prepare a representative allene/tethered π-system compound. FIG. 5C shows a specific representative reaction sequence used to prepare a representative allene/tethered π-system compound. The compound labels shown in FIGS. 5A-C, i.e., 3e, 7a, 7b, 7c, 7d, 7e, and 7f, refer to the compound lables used in the Examples herein below. In the reactions shown in FIGS. 5A-5C, the standard protocol was as follows: about 300 mg of 1,5-eyne substrate 3e, toluene (0.1 M), 150° C., then swap toluene for THF (0.5 M), add NaH (1.1 equivalent), and alkyl halide derivative 2d (1.5 equivalents).

FIG. 6A show a specific representative reaction sequence used to prepare a representative 6/7/5 tricycloalkane framework. FIG. 6B shows specific representative 6/7/5 tricycloalkane prepared, with the reaction sequences used and percent yield indicated by the compound labels beneath the product structure. The compound labels shown in FIGS. 6A-6B, i.e., 5aa, 6aa, 5cd, etc. refer to the compound lables used in the Examples herein below. In the reactions shown in FIGS. 6A-6B, the standard protocol was as follows: about 500 mg of allenyne 5, 1 atm CO, 10 mol % $[Rh(CO)_2Cl]_2$, p-xylene (0.005 M), 110° C.

FIG. 7A shows a representative disclosed compound prepared by a representative intramolecular Diels-Alder furan reaction. FIG. 7B shows 6/6/7 tricycloalkane natural products related in structure to the representative disclosed compound shown in FIG. 7A. The compound labels shown in FIGS. 7A-7B, i.e., 7e and 8 refer to the compound lables used in the Examples herein below.

FIG. 8A shows the preparation of compounds 9a and 9b from compound 6dd, with the specific functional group interconversion dependent upon the reaction conditions used as shown in the figure. FIG. 8B shows the preparation of compounds 9c and 9d from compound 6kd, with the specific functional group interconversion dependent upon the reaction conditions used as shown in the figure (see footnotes). The compound labels shown in FIGS. 8A-8B, i.e., 6dd, 9a, 9b, 6kd, 9c, and 9d refer to the compound lables used in the Examples herein below.

Figure 1:
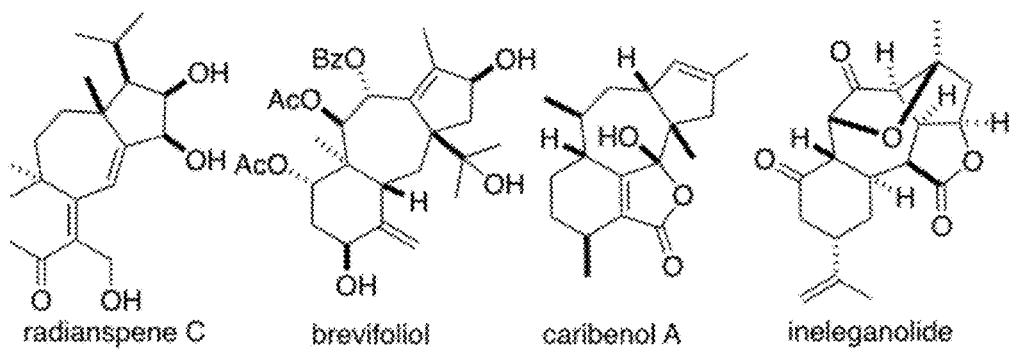
FIG. 1 shows representative 6/7/5 tricycloalkane terpenes.

Additional advantages of the disclosure will beset forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambidgesoft Corporation, U.S.A.).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "carboxylic acid" as used herein is represented by the formula —C(O)OH or —(C═O)OH.

The term "ester" as used herein is represented by the formula —OC(O)$A^1$, —C(O)O$A^1$, or —(C═O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula —($A^1$O(O)C—$A^2$—C(O)O)$_a$— or —($A^1$O(O)C—$A^2$—OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazoyl, imidazopyridinyl, pyrazolopyridinyl, and pyrazolopyrimidinyl. Further not limiting examples of heteroaryl groups include, but are not limited to, pyrdinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "nitrile" or "cyano" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

"$R^1$," "$R^2$," "$R^3$," ... "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$ NR°$_2$; —(CH$_2$)$_{0-4}$S(O)R°; —N(R°)

S(O)₂NR°₂; —N(R°)S(O)₂R°; —N(OR°)R°; —C(NH) NR°₂; —P(O)₂R°; —P(O)R°₂; —OP(O)R°₂; —OP(O) (OR°)₂; SiR°₃; —(C₁₋₄ straight or branched alkylene)O— N(R°)₂; or —(C₁₋₄ straight or branched alkylene)C(O)O— N(R°)₂, wherein each R° may be substituted as defined below and is independently hydrogen, C₁₋₆ aliphatic, —CH₂Ph, —O(CH₂)₀₋₁Ph, —CH₂-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH₂)₀₋₂R•, -(haloR•), —(CH₂)₀₋₂OH, —(CH₂)₀₋₂OR•, —(CH₂)₀₋₂CH(OR•)₂; —O(haloR•), —CN, —N₃, —(CH₂)₀₋₂C(O)R•, —(CH₂)₀₋₂C(O)OH, —(CH₂)₀₋₂C(O)OR•, —(CH₂)₀₋₂SR•, —(CH₂)₀₋₂SH, —(CH₂)₀₋₂NH₂, —(CH₂)₀₋₂NHR•, —(CH₂)₀₋₂NR•₂, —NO₂, —SiR•₃, —OSiR•₃, —C(O)SR•, —(C₁₋₄ straight or branched alkylene)C(O)OR•, or —SSR• wherein each R• is unsubstituted or where preceded by "halo" is substituted only with one or more halogens, and is independently selected from C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*₂, =NNHC(O)R*, =NNHC(O)OR*, =NNHS(O)₂R*, =NR*, =NOR*, —O(C(R*₂))₂₋₃O—, or —S(C(R*₂))₂₋₃S—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₃ O—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O) R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

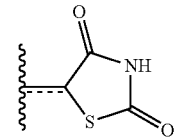

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

In some aspects, a structure of a compound can be represented by a formula:

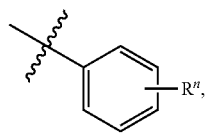

which is understood to be equivalent to a formula:

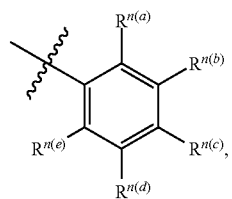

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. DISCLOSED COMPOUNDS

In one aspect, the present disclosure relates to compounds that can be used as intermediates useful for the preparation of terpenoid cores. In a further aspect, the disclosed methods pertain to the preparation of compounds comprising a terpenoid core or scaffold, such as 6/7/5 tricycloalkanes. The disclosed methods utilize abundant starting materials and simple reaction sequences that can be used to tunably and scalably assemble common terpenoid cores. In various aspects, the present disclosure pertains to compounds prepared using the disclosed methods.

1. Structure

In one aspect, the present disclosure relates to Knoevenagel adducts having a formula represented by a structure:

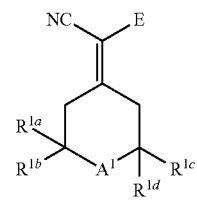

wherein E is —CN or —(C═O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C═O)OR$^{11}$; or wherein R$^{1a}$ and R$^{1c}$ are covalently bonded and, together with more intermediate carbons, comprise —CH$_2$CH$_2$—, or —CH═CH—; wherein m is an integer selected from 0, 1, 2, and 3; and wherein R$^{11}$ is C1-C6 alkyl; and wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C═O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_q$C═O)OR$^{31}$; wherein R$^{31}$ is C1-C6 alkyl; and wherein q is an integer selected from 0, 1, 2, and 3; and wherein R$^{22}$ is C1-C6 alkyl, or —(C═O)OR$^{32}$; and wherein R$^{32}$ is C1-C6 alkyl.

In a further aspect, the Knoevenagel adduct has a formula represented by a structure:

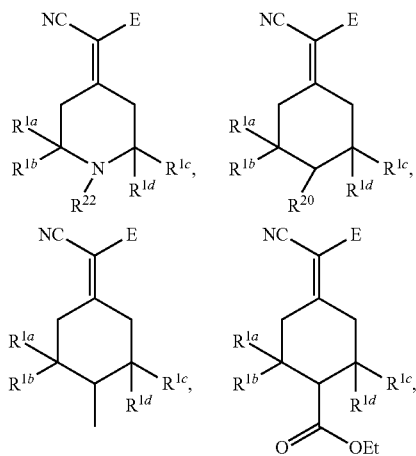

or combinations thereof.

In a further aspect, the Knoevenagel adduct has a formula represented by a structure:

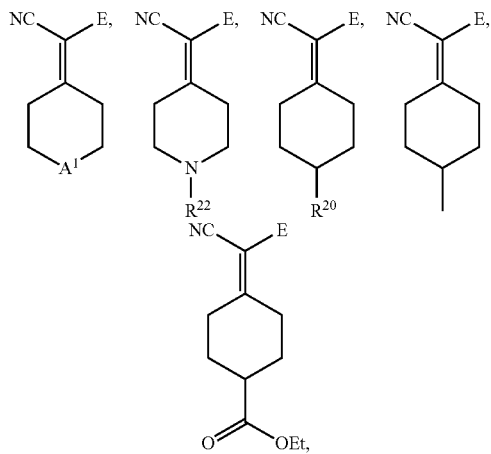

or combinations thereof.

In a further aspect, the Knoevenagel adduct has a formula represented by a structure:

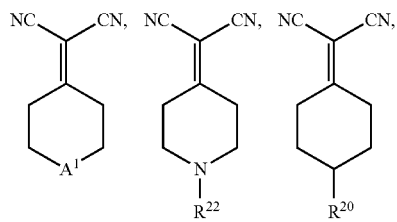

or combinations thereof.

In a further aspect, the Knoevenagel adduct has a formula represented by a structure:

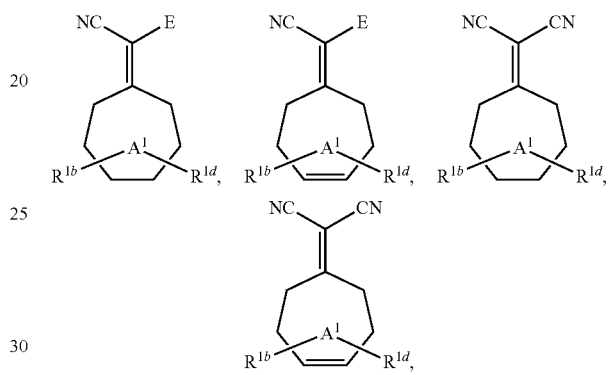

or combinations thereof.

In a further aspect, the Knoevenagel adduct has a formula represented by a structure:

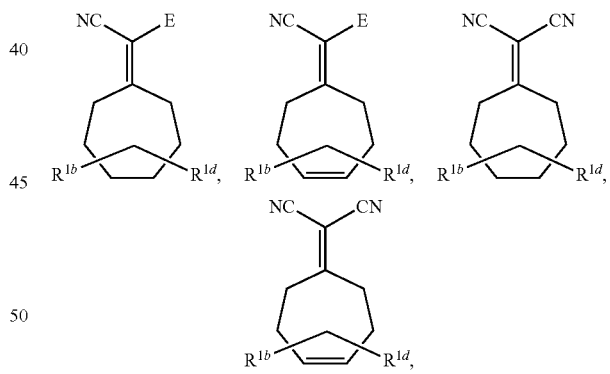

or combinations thereof.

In a further aspect, the Knoevenagel adduct has a formula represented by a structure:

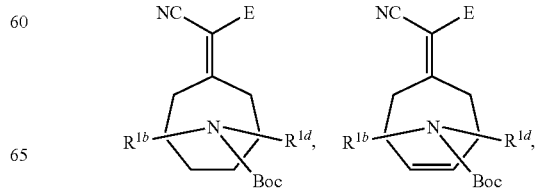

-continued

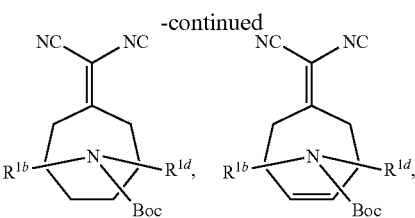

or combinations thereof.

In one aspect, the present disclosure relates to 1,5 enynes having a formula represented by a structure:

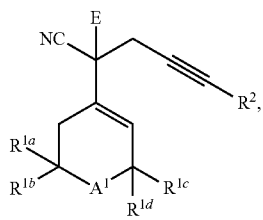

wherein E is —CN or —(C=O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C=O)OR$^{11}$; or wherein R$^{1a}$ and R$^{1c}$ are covalently bonded and, together with more intermediate carbons, comprise —CH$_2$CH$_2$—, or —CH=CH—; wherein m is an integer selected from 0, 1, 2, and 3; and wherein R$^{11}$ is C1-C6 alkyl; wherein R$^2$ is hydrogen, C1-C6 alkyl, aryl, or —(CH$_2$)$_n$(C=O)OR$^{12}$; wherein n is an integer selected from 0, 1, 2, and 3; and wherein R$^{12}$ is C1-C6 alkyl; wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C=O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_q$C=O)OR$^{31}$; wherein R$^{31}$ is C1-C6 alkyl; and wherein q is an integer selected from 0, 1, 2, and 3; and wherein R$^{22}$ is C1-C6 alkyl, or —(C=O)OR$^{32}$; and wherein R$^{32}$ is C1-C6 alkyl.

In one aspect, the present disclosure relates to 1,5 enynes having a formula represented by a structure:

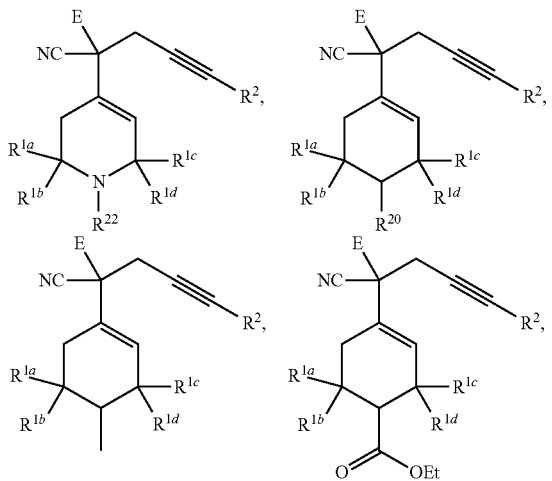

combinations thereof.

In one aspect, the present disclosure relates to 1,5 enynes having a formula represented by a structure:

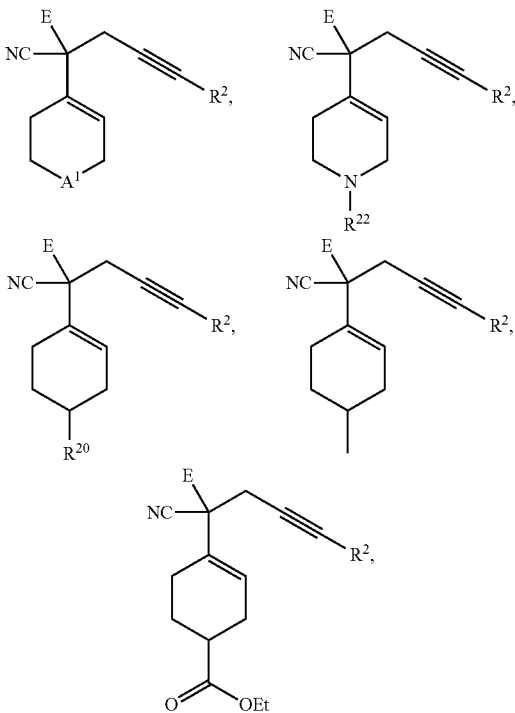

or combinations thereof.

In one aspect, the present disclosure relates to 1,5 enynes having a formula represented by a structure:

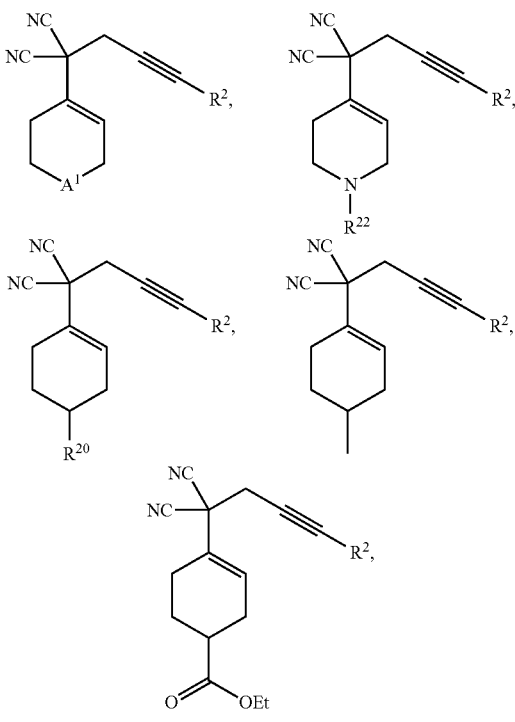

or combinations thereof.

In one aspect, the present disclosure relates to 1,5 enynes having a formula represented by a structure:

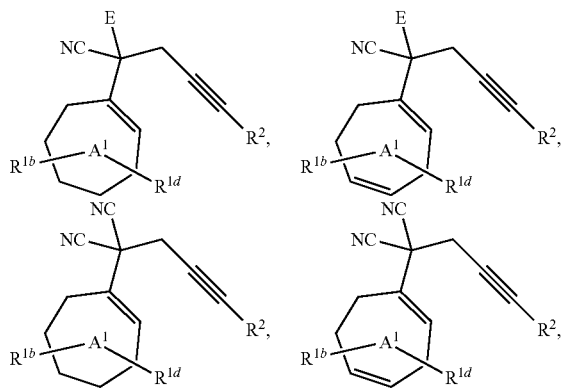

or combinations thereof.

In one aspect, the present disclosure relates to 1,5 enynes having a formula represented by a structure:

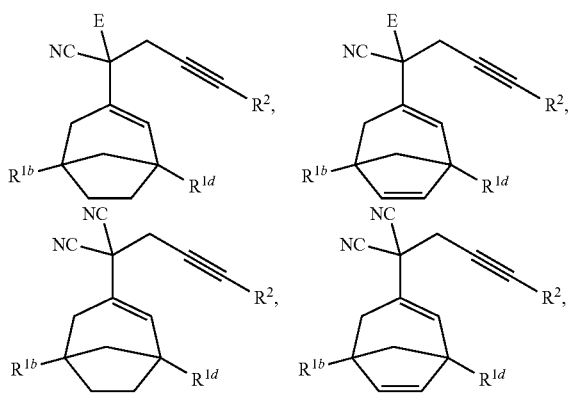

combinations thereof.

In one aspect, the present disclosure relates to 1,5 enynes having a formula represented by a structure:

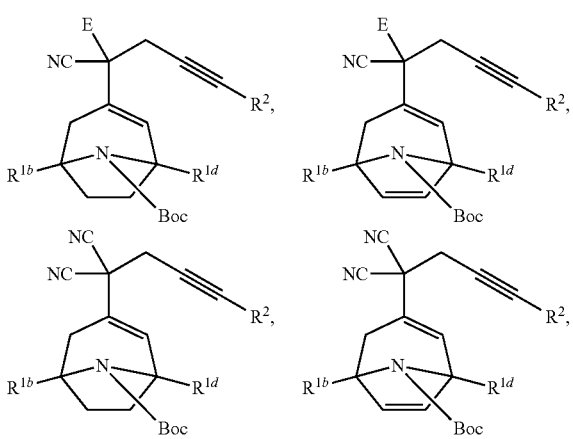

or combinations thereof.

In one aspect, the present disclosure relates to γ-allenyl Knoevenagel adducts having a formula represented by a structure:

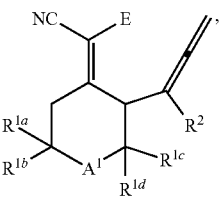

wherein E is —CN or —(C=O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C=O)OR$^{11}$; or wherein R$^{1a}$ and R$^{1c}$ are covalently bonded and, together with more intermediate carbons, comprise —CH$_2$CH$_2$—, or —CH=CH—; wherein m is an integer selected from 0, 1, 2, and 3; and wherein R$^{11}$ is C1-C6 alkyl; wherein R$^2$ is hydrogen, C1-C6 alkyl, aryl, or —(CH$_2$)$_n$(C=O)OR$^{12}$; wherein n is an integer selected from 0, 1, 2, and 3; and wherein R$^{12}$ is C1-C6 alkyl; wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C=O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_q$C=O)OR$^{31}$; wherein R$^{31}$ is C1-C6 alkyl; and wherein q is an integer selected from 0, 1, 2, and 3; and wherein R$^{22}$ is C1-C6 alkyl, or —(C=O)OR$^{32}$; and wherein R$^{32}$ is C1-C6 alkyl.

In one aspect, the present disclosure relates to γ-allenyl Knoevenagel adducts having a formula represented by a structure:

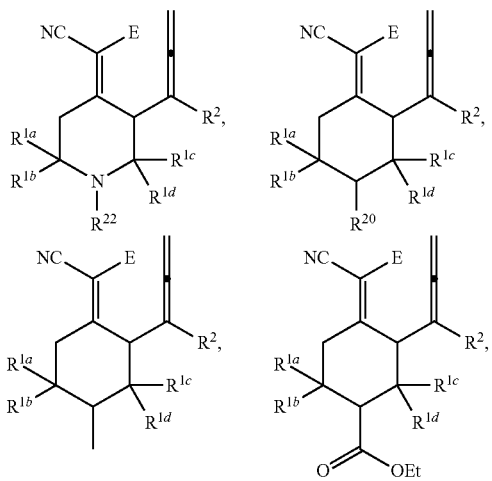

or combinations thereof.

In one aspect, the present disclosure relates to γ-allenyl Knoevenagel adducts having a formula represented by a structure:

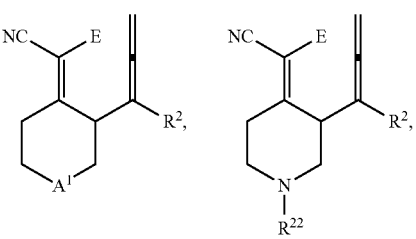

-continued

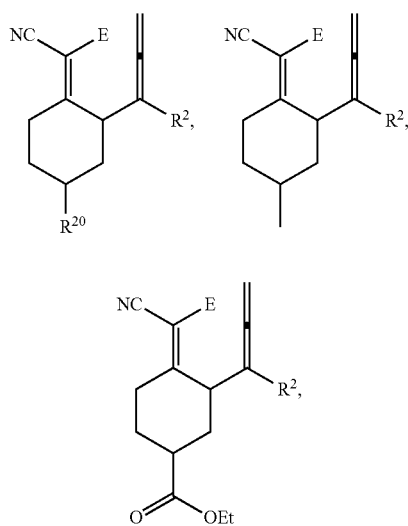

or combinations thereof.

In one aspect, the present disclosure relates to γ-allenyl Knoevenagel adducts having a formula represented by a structure:

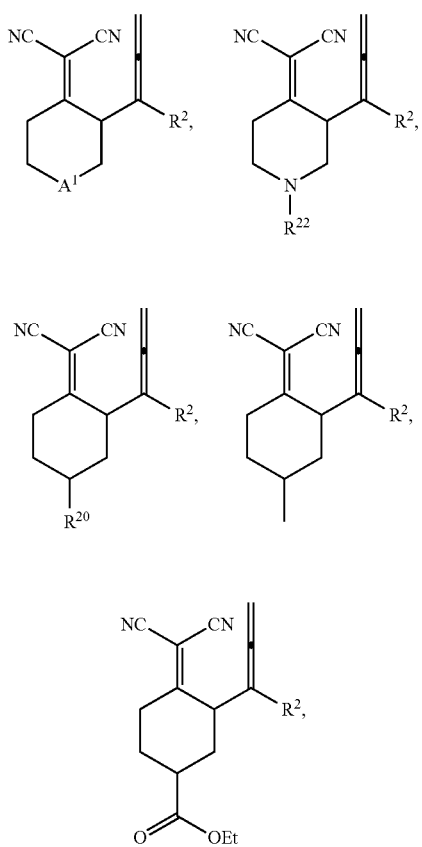

or combinations thereof.

In one aspect, the present disclosure relates to γ-allenyl Knoevenagel adducts having a formula represented by a structure:

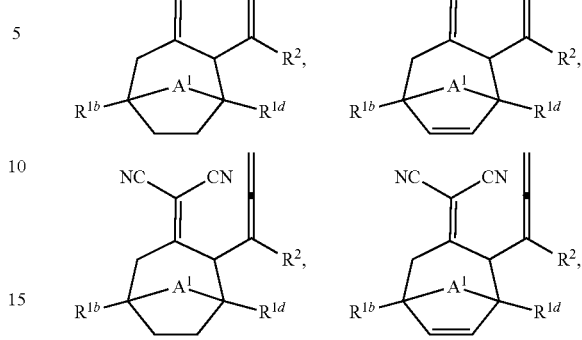

or combinations thereof.

In one aspect, the present disclosure relates to γ-allenyl Knoevenagel adducts having a formula represented by a structure:

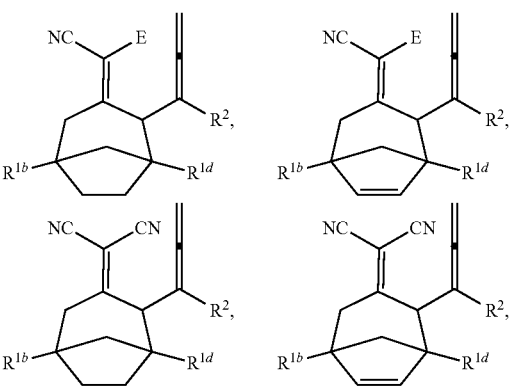

or combinations thereof.

In one aspect, the present disclosure relates to γ-allenyl Knoevenagel adducts having a formula represented by a structure:

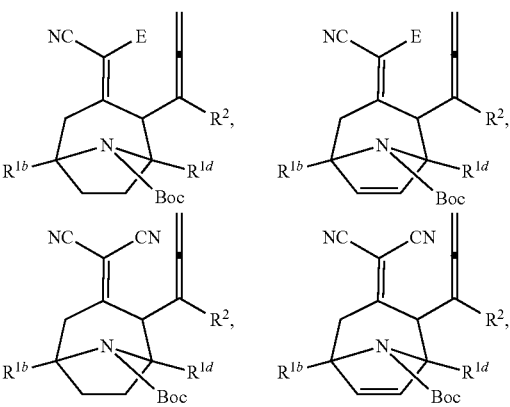

or combinations thereof.

In one aspect, the present disclosure relates to propargyl electrophiles having a formula represented by a structure:

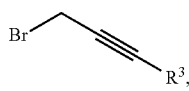

wherein R³ is hydrogen, C1-C6 alkyl, aryl, trimethylsilyl, or —(CH₂)ᵣ(C═O)OR¹⁵; wherein r is an integer selected from 0, 1, 2, and 3; and wherein R¹⁵ is C1-C6 alkyl.

In one aspect, the present disclosure relates to allenyne precursors to a terpenoid scaffold; wherein the allenyne precursor to the terpenoid scaffold has a formula represented by a structure:

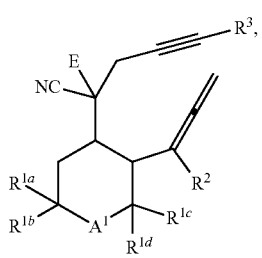

wherein E is —CN or —(C═O)OR¹⁰; wherein R¹⁰ is C1-C6 alkyl; wherein each of R¹ᵃ, R¹ᵇ, R¹ᶜ, and R¹ᵈ is independently hydrogen, C1-C6 alkyl, aryl, or —(CH₂)ₘ(C═O)OR¹¹; or wherein R¹ᵃ and R¹ᶜ are covalently bonded and, together with more intermediate carbons, comprise —CH₂CH₂—, or —CH═CH—; wherein m is an integer selected from 0, 1, 2, and 3; and wherein R¹¹ is C1-C6 alkyl; wherein R² is hydrogen, C1-C6 alkyl, aryl, or —(CH₂)ₙ(C═O)OR¹²; wherein n is an integer selected from 0, 1, 2, and 3; and wherein R¹² is C1-C6 alkyl; wherein A¹ is —C(R²⁰)(R²¹)—, —NR²²— or —CH₂—; wherein R²⁰ is hydrogen, C1-C6 alkyl, or —(CH₂)ₚC═O)OR³⁰; wherein R³⁰ is C1-C6 alkyl; and wherein p is an integer selected from 0, 1, 2, and 3; wherein R²¹ is hydrogen, C1-C6 alkyl, or —(CH₂)_qC═O)OR³¹; wherein R³¹ is C1-C6 alkyl; and wherein q is an integer selected from 0, 1, 2, and 3; and wherein R²² is C1-C6 alkyl, or —(C═O)OR³²; and wherein R³² is C1-C6 alkyl; and wherein R³ is hydrogen, C1-C6 alkyl, aryl, trimethylsilyl, or —(CH₂)ᵣ(C═O)OR¹⁵; wherein r is an integer selected from 0, 1, 2, and 3; and wherein R¹⁵ is C1-C6 alkyl.

In one aspect, the present disclosure relates to allenyne precursors to a terpenoid scaffold; wherein the allenyne precursor to the terpenoid scaffold has a formula represented by a structure:

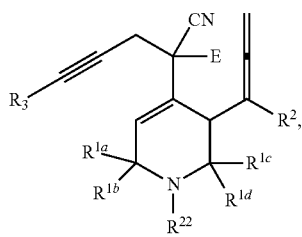

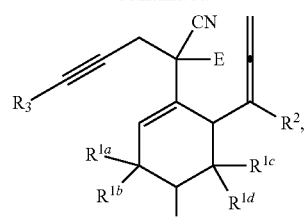

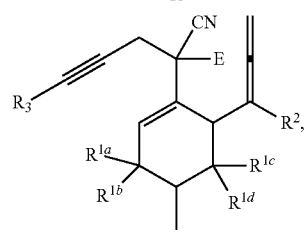

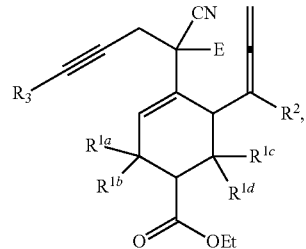

or combinations thereof.

In one aspect, the present disclosure relates to allenyne precursors to a terpenoid scaffold; wherein the allenyne precursor to the terpenoid scaffold has a formula represented by a structure:

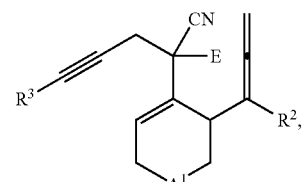

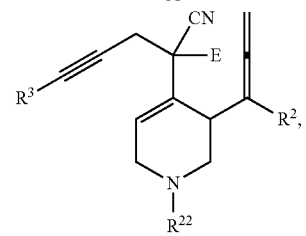

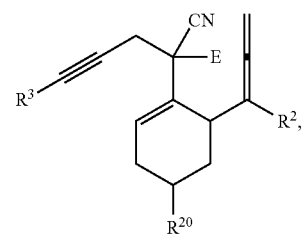

-continued

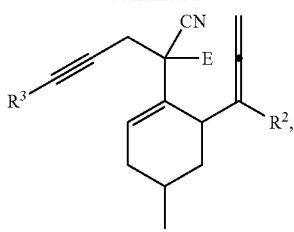

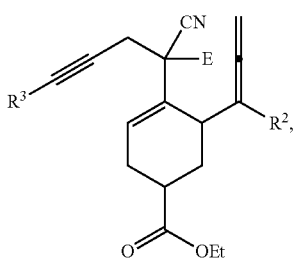

or combinations thereof.

In one aspect, the present disclosure relates to allenyne precursors to a terpenoid scaffold; wherein the allenyne precursor to the terpenoid scaffold has a formula represented by a structure:

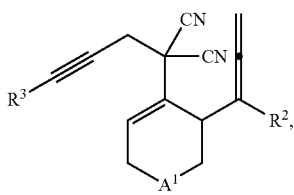

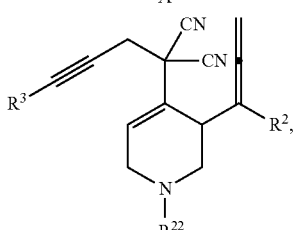

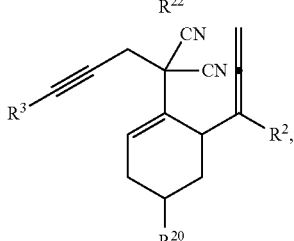

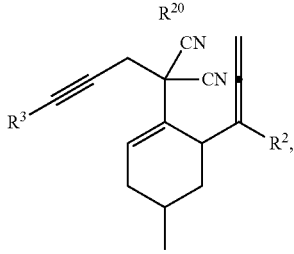

-continued

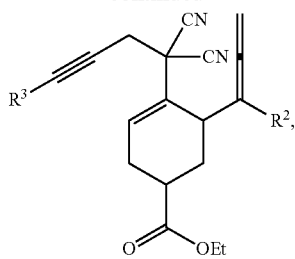

or combinations thereof.

In one aspect, the present disclosure relates to allenyne precursors to a terpenoid scaffold; wherein the allenyne precursor to the terpenoid scaffold has a formula represented by a structure:

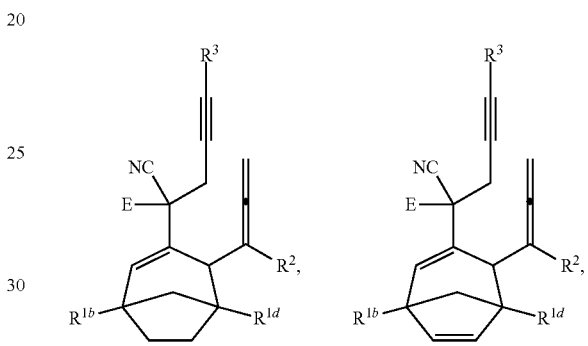

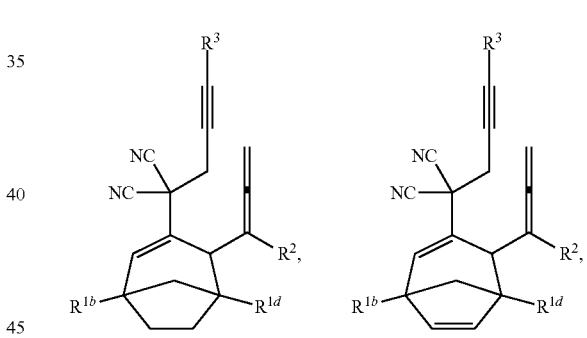

or combinations thereof.

In one aspect, the present disclosure relates to allenyne precursors to a terpenoid scaffold; wherein the allenyne precursor to the terpenoid scaffold has a formula represented by a structure:

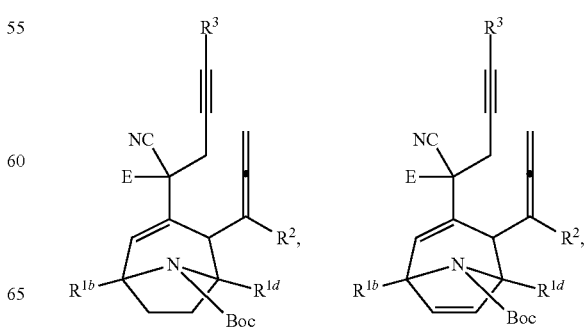

-continued

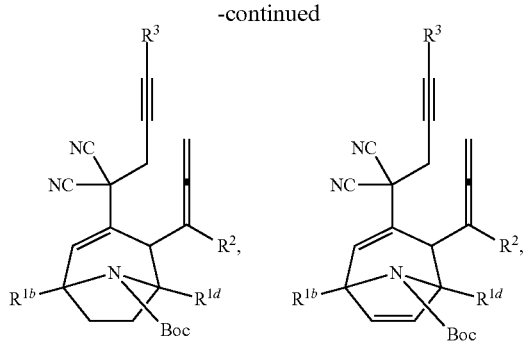

or combinations thereof.

In one aspect, the present disclosure relates to allenyne precursors to a terpenoid scaffold; wherein the allenyne precursor to the terpenoid scaffold has a formula represented by a structure:

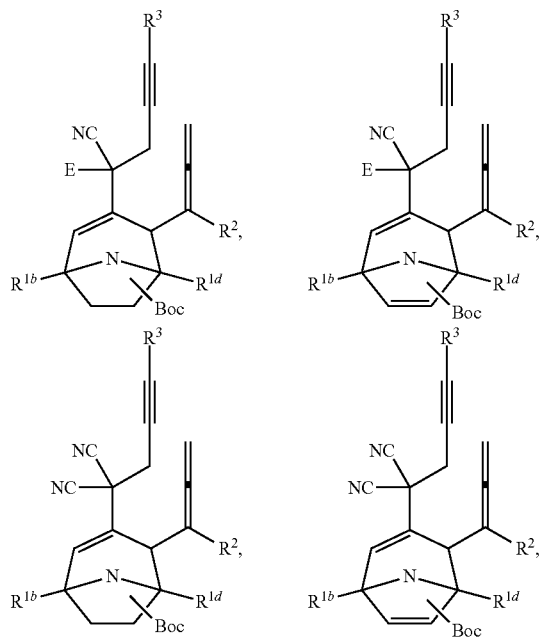

or combinations thereof.

In one aspect, the present disclosure relates to terpenoid scaffolds having a formula represented by a structure:

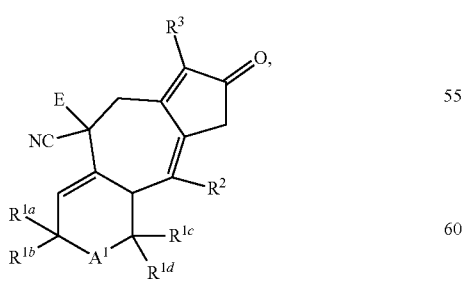

wherein E is —CN or —(C=O)OR$^{10}$; wherein R$^{10}$ is C1-C6 alkyl; wherein each of R$^{1a}$, R$^{1b}$, R$^{1c}$, and R$^{1d}$ is independently hydrogen, C1-C6 alkyl, aryl, or —(CH$_2$)$_m$(C=O)OR$^{11}$; or wherein R$^{1a}$ and R$^{1c}$ are covalently bonded and, together with more intermediate carbons, comprise —CH$_2$CH$_2$—, or —CH=CH—; wherein m is an integer selected from 0, 1, 2, and 3; and wherein R$^{11}$ is C1-C6 alkyl; wherein R$^2$ is hydrogen, C1-C6 alkyl, aryl, or —(CH$_2$)$_n$(C=O)OR$^{12}$; wherein n is an integer selected from 0, 1, 2, and 3; and wherein R$^{12}$ is C1-C6 alkyl; wherein A$^1$ is —C(R$^{20}$)(R$^{21}$)—, —NR$^{22}$— or —CH$_2$—; wherein R$^{20}$ is hydrogen, C1-C6 alkyl, or —(CH$_2$)$_p$C=O)OR$^{30}$; wherein R$^{30}$ is C1-C6 alkyl; and wherein p is an integer selected from 0, 1, 2, and 3; wherein R$^{21}$ is hydrogen, C1-C6 alkyl, or —(CH$_2$)$_p$C=O)OR$^{30}$; wherein R$^{31}$ is C1-C6 alkyl; and wherein q is an integer selected from 0, 1, 2, and 3; and wherein R$^{22}$ is C1-C6 alkyl, or —(C=O)OR$^{32}$; and wherein R$^{32}$ is C1-C6 alkyl; wherein R$^3$ is hydrogen, C1-C6 alkyl, aryl, trimethylsilyl, or —(CH$_2$)$_r$(C=O)OR$^{15}$; wherein r is an integer selected from 0, 1, 2, and 3; and wherein R$^{15}$ is C1-C6 alkyl.

In one aspect, the present disclosure relates to terpenoid scaffolds having a formula represented by a structure:

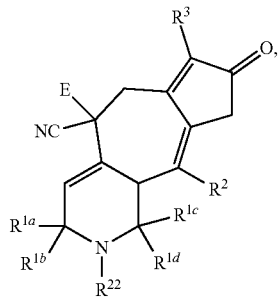

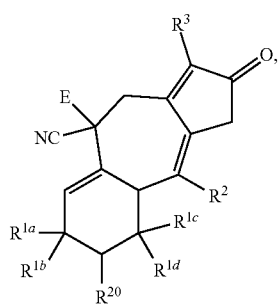

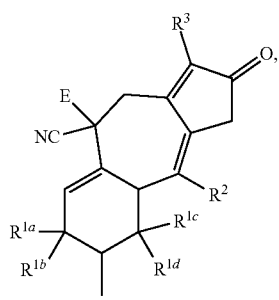

-continued

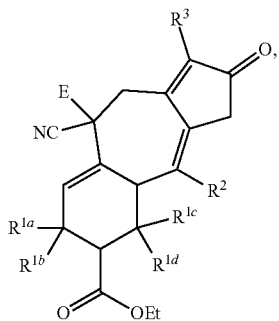

or combinations thereof.

In one aspect, the present disclosure relates to terpenoid scaffolds having a formula represented by a structure:

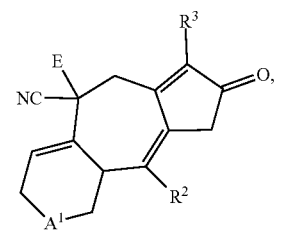 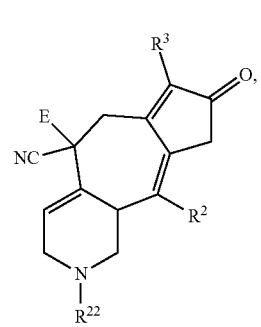

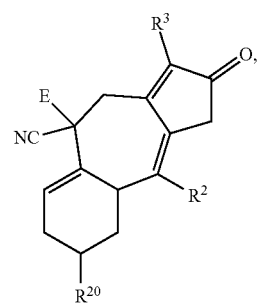 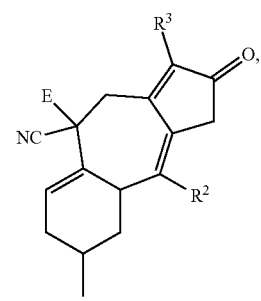

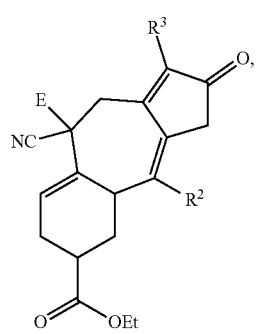

or combinations thereof.

In one aspect, the present disclosure relates to terpenoid scaffolds having a formula represented by a structure:

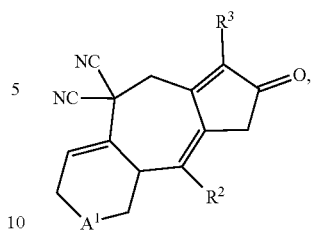 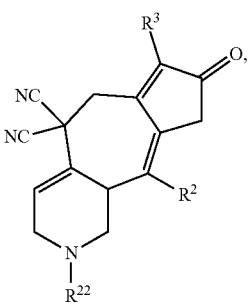

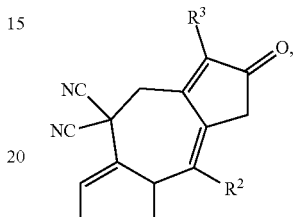 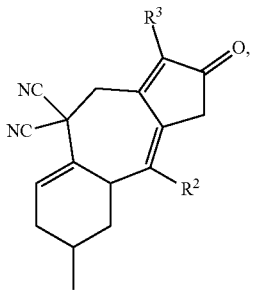

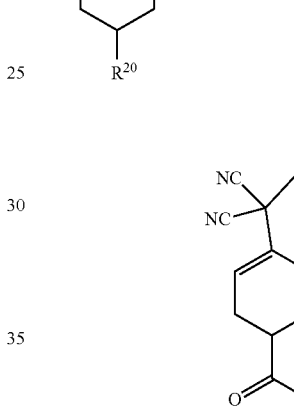

or combinations thereof.

In one aspect, the present disclosure relates to terpenoid scaffolds having a formula represented by a structure:

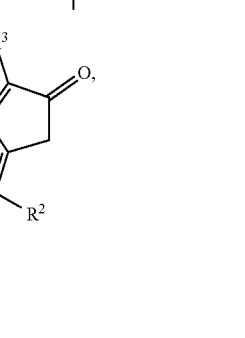

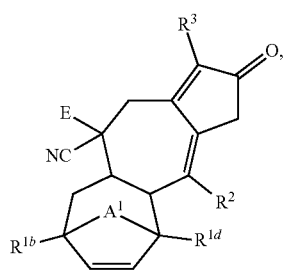

-continued

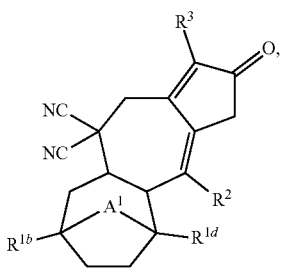

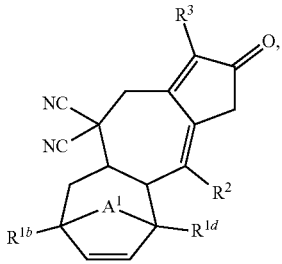

or combinations thereof.

In one aspect, the present disclosure relates to terpenoid scaffolds having a formula represented by a structure:

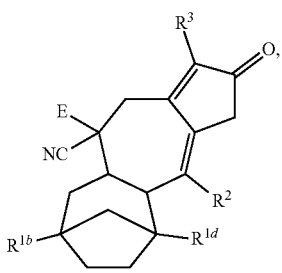

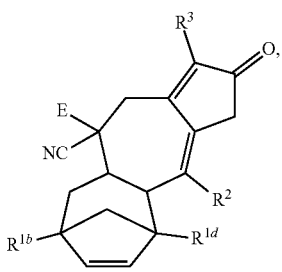

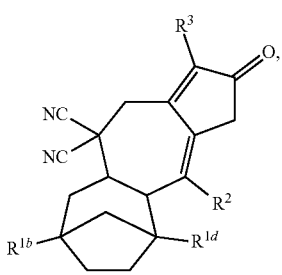

-continued

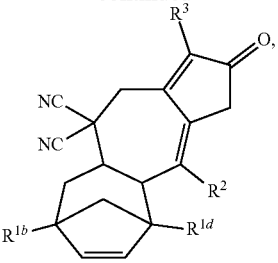

or combinations thereof.

In one aspect, the present disclosure relates to terpenoid scaffolds having a formula represented by a structure:

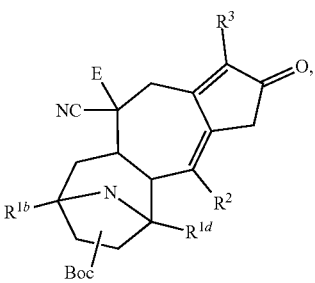

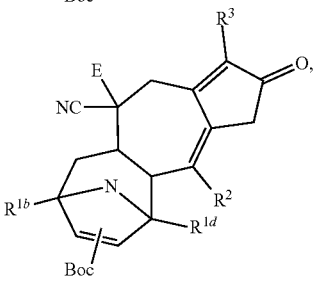

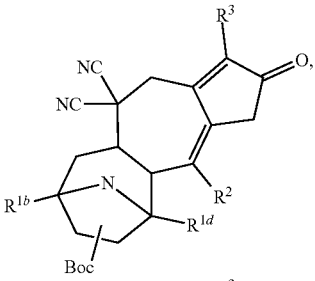

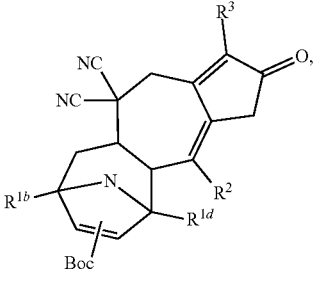

or combinations thereof.

2. $A^1$ Group

In one aspect, $A^1$ is —C($R^{20}$)($R^{21}$)—, —$NR^{22}$— or —$CH_2$—; $R^{20}$ is hydrogen, C1-C6 alkyl, or —$(CH_2)_pC$=O) $OR^3$; wherein $R^{30}$ is C1-C6 alkyl; and wherein p is an integer selected from 0, 1, 2, and 3; $R^{21}$ is hydrogen, C1-C6 alkyl, or —$(CH_2)_qC$(=O)$OR^{31}$; wherein $R^{31}$ is C1-C6 alkyl; and wherein q is an integer selected from 0, 1, 2, and 3; and $R^{22}$ is C1-C6 alkyl, or —(C=O)$OR^{32}$; and wherein $R^{32}$ is C1-C6 alkyl. In a further aspect, $A^1$ is —C($R^{20}$)($R^{21}$)—, —$NR^{22}$— or —$CH_2$—; $R^{20}$ is hydrogen, C1-C6 alkyl, or —$(CH_2)_pC$(=O)$OR^{30}$; wherein $R^{30}$ is C1-C6 alkyl; and wherein p is an integer selected from 0, 1, and 2; $R^{21}$ is hydrogen, C1-C6 alkyl, or —$(CH_2)_qC$(=O)$OR^{31}$; wherein $R^{31}$ is C1-C6 alkyl; and wherein q is an integer selected from 0, 1, and 2; and $R^{22}$ is C1-C6 alkyl, or —(C=O)$OR^{32}$; and wherein $R^{32}$ is C1-C6 alkyl. In a still further aspect, $A^1$ is —C($R^{20}$)($R^{21}$)—, —$NR^{22}$— or —$CH_2$—; $R^{20}$ is hydrogen, C1-C6 alkyl, or —$(CH_2)_pC$(=O)$OR^{30}$; wherein $R^{30}$ is C1-C6 alkyl; and wherein p is an integer selected from 0 and 1; $R^{21}$ is hydrogen, C1-C6 alkyl, or —$(CH_2)_qC$(=O)$OR^{31}$; wherein $R^{31}$ is C1-C6 alkyl; and wherein q is an integer selected from 0 and 1; and $R^{22}$ is C1-C6 alkyl, or —(C=O)$OR^{32}$; and wherein $R^{32}$ is C1-C6 alkyl. In a yet further aspect, $A^1$ is —C($R^{20}$)($R^{21}$)—, —$NR^{22}$— or —$CH_2$—; $R^{20}$ is hydrogen, C1-C6 alkyl, or —$(CH_2)_2$(C=O)$OR^{30}$; wherein $R^{30}$ is C1-C6 alkyl; $R^{21}$ is hydrogen, C1-C6 alkyl, or —$(CH_2)_2$(C=O)$OR^{31}$; wherein $R^{31}$ is C1-C6 alkyl; and wherein q is an integer selected from 0, 1, 2, and 3; and $R^{22}$ is C1-C6 alkyl, or —(C=O)$OR^{32}$; and wherein $R^{32}$ is C1-C6 alkyl. In an even further aspect, $A^1$ is —C($R^{20}$)($R^{21}$)—, —$NR^{22}$— or —$CH_2$—; $R^{20}$ is hydrogen, C1-C6 alkyl, or —$(CH_2)$(C=O)$OR^{30}$; wherein $R^{30}$ is C1-C6 alkyl; $R^{21}$ is hydrogen, C1-C6 alkyl, or —$(CH_2)$(C=O)$OR^{31}$; wherein $R^{31}$ is C1-C6 alkyl; and wherein q is an integer selected from 0, 1, 2, and 3; and $R^{22}$ is C1-C6 alkyl, or —(C=O)$OR^{32}$; and wherein $R^{32}$ is C1-C6 alkyl.

In a further aspect, $A^1$ is —$CH_2$—, —CH($CH_3$)—, —C($CH_3$)$_2$—, —CH($CH_2CH_3$)—, —CH($CH_2$)(C=O)$OCH_3$, —CH($CH_2$)(C=O)$OCH_2CH_3$, —CH($CH_2$)(C=O)O($CH_2$)$_2CH_3$, —CH($CH_2$)(C=O)OCH($CH_3$)$_2$, —CH($CH_2$)(C=O)O($CH_2$)$_3CH_3$, —CH(C=O)$OCH_3$, —CH(C=O)$OCH_2CH_3$, —CH(C=O)O($CH_2$)$_2CH_3$, —CH(C=O)OCH($CH_3$)$_2$, or —CH(C=O)O($CH_2$)$_3CH_3$, or -NBoc-. In a still further aspect, $A^1$ is —$CH_2$—, —CH($CH_3$)—, —CH($CH_2CH_3$)—, —CH($CH_2$)(C=O)$OCH_3$, —CH($CH_2$)(C=O)$OCH_2CH_3$, —CH(C=O)$OCH_3$, —CH(C=O)$OCH_2CH_3$, —CH(C=O)O($CH_2$)$_2CH_3$, or -NBoc-. In a yet further aspect, $A^1$ is —H$_2$—, —CH($CH_3$)—, —CH($CH_2$)(C=O)$OCH_3$, —CH(C=O)$OCH_3$, or -NBoc-. In an even further aspect, $A^1$ is —$CH_2$—, —CH($CH_3$)—, —CH($CH_2$)(C=O)$OCH_3$, —CH(C=O)$OCH_3$, or -NBoc-.

In a further aspect, $A^1$ is —$CH_2$—, —CH($CH_3$)—, —C($CH_3$)$_2$—, or —CH($CH_2CH_3$)—. In a still further aspect, $A^1$ is —$CH_2$—, —CH($CH_3$)—, or —CH($CH_2CH_3$)—. In a yet further aspect, $A^1$ is —$CH_2$— or —CH($CH_3$)—. In an even further aspect, $A^1$ is —$CH_2$—. In a still further aspect, $A^1$ is —CH($CH_3$)—.

In a further aspect, $A^1$ is -NBoc-.

3. E Group

In one aspect, E is —CN or —(C=O)$OR^{10}$. In a further aspect, E is CN. In a still further aspect, E is —(C=O)$OR^{10}$. In a yet further aspect, E is —(C=O)$OCH_3$, —(C=O)$OCH_2CH_3$, —(C=O)O($CH_2$)$_2CH_3$, —(C=O)OCH($CH_3$)$_2$, or —(C=O)O($CH_2$)$_3CH_3$. In an even further aspect, E is —(C=O)$OCH_3$ or —(C=O)$OCH_2CH_3$. In various further aspects, E is CN, —(C=O)$OCH_3$, —(C=O)$OCH_2CH_3$, —(C=O)O($CH_2$)$_2CH_3$, —(C=O)OCH($CH_3$)$_2$, or —(C=O)O($CH_2$)$_3CH_3$. In a further aspect, E is CN, —(C=O)$OCH_3$, or —(C=O)$OCH_2CH_3$. In a yet further aspect, E is CN or —(C=O)$OCH_3$.

4. $R^{1A}$, $R^{1B}$, $R^{1C}$, and $R^{1D}$ Groups

In one aspect, each of $R^{1a}$, $R^{1b}$, $R^{1c}$, and $R^{1d}$ is independently hydrogen, C1-C6 alkyl, aryl, or —$(CH_2)_m$(C=O)$OR^{11}$; $R^{11}$ is C1-C6 alkyl; and m is an integer selected from 0, 1, 2, and 3; or $R^{1a}$ and $R^{1c}$ are covalently bonded and, together with more intermediate carbons, comprise —$CH_2CH_2$—, or —CH=CH—. In a further aspect, each of $R^{1a}$, $R^{1b}$, $R^{1c}$, and $R^{1d}$ is independently hydrogen, C1-C6 alkyl, aryl, or —$(CH_2)_m$(C=O)$OR^{11}$; $R^{11}$ is C1-C6 alkyl; and m is an integer selected from 0, 1, and 2; or $R^{1a}$ and $R^{1c}$ are covalently bonded and, together with more intermediate carbons, comprise —$CH_2CH_2$—, or —CH=CH—. In a still further aspect, each of $R^{1a}$, $R^{1b}$, $R^{1c}$, and $R^{1d}$ is independently hydrogen, C1-C6 alkyl, aryl, or —$(CH_2)_m$(C=O)$OR^{11}$; $R^{11}$ is C1-C6 alkyl; and m is an integer selected from 0 and 1; or $R^{1a}$ and $R^{1c}$ are covalently bonded and, together with more intermediate carbons, comprise —$CH_2CH_2$—, or —CH=CH—. In an even further aspect, each of $R^{1a}$, $R^{1b}$, $R^{1c}$, and $R^{1d}$ is independently hydrogen, C1-C6 alkyl, aryl, or —$(CH_2)$(C=O)$OR^{11}$; $R^{11}$ is C1-C6 alkyl; or $R^{1a}$ and $R^{1c}$ are covalently bonded and, together with more intermediate carbons, comprise —$CH_2CH_2$—, or —CH=CH—. In a still further aspect, each of $R^{1a}$, $R^{1b}$, $R^{1c}$, and $R^{1d}$ is independently hydrogen, C1-C6 alkyl, aryl, or —$(CH_2)_2$(C=O)$OR^{11}$; $R^{11}$ is C1-C6 alkyl; or $R^{1a}$ and $R^{1c}$ are covalently bonded and, together with more intermediate carbons, comprise —$CH_2CH_2$—, or —CH=CH—.

In a further aspect, $R^{1b}$ and $R^{1d}$ are each independently hydrogen, C1-C6 alkyl, aryl, or —$(CH_2)_m$(C=O)$OR^{11}$; $R^{11}$ is C1-C6 alkyl; m is an integer selected from 0, 1, 2, and 3; and $R^{1a}$ and $R^{1c}$ are covalently bonded and, together with more intermediate carbons, comprise —$CH_2CH_2$—, or —CH=CH—. In a still further aspect, $R^{1b}$ and $R^{1d}$ are each hydrogen; and $R^{1a}$ and $R^{1c}$ are covalently bonded and, together with more intermediate carbons, comprise —$CH_2CH_2$—, or —CH=CH—. In a yet further aspect, $R^{1b}$ and $R^{1d}$ are each hydrogen; and $R^{1a}$ and $R^{1c}$ are covalently bonded and, together with more intermediate carbons, comprise —$CH_2CH_2$—. In an even further aspect, $R^{1b}$ and $R^{1d}$ are each hydrogen; and $R^{1a}$ and $R^{1c}$ are covalently bonded and, together with more intermediate carbons, comprise —CH=CH—.

In a further aspect, each of $R^{1a}$, $R^{1b}$, $R^{1c}$, and $R^{1d}$ is independently hydrogen, C1-C6 alkyl, aryl, or —$(CH_2)_m$(C=O)$OR^{11}$; $R^{11}$ is C1-C6 alkyl; and m is an integer selected from 0, 1, 2, and 3.

In a further aspect, each of $R^{1a}$, $R^{1b}$, $R^{1c}$, and $R^{1d}$ is independently hydrogen, methyl, ethyl, propyl, isopropyl, tert-butyl, sec-butyl, isobutyl, neopentyl, isopentyl, sec-pentyl, tert-pentyl, —$(CH_2)$(C=O)$OCH_3$, —$(CH_2)$(C=O)$OCH_2CH_3$, —$(CH_2)$(C=O)O($CH_2$)$_2CH_3$, —$(CH_2)$(C=O)OCH($CH_3$)$_2$, —$(CH_2)$(C=O)O($CH_2$)$_3CH_3$, —(C=O)$OCH_3$, —(C=O)$OCH_2CH_3$, —(C=O)O($CH_2$)$_2CH_3$, —(C=O)OCH($CH_3$)$_2$, or —(C=O)O($CH_2$)$_3CH_3$. In a still further aspect, each of $R^{1a}$, $R^{1b}$, $R^{1c}$, and $R^{1d}$ is independently hydrogen, methyl, ethyl, propyl, isopropyl, tert-butyl, sec-butyl, isobutyl, —$(CH_2)$(C=O)$OCH_3$, —$(CH_2)$(C=O)$OCH_2CH_3$, —$(CH_2)$(C=O)O($CH_2$)$_2CH_3$, —$(CH_2)$(C=O)OCH($CH_3$)$_2$, —$(CH_2)$(C=O)O($CH_2$)$_3CH_3$, —(C=O)$OCH_3$, —(C=O)$OCH_2CH_3$, —(C=O)O($CH_2$)$_2CH_3$, —(C=O)OCH($CH_3$)$_2$, or —(C=O)O($CH_2$)$_3CH_3$. In a yet further aspect, each of $R^{1a}$, $R^{1b}$, $R^{1c}$, and $R^{1d}$ is independently hydrogen, methyl, ethyl, propyl, isopropyl, —$(CH_2)$ (C=O)OCH₃, —(CH₂)(C=O)OCH₂CH₃, —(CH₂)(C=O)O(CH₂)₂CH₃, —(CH₂)(C=O)OCH(CH₃)₂, —(C=O)OCH₃, —(C=O)OCH₂CH₃, —(C=O)O(CH₂)₂CH₃, or —(C=O)OCH(CH₃)₂. In an even further aspect, each of $R^{1a}$, $R^{1b}$, $R^{1c}$, and $R^{1d}$ is independently hydrogen, methyl, ethyl, —(CH₂)(C=O)OCH₃, —(CH₂)(C=O)OCH₂CH₃, —(C=O)OCH₃, or —(C=O)OCH₂CH₃. In a still further aspect, each of $R^{1a}$, $R^{1b}$, $R^{1c}$, and $R^{1d}$ is independently hydrogen, methyl, —(CH₂)(C=O)OCH₃, or —(C=O)OCH₃.

In a further aspect, each of $R^{1a}$, $R^{1b}$, $R^{1c}$, and $R^{1d}$ is independently hydrogen, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(CH₂)(C=O)O(CH₂)₃CH₃, —(C=O)OCH₃, —(C=O)OCH₂CH₃, —(C=O)O(CH₂)₂CH₃, —(C=O)OCH(CH₃)₂, or —(C=O)O(CH₂)₃CH₃. In a still further aspect, each of $R^{1a}$, $R^{1b}$, $R^{1c}$, and $R^{1d}$ is independently hydrogen, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(CH₂)(C=O)O(CH₂)₃CH₃, —(C=O)OCH₃, —(C=O)OCH₂CH₃, —(C=O)O(CH₂)₂CH₃, —(C=O)OCH(CH₃)₂, or —(C=O)O(CH₂)₃CH₃. In a yet further aspect, each of $R^{1a}$, $R^{1b}$, $R^{1c}$, and $R^{1d}$ is independently hydrogen, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(C=O)OCH₃, —(C=O)OCH₂CH₃, —(C=O)O(CH₂)₂CH₃, or —(C=O)OCH(CH₃)₂. In an even further aspect, each of $R^{1a}$, $R^{1b}$, $R^{1c}$, and $R^{1d}$ is independently hydrogen, —(CH₂)(C=O)OCH₃, —(CH₂)(C=O)OCH₂CH₃, —(C=O)OCH₃, or —(C=O)OCH₂CH₃. In a still further aspect, each of $R^{1a}$, $R^{1b}$, $R^{1c}$, and $R^{1d}$ is independently hydrogen, —(CH₂)(C=O)OCH₃, or —(C=O)OCH₃.

In a further aspect, each of $R^{1a}$, $R^{1b}$, $R^{1c}$, and $R^{1d}$ is independently hydrogen or C1-C6 alkyl. In a further aspect, each of $R^{1a}$, $R^{1b}$, $R^{1c}$, and $R^{1d}$ is independently hydrogen, methyl, ethyl, propyl, isopropyl, tert-butyl, sec-butyl, isobutyl, neopentyl, isopentyl, sec-pentyl, or tert-pentyl. In a still further aspect, each of $R^{1a}$, $R^{1b}$, $R^{1c}$, and $R^{1d}$ is independently hydrogen, methyl, ethyl, propyl, isopropyl, tert-butyl, sec-butyl, or isobutyl. In a yet further aspect, each of $R^{1a}$, $R^{1b}$, $R^{1c}$, and $R^{1d}$ is independently hydrogen, methyl, ethyl, propyl, or isopropyl. In a yet further aspect, each of $R^{1a}$, $R^{1b}$, $R^{1c}$, and $R^{1d}$ is independently methyl or ethyl. In a still further aspect, each of $R^{1a}$, $R^{1b}$, $R^{1c}$, and $R^{1d}$ is independently hydrogen or methyl. In a yet further aspect, each of $R^{1a}$, $R^{1b}$, $R^{1c}$, and $R^{1d}$ is hydrogen. In an even further aspect, each of $R^{1a}$, $R^{1b}$, $R^{1c}$, and $R^{1d}$ is methyl.

In a further aspect, each of $R^{1b}$ and $R^{1d}$ is hydrogen, and each of $R^{1a}$ and $R^{1c}$ is independently methyl, ethyl, propyl, isopropyl, tert-butyl, sec-butyl, isobutyl, neopentyl, isopentyl, sec-pentyl, tert-pentyl, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(CH₂)(C=O)O(CH₂)₃CH₃, —(C=O)OCH₃, —(C=O)OCH₂CH₃, —(C=O)O(CH₂)₂CH₃, —(C=O)OCH(CH₃)₂, or —(C=O)O(CH₂)₃CH₃. In a still further aspect, each of $R^{1b}$ and $R^{1d}$ is hydrogen, and each of $R^{1a}$ and $R^{1c}$ is independently hydrogen, methyl, ethyl, propyl, isopropyl, tert-butyl, sec-butyl, isobutyl, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(CH₂)(C=O)O(CH₂)₃CH₃, —(C=O)OCH₃, —(C=O)OCH₂CH₃, —(C=O)O(CH₂)₂CH₃, or —(C=O)OCH(CH₃)₂. In a yet further aspect, each of $R^{1b}$ and $R^{1d}$ is hydrogen, and each of $R^{1a}$ and $R^{1c}$ is independently hydrogen, methyl, ethyl, propyl, isopropyl, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(C=O)OCH₃, —(C=O)OCH₂CH₃, —(C=O)O(CH₂)₂CH₃, or —(C=O)OCH(CH₃)₂. In an even further aspect, each of $R^{1b}$ and $R^{1d}$ is hydrogen, and each of $R^{1a}$ and $R^{1c}$ is independently hydrogen, methyl, ethyl, —(CH₂)(C=O)OCH₃, —(CH₂)(C=O)OCH₂CH₃, —(C=O)OCH₃, or —(C=O)OCH₂CH₃. In a still further aspect, each of $R^{1b}$ and $R^{1d}$ is hydrogen, and each of $R^{1a}$ and $R^{1c}$ is independently hydrogen, methyl, —(CH₂)(C=O)OCH₃, or —(C=O)OCH₃.

In a further aspect, each of $R^{1b}$ and $R^{1d}$ is hydrogen, and each of $R^{1a}$ and $R^{1c}$ is independently hydrogen, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(CH₂)(C=O)O(CH₂)₃CH₃, —(C=O)OCH₃, —(C=O)OCH₂CH₃, —(C=O)O(CH₂)₂CH₃, —(C=O)OCH(CH₃)₂, or —(C=O)O(CH₂)₃CH₃. In a still further aspect, each of $R^{1b}$ and $R^{1d}$ is hydrogen, and each of $R^{1a}$ and $R^{1c}$ is independently hydrogen, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(CH₂)(C=O)O(CH₂)₃CH₃, —(C=O)OCH₃, —(C=O)OCH₂CH₃, —(C=O)O(CH₂)₂CH₃, —(C=O)OCH(CH₃)₂, or —(C=O)O(CH₂)₃CH₃. In a yet further aspect, each of $R^{1b}$ and $R^{1d}$ is hydrogen, and each of $R^{1a}$ and $R^{1c}$ is independently hydrogen, —(CH₂)(C=O)OCH₃, —(CH₂)(C=O)OCH₂CH₃, —(CH₂)(C=O)O(CH₂)₂CH₃, —(CH₂)(C=O)OCH(CH₃)₂, —(C=O)OCH₃, —(C=O)OCH₂CH₃, —(C=O)O(CH₂)₂CH₃, or —(C=O)OCH(CH₃)₂. In an even further aspect, each of $R^{1b}$ and $R^{1d}$ is hydrogen, and each of $R^{1a}$ and $R^{1c}$ is independently hydrogen, —(CH₂)(C=O)OCH₃, —(CH₂)(C=O)OCH₂CH₃, —(C=O)OCH₃, or —(C=O)OCH₂CH₃. In a still further aspect, each of $R^{1b}$ and $R^{1d}$ is hydrogen, and each of $R^{1a}$ and $R^{1c}$ is independently hydrogen, —(CH₂)(C=O)OCH₃, or —(C=O)OCH₃.

In a further aspect, each of $R^{1b}$ and $R^{1d}$ is hydrogen, and each of $R^{1a}$ and $R^{1c}$ is independently hydrogen or C1-C6 alkyl. In a further aspect, each of $R^{1b}$ and $R^{1d}$ is hydrogen, and each of $R^{1a}$ and $R^{1c}$ is independently hydrogen, methyl, ethyl, propyl, isopropyl, tert-butyl, sec-butyl, isobutyl, neopentyl, isopentyl, sec-pentyl, or tert-pentyl. In a still further aspect, each of $R^{1b}$ and $R^{1d}$ is hydrogen, and each of $R^{1a}$ and $R^{1c}$ is independently hydrogen, methyl, ethyl, propyl, isopropyl, tert-butyl, sec-butyl, or isobutyl. In a yet further aspect, each of $R^{1b}$ and $R^{1d}$ is hydrogen, and each of $R^{1a}$ and $R^{1c}$ is independently hydrogen, methyl, ethyl, propyl, or isopropyl. In a yet further aspect, each of $R^{1b}$ and $R^{1d}$ is hydrogen, and each of $R^{1a}$ and $R^{1c}$ is independently methyl or ethyl. In a still further aspect, each of $R^{1b}$ and $R^{1d}$ is hydrogen, and each of $R^{1a}$ and $R^{1c}$ is independently hydrogen or methyl. In a yet further aspect, each of $R^{1b}$ and $R^{1d}$ is hydrogen, and each of $R^{1a}$ and $R^{1c}$ is methyl.

5. $R^2$ Group

In one aspect, $R^2$ is hydrogen, C1-C6 alkyl, aryl, or —(CH₂)n(C=O)OR¹²; $R^{12}$ is C1-C6 alkyl; and p is an integer selected from 0, 1, 2, and 3. In a further aspect, $R^2$ is hydrogen, C1-C6 alkyl, aryl, or —(CH₂)$_n$(C=O)OR¹²; $R^{12}$ is C1-C6 alkyl; and p is an integer selected from 0, 1, and 2. In a still further aspect, $R^2$ is hydrogen, C1-C6 alkyl, aryl, or —(CH₂)$_n$(C=O)OR¹²; $R^{12}$ is C1-C6 alkyl; and p is an integer selected from 0 and 1. In a still further aspect, $R^2$ is hydrogen, C1-C6 alkyl, aryl, or —(CH₂)(C=O)OR¹²; and $R^{12}$ is C1-C6 alkyl. In an even further aspect, $R^2$ is hydrogen, C1-C6 alkyl, aryl, or —(CH₂)₂(C=O)OR¹²; and $R^{12}$ is C1-C6 alkyl.

In a further aspect, $R^2$ is hydrogen, methyl, ethyl, propyl, isopropyl, tert-butyl, sec-butyl, isobutyl, neopentyl, isopentyl, sec-pentyl, tert-pentyl, phenyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, $R^2$ is hydrogen, methyl, ethyl, propyl, isopropyl, tert-butyl, sec-butyl, isobutyl, phenyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, $R^2$ is hydrogen, methyl, ethyl, propyl, isopropyl, phenyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, $R^2$ is hydrogen, methyl, ethyl, phenyl, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, $R^2$ is hydrogen, methyl, phenyl, —(CH$_2$)(C=O)OCH$_3$, or —(C=O)OCH$_3$.

In a further aspect, $R^2$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, $R^2$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, $R^2$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, $R^2$ is hydrogen, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, $R^2$ is hydrogen, —(CH$_2$)(C=O)OCH$_3$, or —(C=O)OCH$_3$.

In a further aspect, $R^2$ is hydrogen or C1-C6 alkyl. In a further aspect, $R^2$ is hydrogen, phenyl, methyl, ethyl, propyl, isopropyl, tert-butyl, sec-butyl, isobutyl, neopentyl, isopentyl, sec-pentyl, or tert-pentyl. In a still further aspect, $R^2$ is hydrogen, phenyl, methyl, ethyl, propyl, isopropyl, tert-butyl, sec-butyl, or isobutyl. In a yet further aspect, $R^2$ is hydrogen, phenyl, methyl, ethyl, propyl, or isopropyl. In a yet further aspect, $R^2$ is phenyl, methyl or ethyl. In a still further aspect, $R^2$ is hydrogen, phenyl, or methyl. In a yet further aspect, $R^2$ is hydrogen or phenyl. In an even further aspect, $R^2$ is methyl or phenyl.

In a further aspect, $R^2$ is hydrogen or C1-C6 alkyl. In a further aspect, $R^2$ is hydrogen, methyl, ethyl, propyl, isopropyl, tert-butyl, sec-butyl, isobutyl, neopentyl, isopentyl, sec-pentyl, or tert-pentyl. In a still further aspect, $R^2$ is hydrogen, methyl, ethyl, propyl, isopropyl, tert-butyl, sec-butyl, or isobutyl. In a yet further aspect, $R^2$ is hydrogen, methyl, ethyl, propyl, or isopropyl. In a yet further aspect, $R^2$ is methyl or ethyl. In a still further aspect, $R^2$ is hydrogen or methyl. In a yet further aspect, $R^2$ is hydrogen. In an even further aspect, $R^2$ is methyl.

6. $R^3$ Group

In one aspect, $R^3$ is hydrogen, C1-C6 alkyl, aryl, trimethylsilyl, or —(CH$_2$)$_r$(C=O)OR$^{15}$; $R^{15}$ is C1-C6 alkyl; and r is an integer selected from 0, 1, 2, and 3. In a further aspect, $R^3$ is hydrogen, C1-C6 alkyl, aryl, trimethylsilyl, or —(CH$_2$)$_r$(C=O)OR$^{15}$; $R^{15}$ is C1-C6 alkyl; and r is an integer selected from 0, 1, and 2. In a still further aspect, $R^3$ is hydrogen, C1-C6 alkyl, aryl, trimethylsilyl, or —(CH$_2$)$_r$(C=O)OR$^{15}$; $R^{15}$ is C1-C6 alkyl; and r is an integer selected from 0 and 1. In a still further aspect, $R^3$ is hydrogen, C1-C6 alkyl, aryl, trimethylsilyl, or —(CH$_2$)(C=O)OR$^{15}$; and $R^{15}$ is C1-C6 alkyl. In an even further aspect, $R^3$ is hydrogen, C1-C6 alkyl, aryl, trimethylsilyl, or —(CH$_2$)$_2$(C=O)OR$^{15}$; and $R^{15}$ is C1-C6 alkyl.

In a further aspect, $R^3$ is hydrogen, methyl, ethyl, propyl, isopropyl, tert-butyl, sec-butyl, isobutyl, neopentyl, isopentyl, sec-pentyl, tert-pentyl, phenyl, trimethylsilyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, $R^3$ is hydrogen, methyl, ethyl, propyl, isopropyl, tert-butyl, sec-butyl, isobutyl, phenyl, trimethylsilyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, $R^3$ is hydrogen, methyl, ethyl, propyl, isopropyl, phenyl, trimethylsilyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, $R^3$ is hydrogen, methyl, ethyl, phenyl, trimethylsilyl, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, $R^3$ is hydrogen, methyl, phenyl, trimethylsilyl, —(CH$_2$)(C=O)OCH$_3$, or —(C=O)OCH$_3$.

In a further aspect, $R^3$ is hydrogen, methyl, ethyl, propyl, isopropyl, tert-butyl, sec-butyl, isobutyl, neopentyl, isopentyl, sec-pentyl, tert-pentyl, phenyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, $R^3$ is hydrogen, methyl, ethyl, propyl, isopropyl, tert-butyl, sec-butyl, isobutyl, phenyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, $R^3$ is hydrogen, methyl, ethyl, propyl, isopropyl, phenyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, $R^3$ is hydrogen, methyl, ethyl, phenyl, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, $R^3$ is hydrogen, methyl, phenyl, —(CH$_2$)(C=O)OCH$_3$, or —(C=O)OCH$_3$.

In a further aspect, $R^3$ is hydrogen, trimethylsilyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, $R^3$ is hydrogen, trimethylsilyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)

(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^3$ is hydrogen, trimethylsilyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^3$ is hydrogen, trimethylsilyl, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, R$^3$ is hydrogen, —(CH$_2$)(C=O)OCH$_3$, or —(C=O)OCH$_3$.

In a further aspect, R$^3$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^3$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^3$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^3$ is hydrogen, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, R$^3$ is hydrogen, —(CH$_2$)(C=O)OCH$_3$, or —(C=O)OCH$_3$.

In a further aspect, R$^3$ is hydrogen, trimethylsilyl, or C1-C6 alkyl. In a further aspect, R$^3$ is hydrogen, trimethylsilyl, phenyl, methyl, ethyl, propyl, isopropyl, tert-butyl, sec-butyl, isobutyl, neopentyl, isopentyl, sec-pentyl, or tert-pentyl. In a still further aspect, R$^3$ is hydrogen, trimethylsilyl, phenyl, methyl, ethyl, propyl, isopropyl, tert-butyl, sec-butyl, or isobutyl. In a yet further aspect, R$^3$ is hydrogen, trimethylsilyl, phenyl, methyl, ethyl, propyl, or isopropyl. In a yet further aspect, R$^3$ is phenyl, methyl or ethyl. In a still further aspect, R$^3$ is hydrogen, trimethylsilyl, phenyl, or methyl. In a yet further aspect, R$^3$ is hydrogen, trimethylsilyl, or phenyl. In an even further aspect, R$^3$ is methyl, trimethylsilyl, or phenyl.

7. R$^{10}$ Group

In one aspect, R$^{10}$ is C1-C6 alkyl. In a further aspect, R$^{10}$ is methyl, ethyl, propyl, isopropyl, tert-butyl, sec-butyl, isobutyl, neopentyl, isopentyl, sec-pentyl, or tert-pentyl. In a still further aspect, R$^{10}$ is methyl, ethyl, propyl, isopropyl, tert-butyl, sec-butyl, or isobutyl. In a yet further aspect, R$^{10}$ is methyl, ethyl, propyl, or isopropyl. In a yet further aspect, R$^{10}$ is methyl or ethyl. In a still further aspect, R$^{10}$ is methyl.

8. R$^{11}$ Group

In one aspect, R$^{11}$ is C1-C6 alkyl. In a further aspect, R$^{11}$ is methyl, ethyl, propyl, isopropyl, tert-butyl, sec-butyl, isobutyl, neopentyl, isopentyl, sec-pentyl, or tert-pentyl. In a still further aspect, R$^{11}$ is methyl, ethyl, propyl, isopropyl, tert-butyl, sec-butyl, or isobutyl. In a yet further aspect, R$^{11}$ is methyl, ethyl, propyl, or isopropyl. In a yet further aspect, R$^{11}$ is methyl or ethyl. In a still further aspect, R$^{11}$ is methyl.

9. R$^{12}$ Group

In one aspect, R$^{12}$ is C1-C6 alkyl. In a further aspect, R$^{12}$ is methyl, ethyl, propyl, isopropyl, tert-butyl, sec-butyl, isobutyl, neopentyl, isopentyl, sec-pentyl, or tert-pentyl. In a still further aspect, R$^{12}$ is methyl, ethyl, propyl, isopropyl, tert-butyl, sec-butyl, or isobutyl. In a yet further aspect, R$^{12}$ is methyl, ethyl, propyl, or isopropyl. In a yet further aspect, R$^{12}$ is methyl or ethyl. In a still further aspect, R$^{12}$ is methyl.

10. R$^{14}$ Group

In one aspect, R$^{14}$ is C1-C6 alkyl. In a further aspect, R$^{14}$ is methyl, ethyl, propyl, isopropyl, tert-butyl, sec-butyl, isobutyl, neopentyl, isopentyl, sec-pentyl, or tert-pentyl. In a still further aspect, R$^{14}$ is methyl, ethyl, propyl, isopropyl, tert-butyl, sec-butyl, or isobutyl. In a yet further aspect, R$^{14}$ is methyl, ethyl, propyl, or isopropyl. In a yet further aspect, R$^{14}$ is methyl or ethyl. In a still further aspect, R$^{14}$ is methyl.

11. R$^{15}$ Group

In one aspect, R$^{15}$ is C1-C6 alkyl. In a further aspect, R$^{15}$ is methyl, ethyl, propyl, isopropyl, tert-butyl, sec-butyl, isobutyl, neopentyl, isopentyl, sec-pentyl, or tert-pentyl. In a still further aspect, R$^{15}$ is methyl, ethyl, propyl, isopropyl, tert-butyl, sec-butyl, or isobutyl. In a yet further aspect, R$^{15}$ is methyl, ethyl, propyl, or isopropyl. In a yet further aspect, R$^{15}$ is methyl or ethyl. In a still further aspect, R$^{15}$ is methyl.

12. R$^{20}$ Group

In one aspect, R$^{20}$ is hydrogen, C1-C6 alkyl, or —(CH$_2$)$_p$(C=O)OR$^{30}$; R$^{30}$ is C1-C6 alkyl; and p is an integer selected from 0, 1, 2, and 3. In a further aspect, R$^{20}$ is hydrogen, C1-C6 alkyl, or —(CH$_2$)$_p$(C=O)OR$^{30}$; R$^{30}$ is C1-C6 alkyl; and p is an integer selected from 0, 1, and 2. In a still further aspect, R$^{20}$ is hydrogen, C1-C6 alkyl, or —(CH$_2$)$_p$(C=O)OR$^{30}$; R$^{30}$ is C1-C6 alkyl; and p is an integer selected from 0 and 1. In a still further aspect, R$^{20}$ is hydrogen, C1-C6 alkyl, or —(CH$_2$)(C=O)OR$^{30}$; and R$^{30}$ is C1-C6 alkyl. In an even further aspect, R$^{20}$ is hydrogen, C1-C6 alkyl, or —(CH$_2$)$_2$(C=O)OR$^{30}$; and R$^{30}$ is C1-C6 alkyl.

In a further aspect, R$^{20}$ is hydrogen, methyl, ethyl, propyl, isopropyl, tert-butyl, sec-butyl, isobutyl, neopentyl, isopentyl, sec-pentyl, tert-pentyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^{20}$ is hydrogen, methyl, ethyl, propyl, isopropyl, tert-butyl, sec-butyl, isobutyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^{20}$ is hydrogen, methyl, ethyl, propyl, isopropyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^{20}$ is hydrogen, methyl, ethyl, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, R$^{20}$ is hydrogen, methyl, —(CH$_2$)(C=O)OCH$_3$, or —(C=O)OCH$_3$.

In a further aspect, R$^{20}$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^{20}$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^{20}$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^{20}$ is hydrogen, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, R$^{20}$ is hydrogen, —(CH$_2$)(C=O)OCH$_3$, or —(C=O)OCH$_3$.

In a further aspect, R$^{20}$ is hydrogen or C1-C6 alkyl. In a further aspect, R$^{20}$ is hydrogen, methyl, ethyl, propyl, isopropyl, tert-butyl, sec-butyl, isobutyl, neopentyl, isopentyl, sec-pentyl, or tert-pentyl. In a still further aspect, R$^{20}$ is hydrogen, methyl, ethyl, propyl, isopropyl, tert-butyl, sec-butyl, or isobutyl. In a yet further aspect, R$^{20}$ is hydrogen, methyl, ethyl, propyl, or isopropyl. In a yet further aspect, R$^{20}$ is methyl or ethyl. In a still further aspect, R$^{20}$ is hydrogen or methyl. In a yet further aspect, R$^{20}$ is hydrogen. In an even further aspect, R$^{20}$ is methyl.

13. R$^{21}$ Group

In one aspect, R$^{21}$ is hydrogen, C1-C6 alkyl, or —(CH$_2$)$_q$(C=O)OR$^{31}$; R$^{31}$ is C1-C6 alkyl; and q is an integer selected from 0, 1, 2, and 3. In a further aspect, R$^{21}$ is hydrogen, C1-C6 alkyl, or —(CH$_2$)$_q$(C=O)OR$^{31}$; R$^{31}$ is C1-C6 alkyl; and q is an integer selected from 0, 1, and 2. In a still further aspect, R$^{21}$ is hydrogen, C1-C6 alkyl, or —(CH$_2$)$_q$(C=O)OR$^{31}$; R$^{31}$ is C1-C6 alkyl; and q is an integer selected from 0 and 1. In a still further aspect, R$^{21}$ is hydrogen, C1-C6 alkyl, or —(CH$_2$)(C=O)OR$^{31}$; and R$^{31}$ is C1-C6 alkyl. In an even further aspect, R$^{21}$ is hydrogen, C1-C6 alkyl, or —(CH$_2$)$_2$(C=O)OR$^{31}$; and R$^{31}$ is C1-C6 alkyl.

In a further aspect, R$^{21}$ is hydrogen, methyl, ethyl, propyl, isopropyl, tert-butyl, sec-butyl, isobutyl, neopentyl, isopentyl, sec-pentyl, tert-pentyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^{21}$ is hydrogen, methyl, ethyl, propyl, isopropyl, tert-butyl, sec-butyl, isobutyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^{21}$ is hydrogen, methyl, ethyl, propyl, isopropyl, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^{21}$ is hydrogen, methyl, ethyl, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, R$^{21}$ is hydrogen, methyl, —(CH$_2$)(C=O)OCH$_3$, or —(C=O)OCH$_3$.

In a further aspect, R$^{21}$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(CH$_2$)(C=O)O(CH$_2$)$_3$CH$_3$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^{21}$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^{21}$ is hydrogen, —(CH$_2$)(C=O)OCH$_3$, —(CH$_2$)(C=O)OCH$_2$CH$_3$, —(CH$_2$)(C=O)O(CH$_2$)$_2$CH$_3$, —(CH$_2$)(C=O)OCH(CH$_3$)$_2$, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^{21}$ is hydrogen, —(CH$_2$)(C=O)OCH$_3$, —(CH$_2$)(C=O)OCH$_2$CH$_3$, —(C=O)OCH$_3$, or —(C=O)OCH$_2$CH$_3$. In a still further aspect, R$^{21}$ is hydrogen, —(CH$_2$)(C=O)OCH$_3$, or —(C=O)OCH$_3$.

In a further aspect, R$^{21}$ is hydrogen or C1-C6 alkyl. In a further aspect, R$^{21}$ is hydrogen, methyl, ethyl, propyl, isopropyl, tert-butyl, sec-butyl, isobutyl, neopentyl, isopentyl, sec-pentyl, or tert-pentyl. In a still further aspect, R$^{21}$ is hydrogen, methyl, ethyl, propyl, isopropyl, tert-butyl, sec-butyl, or isobutyl. In a yet further aspect, R$^{21}$ is hydrogen, methyl, ethyl, propyl, or isopropyl. In a yet further aspect, R$^{21}$ is methyl or ethyl. In a still further aspect, R$^{21}$ is hydrogen or methyl. In a yet further aspect, R$^{21}$ is hydrogen. In an even further aspect, R$^{21}$ is methyl.

14. R$^{22}$ Group

In one aspect, R$^{22}$ is C1-C6 alkyl or —(C=O)OR$^{32}$; and R$^{32}$ is C1-C6 alkyl.

In a further aspect, R$^{22}$ is methyl, ethyl, propyl, isopropyl, tert-butyl, sec-butyl, isobutyl, neopentyl, isopentyl, sec-pentyl, tert-pentyl, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^{22}$ is methyl, ethyl, propyl, isopropyl, tert-butyl, sec-butyl, isobutyl, —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^{22}$ is methyl, ethyl, propyl, isopropyl, —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^{22}$ is methyl, ethyl, —(C=O)OCH$_3$, or —(C=O)OCH$_2$CH$_3$. In a still further aspect, R$^{22}$ is methyl or —(C=O)OCH$_3$.

In a further aspect, R$^{22}$ is —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a still further aspect, R$^{22}$ is —(C=O)OCH$_3$, —(C=O)OCH$_2$CH$_3$, —(C=O)O(CH$_2$)$_2$CH$_3$, —(C=O)OCH(CH$_3$)$_2$, or —(C=O)O(CH$_2$)$_3$CH$_3$. In a yet further aspect, R$^{22}$ is —(C=O)OCH$_3$, —(C=O)OCH$_2$CH$_3$, —(C=O)O(CH$_2$)$_2$CH$_3$, or —(C=O)OCH(CH$_3$)$_2$. In an even further aspect, R$^{22}$ is —(C=O)OCH$_3$, or —(C=O)OCH$_2$CH$_3$. In a still further aspect, R$^{22}$ is or —(C=O)OCH$_3$.

In a further aspect, R$^{22}$ is C1-C6 alkyl. In a further aspect, R$^{22}$ is methyl, ethyl, propyl, isopropyl, tert-butyl, sec-butyl, isobutyl, neopentyl, isopentyl, sec-pentyl, or tert-pentyl. In a still further aspect, R$^{22}$ is methyl, ethyl, propyl, isopropyl, tert-butyl, sec-butyl, or isobutyl. In a yet further aspect, R$^{22}$ is methyl, ethyl, propyl, or isopropyl. In a yet further aspect, R$^{22}$ is methyl or ethyl. In a still further aspect, R$^{22}$ is hydrogen or methyl. In a yet further aspect, R$^{22}$ is hydrogen. In an even further aspect, R$^{22}$ is methyl.

15. R$^{30}$ Group

In one aspect, R$^{30}$ is C1-C6 alkyl. In a further aspect, R$^{30}$ is methyl, ethyl, propyl, isopropyl, tert-butyl, sec-butyl, isobutyl, neopentyl, isopentyl, sec-pentyl, or tert-pentyl. In a still further aspect, $R^{30}$ is methyl, ethyl, propyl, isopropyl, tert-butyl, sec-butyl, or isobutyl. In a yet further aspect, $R^{30}$ is methyl, ethyl, propyl, or isopropyl. In a yet further aspect, $R^{30}$ is methyl or ethyl. In a still further aspect, $R^{30}$ is methyl.

16. $R^{31}$ Group

In one aspect, $R^{31}$ is C1-C6 alkyl. In a further aspect, $R^{31}$ is methyl, ethyl, propyl, isopropyl, tert-butyl, sec-butyl, isobutyl, neopentyl, isopentyl, sec-pentyl, or tert-pentyl. In a still further aspect, $R^{31}$ is methyl, ethyl, propyl, isopropyl, tert-butyl, sec-butyl, or isobutyl. In a yet further aspect, $R^{31}$ is methyl, ethyl, propyl, or isopropyl. In a yet further aspect, $R^{31}$ is methyl or ethyl. In a still further aspect, $R^{31}$ is methyl.

17. $R^{32}$ Group

In one aspect, $R^{32}$ is C1-C6 alkyl. In a further aspect, $R^{32}$ is methyl, ethyl, propyl, isopropyl, tert-butyl, sec-butyl, isobutyl, neopentyl, isopentyl, sec-pentyl, or tert-pentyl. In a still further aspect, $R^{32}$ is methyl, ethyl, propyl, isopropyl, tert-butyl, sec-butyl, or isobutyl. In a yet further aspect, $R^{32}$ is methyl, ethyl, propyl, or isopropyl. In a yet further aspect, $R^{32}$ is methyl or ethyl. In a still further aspect, $R^{32}$ is methyl.

18. Example Structures

In one aspect, an allenyne precursor compound can be present as:

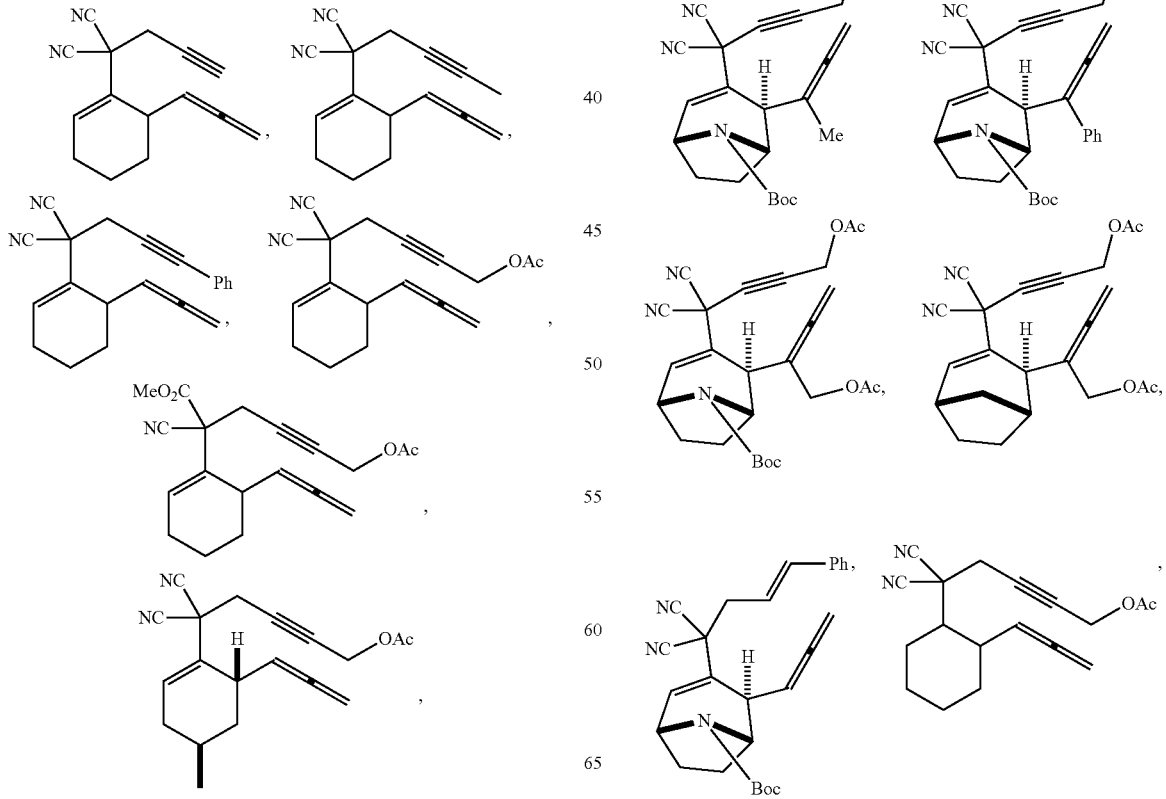

-continued

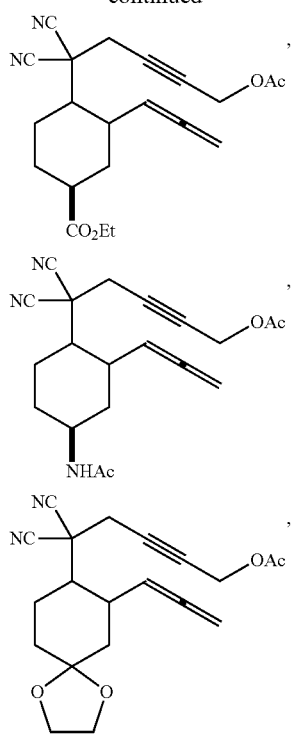

or a subgroup thereof.

In one aspect, a terpenoid scaffold compound can be present as:

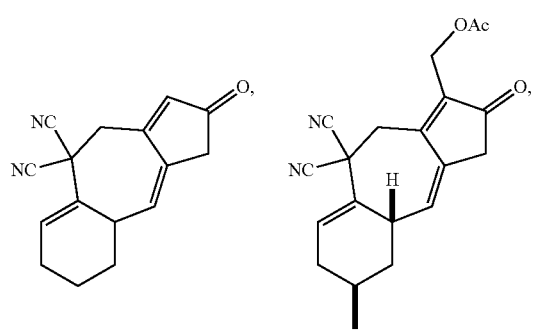

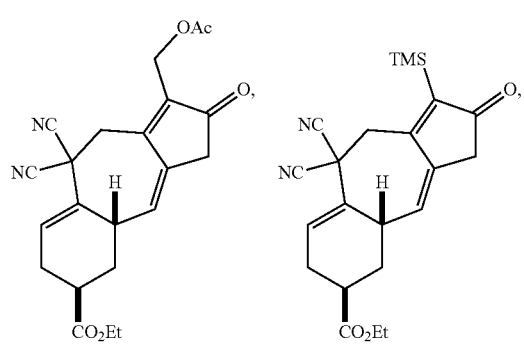

-continued

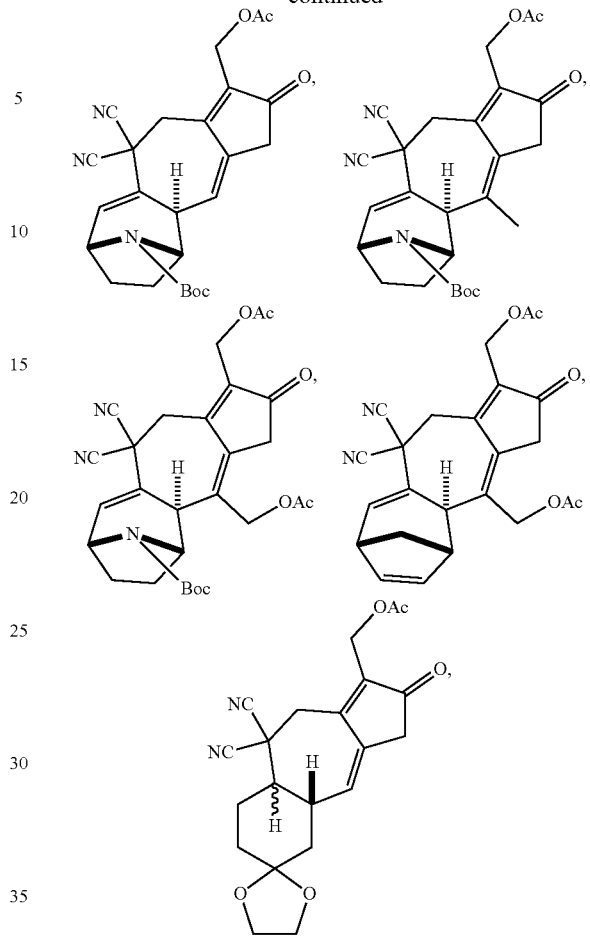

or a subgroup thereof.

C. METHODS OF MAKING THE DISCLOSED COMPOUNDS

In one aspect, the present disclosure relates to methods of making compounds useful in the preparation of intermediates for synthesis of terpenoid scaffolds, which can be useful in the development of therapeutic compounds utilizing such chemical backbones. In one aspect, the disclosure relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the disclosure comprises a pharmaceutical composition comprising a therapeutically effective amount of the product of the disclosed methods and a pharmaceutically acceptable carrier. In a still further aspect, the disclosure comprises a method for manufacturing a medicament comprising combining at least one compound of any of disclosed compounds or at least one product of the disclosed methods with a pharmaceutically acceptable carrier or diluent.

The compounds of this disclosure can be prepared by employing reactions as shown in the disclosed schemes, in addition to other standard manipulations that are known in the literature, exemplified in the experimental sections or clear to one skilled in the art. The following examples are provided so that the disclosure might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

In one aspect, the terpenoid scaffolds of the present disclosure can be prepared generically by the synthetic scheme as shown below. Compounds are represented in generic form, with substituents as noted in compound descriptions elsewhere herein.

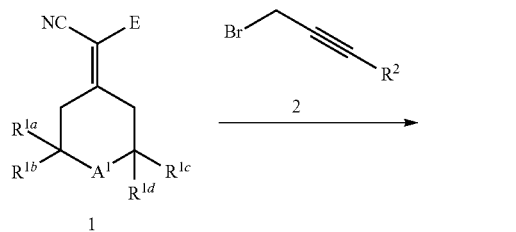

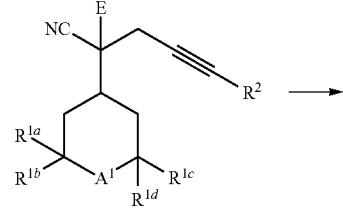

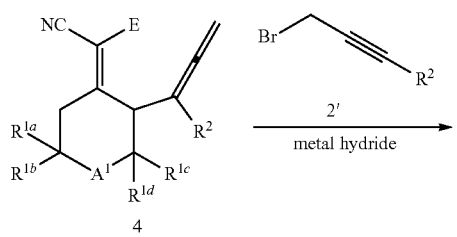

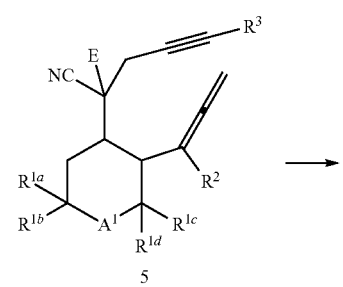

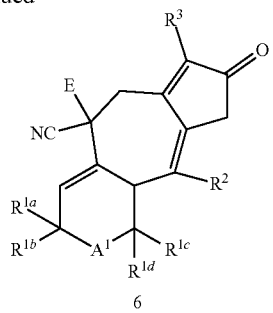

A more specific example of the procedure for the Knoevenagel condensation reaction step is set forth below.

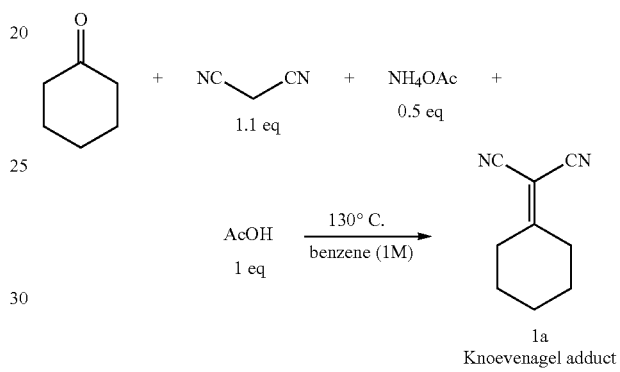

A suitable Knoevenagel adduct, such as compound 1a, can be prepared by reaction shown above. Briefly, a suitable ketone, a suitable malononitrile derivative (about 1 to about 2 equivalents), ammonium acetate (about 0.1 to about 1 equivalents), and acetic acid (1 equivalent) as shown above. The foregoing reactants are dissolved in a suitable solvent, e.g., benzene, (about 0.1 M to about 2.0 M with respect to the ketone) and refluxed at a suitable temperature, e.g., about 100° C. to about 200° C., in a suitable apparatus, e.g., using a Dean-Stark apparatus. When the ketone is fully consumed (monitored by TLC, 4-16 hours), the reaction mixture is cooled to room temperature and solvent is evaporated. The crude product can be further isolated by methods known to one skilled in the art, e.g., filtration and concentration, such as filteration through a silica plug and then concentrated under vacuum. The pure product, e.g., such as 1a in the above reaction scheme, can be further purified using methods known to one skilled in the art, e.g., column chromatography.

A more specific example of the procedure for the decojugative α-alkylation reaction step is set forth below.

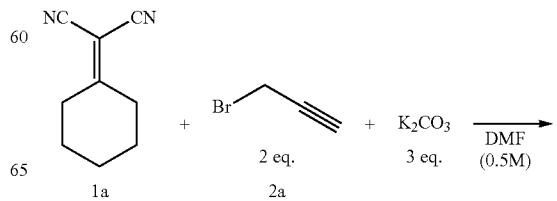

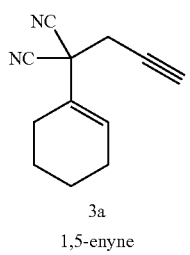

3a
1,5-enyne

A suitable 1,5-enyne, such as compound 3a, can be prepared using a suitable Knoevenagel adduct, such as 1a, prepared by the preceding method. Briefly, the Knoevenagel adduct and a suitable propargyl derivative (about 1 equivalent to about 3 equivalents), such as 2a, are dissolved in suitable solvent, e.g. anhydrous DMF, (about 0.1 M to about 1.0 M with respect to the limiting reagent). Finely ground $K_2CO_3$ (about 2 equivalents to about 4 equivalents) is then added to the solution and stirred at a suitable temperature, e.g. about room temperature, until the limiting reagent is consumed (monitored by TLC; 30 min-2 hrs.). The crude product can be further isolated by methods known to one skilled in the art, e.g., the solution can be diluted with a suitable solvent, e.g., EtOAc, and washed with a suitable solvent, e.g., water, about 3-7 times. The organic layer can then be washed with brine and dried, e.g., using $Na_2SO_4$, followed by removal of the solvent, e. g, under reduced pressure. The crude material further purified using methods known to one skilled in the art, e.g., via column chromatography.

A more specific example of the procedure for the one-pot Cope/α-alkylation reaction step is set forth below.

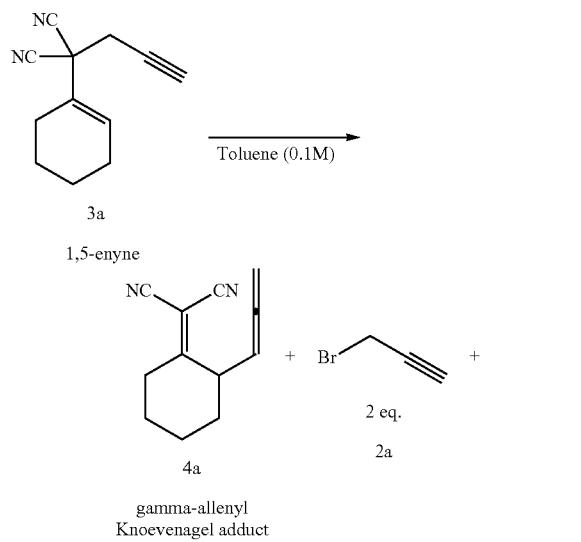

5aa
Allenyne precursor

A suitable allenyne precursor, such as compound 5aa, can be prepared using a suitable 1,5-enyne, such as 3a, prepared using the preceding methods. Briefly, the 1,5-enyne is dissolved in a suitable solvent, e.g., toluene, and an inert gas, e.g., $N_2$, is bubbled through the solution for a suitable period of time, e.g., about 1-10 minutes. The solution is then heated, e.g., using a pre-heated pie-block or oil bath in a screw cap pressure flask for a suitable period of time and at a suitable temperature, e.g., about 100° C. to about 250° C. for about 0.5 hours to about 8 hours. When the reaction is completed (e.g., as determined by monitoring reaction progress using TLC or another suitable means), the solution is cooled to a suitable temperature, e.g., about room temperature, and the solvent removed, e.g., under reduced pressure. The percent conversion can be calculated using $^1$H NMR, and this data can be utilized to determine the stoichiometry for the propargylation step. The crude product from the Cope rearrangement can be re-dissolved in a suitable solvent, e.g., THF (about 0.1 M to about 1.0 M with respect to allene 4a) and added to a suspension of a metal hydride, e.g., NaH (about 0.5 equivalent to about 2 equivalents) in a suitable solvent, e.g., THF, at a suitable temperature, e.g., about −5° C. to about 10° C. A suitable propargyl derivative, e.g., compound 2a, is then immediately added to the solution and the reaction was warmed to a suitable temperature, e.g., about 20° C. to about 30° C. Upon completion of the reaction (e.g., as determined by monitoring reaction progress using TLC or another suitable means), a suitable neutralizing solution, e.g., saturated solution of $NH_4Cl$, is added to quench the NaH. The crude material can be isolated by suitable means know to one skilled in the art, e.g., taken up in a suitable solvent, such as ethyl acetate, washed with $H_2O$ and brine, dried with $Na_2SO_4$, and concentrated under reduced pressure. The compound can be further purified by means know to one skilled in the art, e.g., column chromatography. In general, the gamma-allenyl Knoevenagel adduct is not isolated during preparation, and used directly in the next reaction step shown above.

Alternatively, suitable allenyne precursors can be prepared from suitable 1,5-enynes using a procedure for one-pot Cope/alkylidene reduction/α-alkylation reaction, a more specific example of which is set forth below.

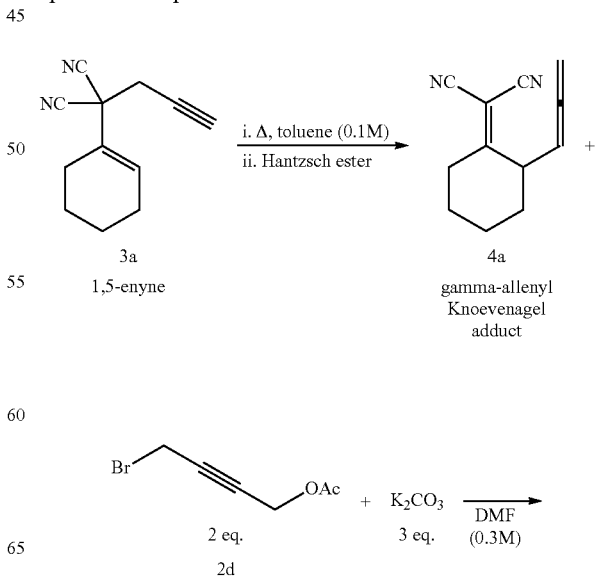

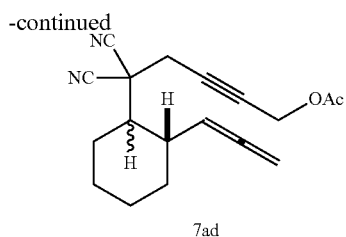

7ad

A suitable allenyne precursor, such as compound 7ad, can be prepared using a suitable 1,5-enyne, such as 3a, prepared using the preceding methods. Briefly, the 1,5-enyne is dissolved in a suitable solvent, e.g., toluene, and Hantzsch ester (about 1 to about 3 equivalents) are added. The solution is heated to a suitable temperature for a suitable period of time, e.g., about 100° C. to about 200° C. for about 4 hours to about 24 hours, using a suitable apparatus, e.g., a pre-heated pie-block in a screw cap pressure flask. When the reaction is completed (e.g., as determined by monitoring reaction progress using TLC or another suitable means), the solution is cooled to a suitable temperature, e.g., about room temperature, and the solvent removed, e.g., under reduced pressure. The crude product from the Cope rearrangement is re-dissolved in a suitable solvent, e.g., DMF (about 0.1 M to about 1.0 M with respect to allene 4a), and added to a suspension of a suitable base, e.g., $K_2CO_3$ (about 2 to about 4 equivalents), in a suitable solvent, e.g., DMF. A suitable propargyl derivative, e.g., compound 2d, is immediately added to the solution and the reaction was warmed to suitable temperature, e.g., about 20° C. to about 30° C. Upon completion of the reaction (e.g., as determined by monitoring reaction progress using TLC or another suitable means), crude material can be isolated by suitable means know to one skilled in the art, e.g., taken up in a suitable solvent, such as ethyl acetate, washed with $H_2O$ and brine, dried with $Na_2SO_4$, and concentrated under reduced pressure. The compound can be further purified by means know to one skilled in the art, e.g., column chromatography.

A more specific example of the procedure for the Pauson-Khand reaction step is set forth below.

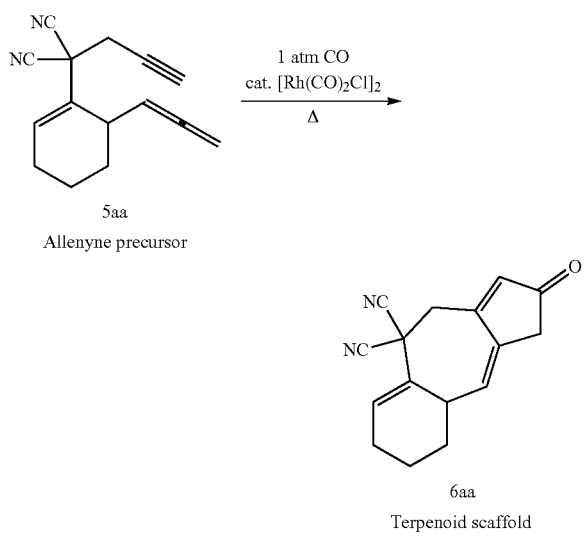

A suitable terpenoid scaffold, such as compound 6aa, can be prepared from a suitable allenyne precursor, such as compound 5aa, using a Pauson-Khand reaction. Briefly, a flame-dried Schlenk flask is charged with 5 mol % $[Rh(CO)_2Cl]_2$ and the flask evacuated, then refilled with CO gas. The allenyne precursor in a suitable solvent, e.g., toluene (0.01 M with respect to 5aa), are added to the flask and a full balloon of CO gas is bubbled through the solution. The balloon is replaced with a second full balloon of CO gas and the reaction heated at a suitable temperature, e.g., about 70° C. to about 150° C. When the reaction is completed (e.g., as determined by monitoring reaction progress using TLC or another suitable means), the solution is cooled to a suitable temperature, e.g., room temperature, and solvent can be removed, e.g., reduced pressure. The compound can be further purified by means know to one skilled in the art, e.g., column chromatography.

Alternatively, a flame-dried Schlenk flask can be charged with a solution of the allenyne in a suitable solvent, e.g., p-xylenes (0.005 M with respect to the allenyne precursor) under nitrogen. A full balloon of CO is bubbled through the solution before being replaced with a second balloon of CO. The $[Rh(CO)_2Cl]_2$ catalyst (10 mol %) is added to the reaction under an atmosphere of CO gas. The reaction is heated at a suitable temperature, e.g., about 90° C. to about 200° C., using a suitable apparatus, e.g., a preheated oil bath. When the reaction is completed (e.g., as determined by monitoring reaction progress using TLC or another suitable means), the solution is cooled to a suitable temperature, e.g., room temperature, and solvent can be removed, e.g., reduced pressure. The compound can be further purified by means know to one skilled in the art, e.g., column chromatography.

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Exemplary Disclosed Compounds

Figure 3A:
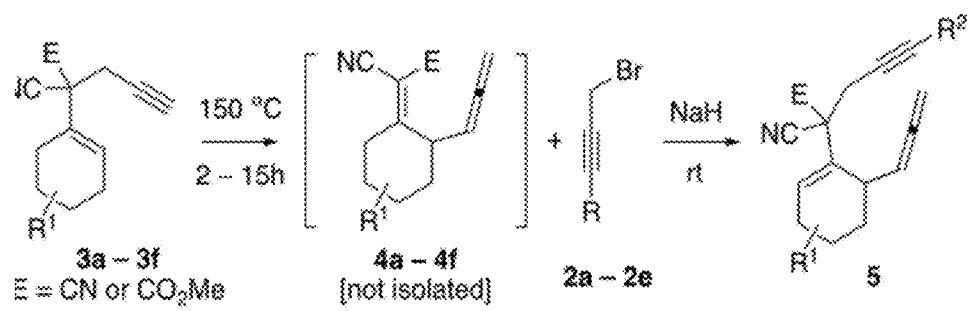
FIGS. 3A-3B show representative disclosed syntheses for the preparation of 1,7-allenynes.
Figure 3B:
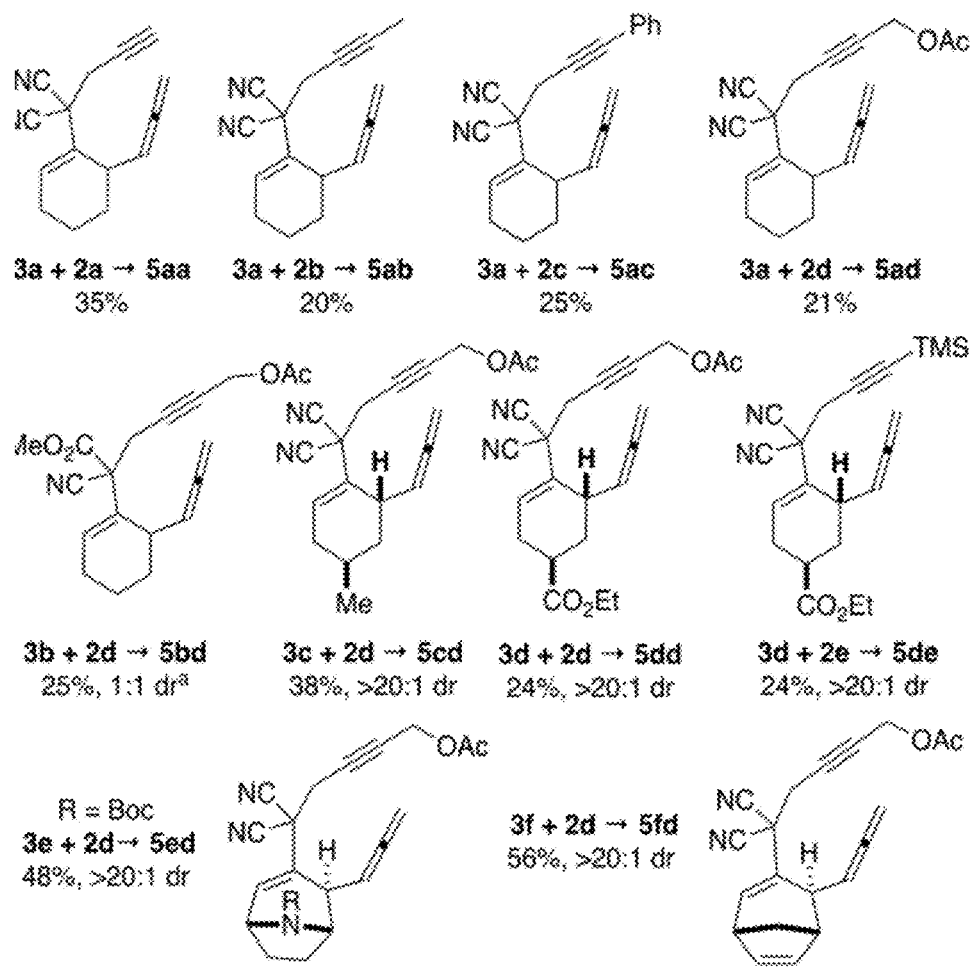
Figure 4A:
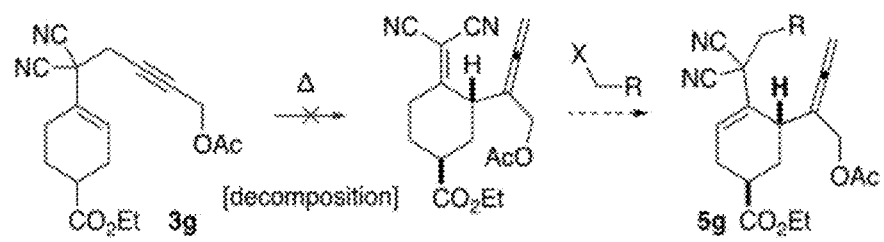
FIGS. 4A-4C show representative reaction sequences for 1,5-enynes that either do or do not undergo [3,3] rearrangement.
Figure 4B:
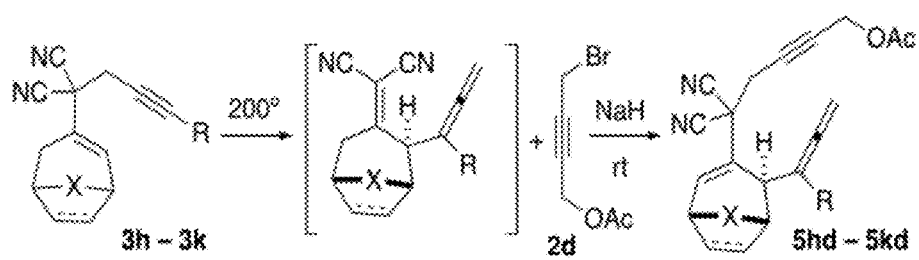
Figure 4C:
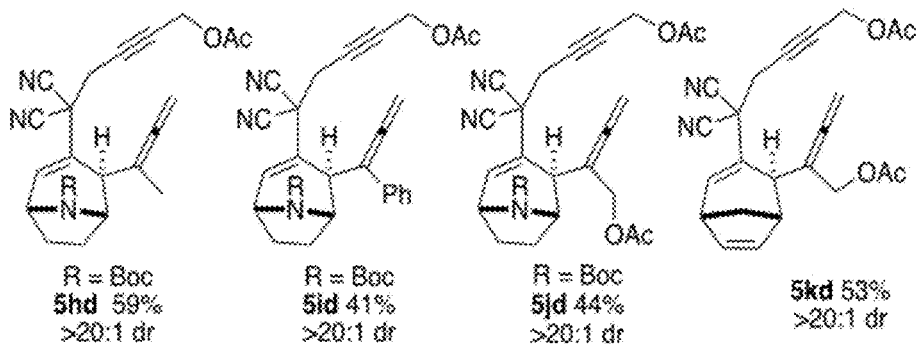
Figure 5A:
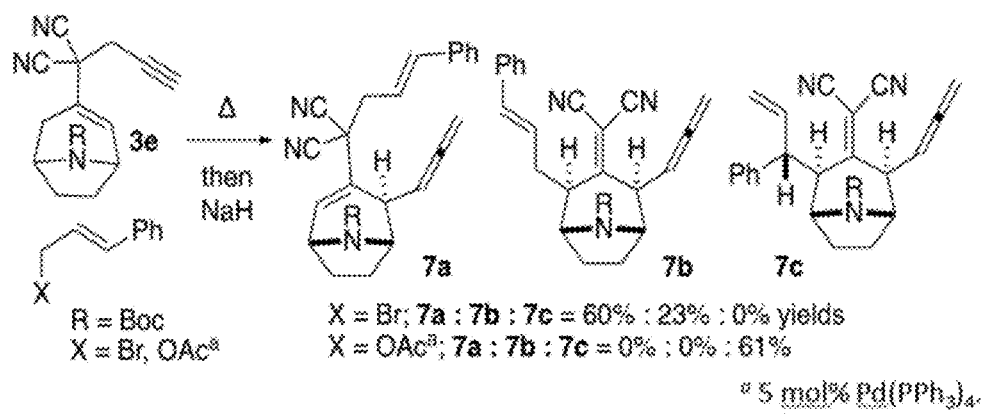
FIGS. 5A-5C show representative disclosed syntheses for the preparation of various allene/tethered π-systems prepared using the disclosed methods.
Figure 5B:
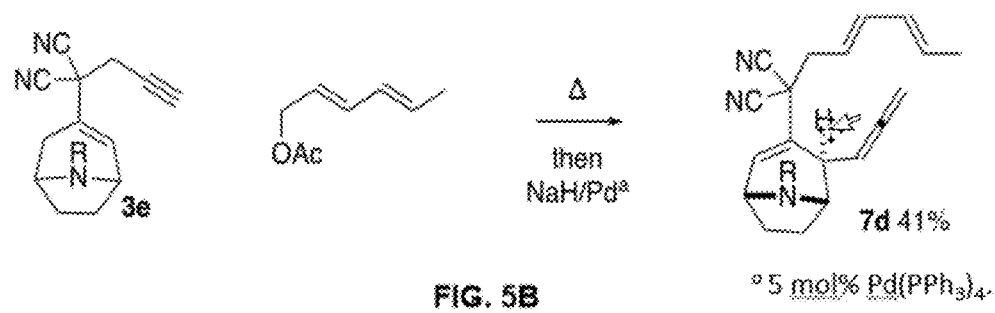
Figure 5C:
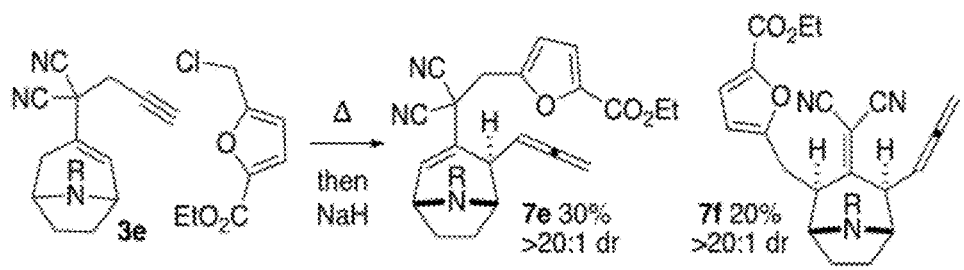
Figure 6A:
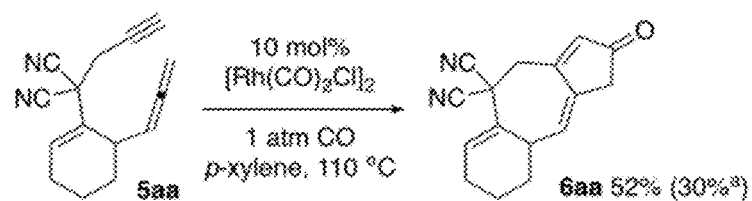
FIGS. 6A-6B show representative disclosed syntheses for the preparation of 6/7/5 tricycloalkane frameworks.
Figure 6B:
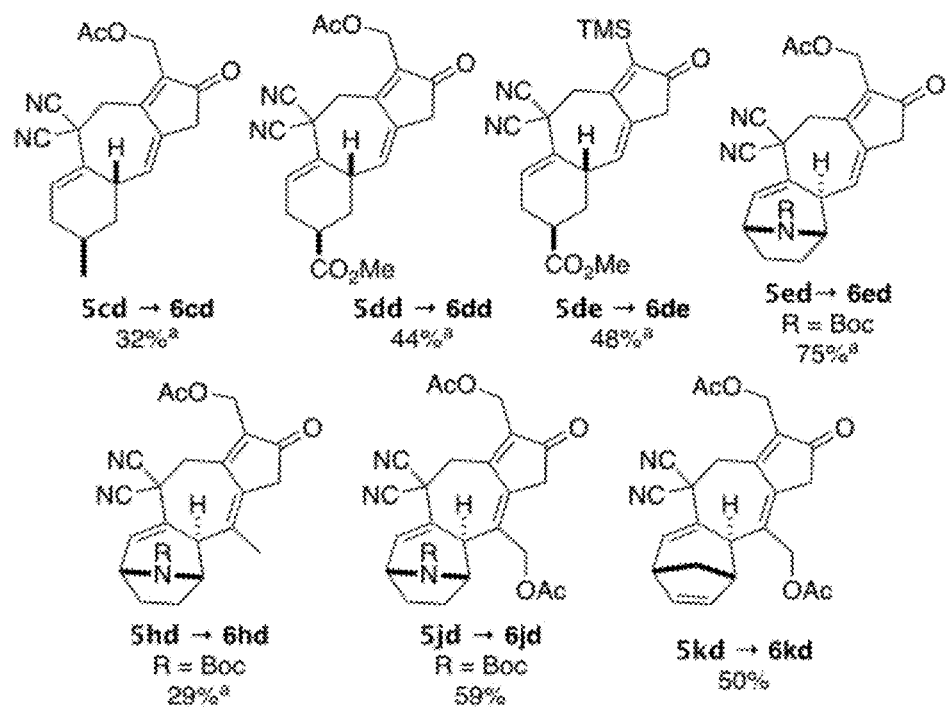

Exemplary disclosed compounds, and the associated reaction schemes, are shown in FIGS. 3A-8B. In the figures, exemplary compounds are shown as products of various reactions using compound labels or identifiers. The correlation of particular compound labels or identifiers with structure, and the reactants used to prepare same, are specified in Tables 1-8 below. For example, FIG. 3A shows a generalized reaction scheme for reaction of compounds 3a-3f to yield compounds 4a-4, which was not isolated, but used in reaction directly with compounds 2a-2f to give the desired products 5aa-5fd shown in FIG. 3B. For example, FIG. 3B shows a particular compound, 5aa, which is indicated as having been prepared from reactants 3a and 2a. Yields and particular notes are given for each compound shown. General reaction details for each figure is noted above in the Brief Description of the Figures. The other figures are to be understood as explained for the particular figures and examples referenced above for FIGS. 3A and 3B. Further experimental details are provided herein below.

TABLE 1

Knoevenagel Adducts.

| Compound Identifier | Structure | Reactants |
|---|---|---|
| 1a | [NC, CN cyclohexylidene] | [cyclohexanone], NCCH$_2$CN |
| 1b | [NC, CO$_2$Me cyclohexylidene] | [cyclohexanone], NCCH$_2$(C=O)OCH$_3$ |
| 1c | [NC, CN 4-methylcyclohexylidene] | [4-methylcyclohexanone], NCCH$_2$CN |
| 1d | [NC, CN cyclohexylidene with CO$_2$Et] | [cyclohexanone with CO$_2$Et], NCCH$_2$CN |
| 1e | [NC, CN bicyclic with N-R] R = Boc | [ketone with N-R], NCCH$_2$CN, R = Boc |
| 1f | [NC, CN bicyclic alkene] | [bicyclic ketone], NCCH$_2$CN |
| 1l | [NC, CN cyclohexylidene with NHAc] | [cyclohexanone with NHAc], NCCH$_2$CN |
| 1m | [NC, CN cyclohexylidene with dioxolane] | [cyclohexanone with dioxolane], NCCH$_2$CN |

TABLE 2

Propargyl Derivatives.

| Compound Identifier | Structure | Reactants |
|---|---|---|
| 2 | HO–⎯≡⎯–OAc | HO–⎯≡⎯–OH, Ac$_2$O |
| 2a | Br–⎯≡ | Commercially available |
| 2b | Br–⎯–≡ | Commercially available |

TABLE 2-continued

Propargyl Derivatives.

| Compound Identifier | Structure | Reactants |
|---|---|---|
| 2c | Br-CH₂-C≡C-Ph | HO-CH₂-C≡C-Ph, PBr₃ |
| 2d | Br-CH₂-C≡C-CH₂-OAc | HO-CH₂-C≡C-CH₂-OAc, CBr₄, PBr₃ |
| 2e | Br-CH₂-C≡C-TMS | Commercially available |
| 2f | AcO-CH₂-CH=CH-CH=CH-CH₃ | HO-CH₂-CH=CH-CH=CH-CH₃, Ac₂O |

TABLE 3

1,5-Enynes.

| Compound Identifier | Structure | Reactants |
|---|---|---|
| 3a | (NC)₂C(cyclohexenyl)CH₂C≡CH | (NC)₂C=cyclohexylidene, Br-CH₂-C≡CH |
| 3b | (MeO₂C)(NC)C(cyclohexenyl)CH₂C≡CH | (NC)(CO₂Me)C=cyclohexylidene, Br-CH₂-C≡CH |
| 3c | (NC)₂C(4-methylcyclohexenyl)CH₂C≡CH | (NC)₂C=(4-methylcyclohexylidene), Br-CH₂-C≡CH |
| 3d | (NC)₂C(4-CO₂Et-cyclohexenyl)CH₂C≡CH | (NC)₂C=(4-CO₂Et-cyclohexylidene), Br-CH₂-C≡CH |

TABLE 3-continued 1,5-Enynes.

| Compound Identifier | Structure | Reactants |
|---|---|---|
| 3e | (structure with bicyclic N-Boc alkene, malononitrile, and terminal alkyne) | (bicyclic N-Boc dicyanoalkene) and propargyl bromide |
| 3f | (structure with bicyclic alkene, malononitrile, and terminal alkyne) | (bicyclic dicyanoalkene) and propargyl bromide |
| 3g | (cyclohexene with CO₂Et, malononitrile, internal alkyne with OAc) | (cyclohexanone-derived dicyanoalkene with CO₂Et) and Br-CH₂-C≡C-CH₂-OAc |
| 3h | (bicyclic N-Boc alkene, malononitrile, internal methyl alkyne) | (bicyclic N-Boc dicyanoalkene) and 1-bromo-2-butyne |
| 3i | (bicyclic N-Boc alkene, malononitrile, phenyl alkyne) | (bicyclic N-Boc dicyanoalkene) and propargyl bromide with Ph |
| 3j | (bicyclic N-Boc alkene, malononitrile, alkyne-CH₂-OAc) | (bicyclic N-Boc dicyanoalkene) and Br-CH₂-C≡C-CH₂-OAc |

TABLE 3-continued 1,5-Enynes.

| Compound Identifier | Structure | Reactants |
|---|---|---|
| 3k | [structure: bicyclic alkene with C(CN)₂ group bearing CH₂-C≡C-CH₂-OAc] | [structure: bicyclic alkene with =C(CN)₂], Br-CH₂-C≡C-CH₂-OAc |
| 3l | [structure: cyclohexene with NHAc and C(CN)₂-CH₂-C≡CH substituent] | [structure: cyclohexane with NHAc and =C(CN)₂], Br-CH₂-C≡CH |
| 3m | [structure: dioxolane-spiro-cyclohexene with C(CN)₂-CH₂-C≡CH substituent] | [structure: dioxolane-spiro-cyclohexane with =C(CN)₂], Br-CH₂-C≡CH |

TABLE 4

Allenyne Precursor.

| Compound Identifier | Structure | Procedure* | Reactants |
|---|---|---|---|
| 5aa | [structure: cyclohexene bearing a CH(vinyl) with C(CN)₂-CH₂-C≡CH] | A | [structure: cyclohexene-C(CN)₂-CH₂-C≡CH] (3a), Br-CH₂-C≡CH (2a) |

TABLE 4-continued

Allenyne Precursor.

| Compound Identifier | Structure | Procedure* | Reactants |
|---|---|---|---|
| 5ab | 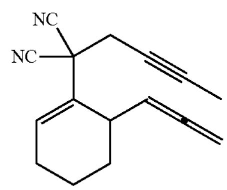 | A | (3a), (2b) |
| 5ac | 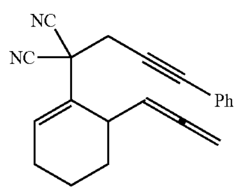 | A | (3a), (2c) |
| 5ad | 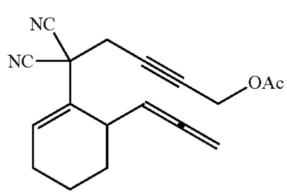 | A | (3a), (2d) |
| 5bd | 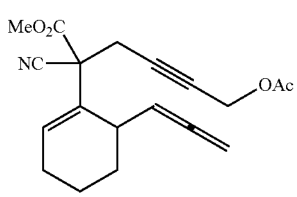 | A | (3b), (2d) |

TABLE 4-continued

Allenyne Precursor.

| Compound Identifier | Structure | Procedure* | Reactants |
|---|---|---|---|
| 5cd | 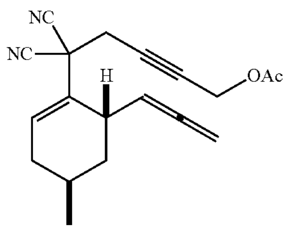 | A | (3c), (2d) Br-CH₂-C≡C-CH₂-OAc |
| 5dd | 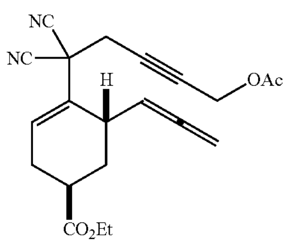 | A | (3d), (2d) Br-CH₂-C≡C-CH₂-OAc |
| 5de | 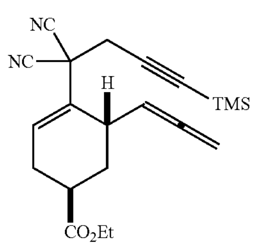 | A | (3d), (2e) Br-CH₂-C≡C-TMS |

TABLE 4-continued

Allenyne Precursor.

| Compound Identifier | Structure | Procedure* | Reactants |
|---|---|---|---|
| 5ed | [Structure with R = Boc] | A | (3e) [Structure, R = Boc], (2d) Br-CH₂-C≡C-CH₂-OAc |
| 5fd | [Structure] | A | (3f) [Structure], (2d) Br-CH₂-C≡C-CH₂-OAc |
| 5hd | [Structure with Me, R = Boc] | A | (3h) [Structure, R = Boc], (2d) Br-CH₂-C≡C-CH₂-OAc |
| 5id | [Structure with Ph, R = Boc] | A | (3i) [Structure with Ph, R = Boc], (2d) Br-CH₂-C≡C-CH₂-OAc |

TABLE 4-continued

Allenyne Precursor.

| Compound Identifier | Structure | Procedure* | Reactants |
|---|---|---|---|
| 5jd | (structure with R = Boc, OAc groups, NC, NC) | A | (3j) R = Boc; (2d) Br-CH₂-C≡C-CH₂-OAc |
| 5kd | (bicyclic structure with OAc, NC groups) | A | (3k); (2d) Br-CH₂-C≡C-CH₂-OAc |
| 7ad | (cyclohexane with NC, NC, OAc alkyne and allene) | B | (3a); (2d) Br-CH₂-C≡C-CH₂-OAc |

TABLE 4-continued

Allenyne Precursor.

| Compound Identifier | Structure | Procedure* | Reactants |
|---|---|---|---|
| 7dd | (structure with NC, NC, H, H, OAc, CO₂Et) 25% | B | (structure 3d with NC, NC, CO₂Et), (2d) Br—C≡C—OAc 55% 20% |
| 7ld | (structure with NC, NC, H, H, OAc, NHAc) | B | (structure 3l with NC, NC, NHAc), (2d) Br—C≡C—OAc |

TABLE 4-continued

Allenyne Precursor.

| Compound Identifier | Structure | Procedure* | Reactants |
|---|---|---|---|
| 7md | [structure with NC, NC, H, OAc, allene and dioxolane groups] | B | [structure (3m) with NC, NC, alkyne, dioxolane], [Br–CH₂–C≡C–CH₂–OAc (2d)] |

*Procedure A is carried out using the one-pot Cope/α-alkylation reaction using NaH in second step as described herein below; Procedure B is carried out using the one-pot Cope/alkylidene reduction/α-alkylation reaction using a Hantzsch ester in the first step and $K_2CO_3$ in the second step as described herein below.

TABLE 5

Allene/Tethered π Substrates.

| Compound Identifier | Structure | Reactants |
|---|---|---|
| 7a | [structure with NC, NC, Ph, vinyl, bicyclic N-Boc], R = Boc | [structure (3e) with NC, NC, alkyne, bicyclic N-Boc, R = Boc], [Br–CH₂–C≡C–Ph (2e)] |
| 7b | [structure with Ph, NC, CN, H, H, allene, bicyclic N-Boc], R = Boc | [structure (3e), R = Boc], [Br–CH₂–C≡C–Ph (2e)] |
| 7c | [structure with NC, CN, Ph, H, H, vinyl, bicyclic N-Boc], R = Boc | [structure (3e), R = Boc], [Br–CH₂–C≡C–Ph (2e)] |
| 7d | [structure with NC, NC, H, diene, vinyl, bicyclic N-Boc], R = Boc | [structure (3e), R = Boc], [AcO–CH₂–CH=CH–CH=CH–CH₃ (2f)] |

TABLE 5-continued

Allene/Tethered π Substrates.

| Compound Identifier | Structure | Reactants |
|---|---|---|
| 7e | [structure] | [structures] (3e), R = Boc; EtO2C-furan-CH2Cl |
| 7f | [structure] | [structures] (3e), R = Boc; EtO2C-furan-CH2Cl |

TABLE 6

Terpenoid Scaffolds.

| Compound Identifier | Structure | Reactants |
|---|---|---|
| 6aa | [structure] | [structure] (5aa) |
| 6cd | [structure] | [structure] (5cd) |
| 6dd | [structure] | [structure] (5dd) |
| 6de | [structure] | [structure] (5de) |
| 6ed | [structure] | [structure] (5ed), R = Boc |

TABLE 6-continued

Terpenoid Scaffolds.

| Compound Identifier | Structure | Reactants |
|---|---|---|
| 6hd | (5hd) R = Boc | R = Boc |
| 6jd | (5jd) R = Boc | R = Boc |
| 6kd | | (5aa) |
| 6md | | (7md) |

TABLE 7

Intramolecular Diels-Alder Furan Reaction Product.

| Compound Identifier | Structure | Reactants |
|---|---|---|
| 8 | Equivalent structures | (7e) |

TABLE 8

Functional Group Interconversion Reaction Products.

| Compound Identifier | Structure | Reactants |
|---|---|---|
| 9a | 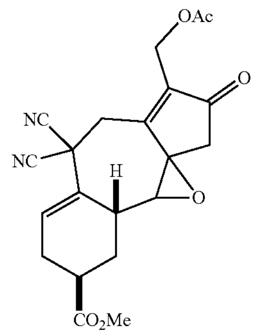 | reaction with 1.5 equivalents mCPBA, DCM (0.1M), 0° C. to room temperature. |
| 9b | 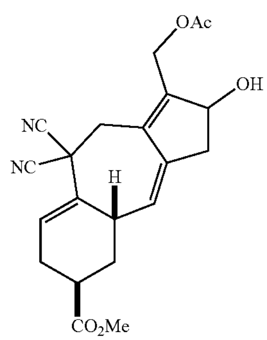 | reaction with 2 equivalents NaBH4, MeOH (0.5M), 0° C. |
| 9c | 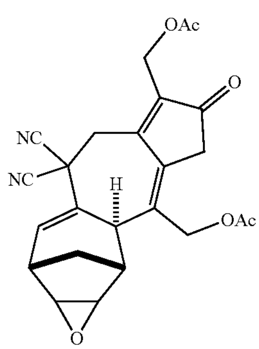 | (6kd) reaction with 1.5 equivalents of mCPBA, DCM (0.1M), 0° C. to room temperature. |

TABLE 8-continued

Functional Group Interconversion Reaction Products.

| Compound Identifier | Structure | Reactants |
|---|---|---|
| 9d | [structure] | [structure] (6kd) reaction with 3 equivalents of styrene, 3 mol % Grubbs II, 60° C. |

Figure 2:
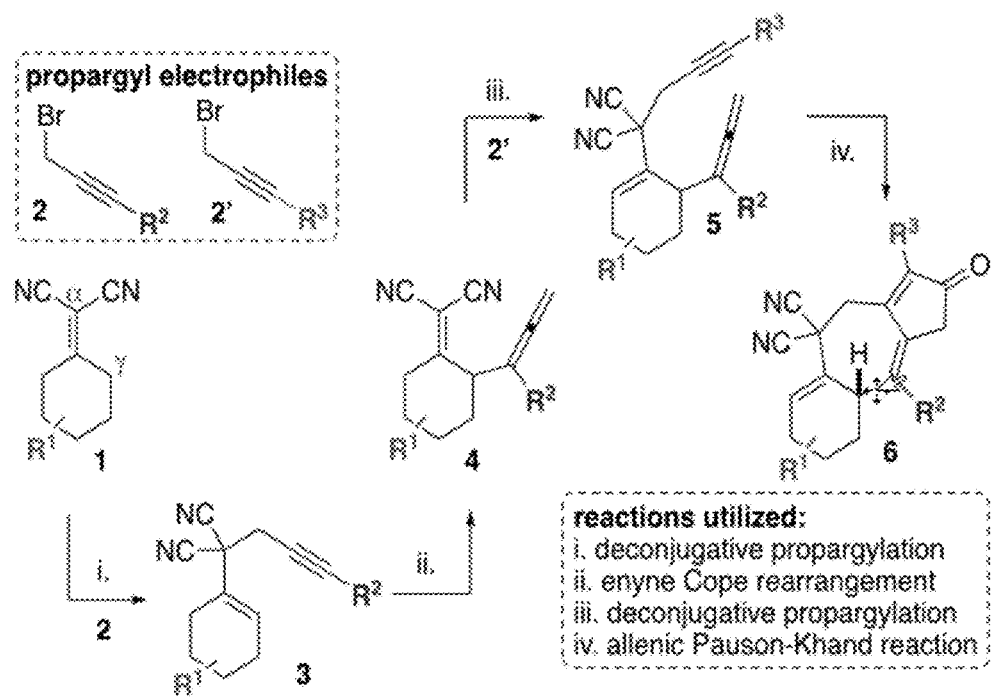
FIG. 2 shows a representative disclosed synthesis for the preparation of 6/7/5 tricycloalkane terpenoid cores or scaffolds.

In the discussion herein below, reference is made to different reaction schemes which are further detailed in the figures as follows: Scheme 1, see FIG. 2; Scheme 2, see FIGS. 3A-3B; Scheme 3, see FIGS. 4A-4C; Scheme 4, see FIGS. 5A-5C; Scheme 5, see FIGS. 6A-6B; Scheme 6, see FIGS. 7A-7B; and Scheme 7, see FIGS. 8A-8B.

Scheme 1. The strategy for assembling 6/7/5 scaffolds. Inspired by synthetically challenging 6/7/5 tricyclic terpenoid natural products (FIG. 1), which offer promising biological activities by way of unique functionalization and oxidation patterns (e.g., see Ref. 7), the disclosed methods were developed to provide novel approaches to tunably assemble terpenoid cores or scaffolds decorated with numerous functional groups (Scheme 1, FIG. 2): Deconjugative α-alkylation (e.g., see Ref. 8) of Knoevenagel adduct 1 with propargyl bromide 2 prepares the 1,5-enyne 3. Enyne [3,3] Cope rearrangement (e.g., see Ref. 9) results in γ-allenyl Knoevenagel adduct 4 and repeating the deconjugative α-propargylation step affords the 1,7-allenyne 5. Finally, allenic-Pauson-Khand reaction (e.g., see Refs. 6f, 6k, 10, 11) completes the 6/7/5 core structure with a variety of substitution, controlled by cholce of starting material ("R"-groups), and unique functional handles (e.g. gem-dinitrile, alkene, s-trans-diene, an enone) for diversification.

The disclosed synthetic methods have several notable features. First, they employs only abundant starting materials (ketones+malononitrile=Knoevenagel adducts; propargyl electrophiles). Second, the coupling reactions (deconjugative α-alkylation) are operationally simple due to the ease of Knoevenagel adduct anion generation (γ-C—H $pK_a$<10; e.g., see Ref. 12). The disclosed methods also provide approaches to a rare 1,5-enyne Cope rearrangement (e.g., see Ref. 9). Although the reaction has been described (three isolated examples, e.g., see Ref. 9) and computationally examined (e.g., see Ref. 13), it has had little to no application in synthesis. The disclosed methods also surprisingly improve the scope and understanding of the Cope rearrangement of 3,3-dicyano-1,5-enynes. The final feature of the disclosed methods is the use of the allenic-Pauson-Khand reaction (PKR). When preparing hydroazulenes by PKR, it is essential that the "alkene" coupling partner be an allene (e.g., see Refs. 6f, 6k, 10, 11).

Scheme 2. Scope of 1,7-allenyne synthesis. 1,5-enynes. 3a-3f bearing a terminal alkyne were prepared by reaction of Knoevenagel adducts and propargyl bromide in DMF with $K_2CO_3$ as a base. In general, 1,5-enyne syntheses are rapid and high yielding on both milligram and gram scales. Surprisingly, the reaction was successful, particularly in view of uncertainties regarding the 1,5-enyne [3,3] Cope rearrangement due to the minimal prior precedent (e.g., see Ref. 9). The disclosed methods surprisingly provide a means to this reaction, e.g., the reaction went forward at 150° C. in toluene in screw-cap pressure flasks (Scheme 2, FIGS. 3A-3B). It was determined that it was typically most practical to not isolate the γ-allenyl Knoevenagel adducts 4. Rather, following [3,3] rearrangement, the solvent was "swapped" (toluene for THF) and the allene was directly treated with NaH and a second equivalent of a 1° propargyl bromide derivative to yield the 1,7-allenynes 5 in good yield over the telescoped procedure (20-56% yield of 1,7-allenynes). Reported in Scheme 2 are two-step yields, averaging 45%-75% yield per step, where inexpensive and abundant starting materials are converted into synthetically useful 1,7-allenyes. Notably, the procedure is scalable and reproducible; the reaction sequence was examined on the 300 mg-2 gram scale with little change in efficiency.

Through the sequence, cyclohexenyl substitution is controlled by choice of cycloalkanone starting material. For example, substrates 3c and 3d, prepared from 4-substituted cyclohexanone, were found to yield the allenynes 5cd and 5dd. Furthermore, the Cope rearrangement was diastereoselective (>20:1 dr) in these cases. Alkyne substitution is varied by choice of propargyl bromide starting material. For example, 1,7-allenynes were prepared bearing a phenylacetylene moiety (5ac), a propargyl acetate (5ad), and a TMS-alkyne (5de). Finally, bicyclic 1,7-allenynes 5ed and 5fd were prepared from tropinone (3e) and the (4+3) adduct (3f) of cyclopentadiene and trichloroacetone.

Scheme 3. 1,5-enynes that do not (A) and do (B) undergo [3.3] rearrangement. 1,5-enynes that do not (FIG. 4A) and do (FIG. 4) undergo [3,3] rearrangement. The [3,3] Cope rearrangement of 1,5-enynes 3g-3k bearing an internal alkyne (Scheme 3) was examined. Initial studies revealed a method limitation: cyclohexenyl substrates such as 3g degraded under thermal conditions. Specifically, conversion was only observed at a higher temperature (200° C.) compared to the results in Scheme 2 (150° C.), but no desired product could be isolated. Interestingly, the bridged bicyclic substrates 3h-3k underwent an efficient Cope rearrangement and the desired allenynes could be isolated in good yields over the telescoped sequence.

Allenes are generally useful for intramolecular cycloisomerization (e.g., see Ref. 15). As such, other functionalized electrophiles were examined in order to prepare diverse allene/tethered-π substrates (Scheme 4). Enyne Cope rearrangement/allylation with cinnamyl bromide resulted in separable products 7a and 7b in 60% and 23% yields, respectively. Enyne Cope rearrangement/Pd-catalyzed allylation with cinnamyl acetate intriguingly resulted in diastereo-, γ-, and branch-selective allylation in good yield (product 7c). At this point, we do not understand why this combination of substrates and catalyst gives this result, although it is interesting and potentially useful for making complex polycyclic small molecules. It should also be noted that 7a can convert to 7c by thermal [3,3] rearrangement (e.g., see Ref. 16). Considering these results, it was surprising to find that enyne Cope rearrangement/Pd-catalyzed allylation with sorbyl acetate results exclusively in linear-selective deconjugative α-allylation. Reaction of furan-containing alkyl chloride was also examined. The enyne-Cope rearrangement/alkylation resulted in a separable mixture of deconjugative α-alkylation product 7e and γ-alkylated product 7f.

Scheme 4. Other allene/tethered π-systems prepared. Using the allenic-Pauson-Khand reaction (e.g., see Refs. 6f, 6k, 10, 11), the 1,7-allenynes were converted into their respective 6/7/5 tricycloalkane cores without incident by the standard literature protocol developed and applied by Brummond and others (Scheme 5; e.g., see Refs. 6f, 6k, 10, 11). The cores are highly complex and diverse, considering the sequence is four steps from abundant starting materials.

Scheme 5. Synthesis of 6/7/5 tricycloalkane terpenoid scaffolds. Allenyne precursor compounds prepared by the methods discussed herein were converted in a single step reaction to 6/7/5 tricycloalkane terpenoid scaffolds with a variety of substitution, controlled by choice of starting material (choice of substituent groups in the various reactants in the generalized reaction scheme), and unique functional handles (e.g. gem-dinitrile, alkene, s-trans-diene, an enone) for diversification.

Figure 7A:
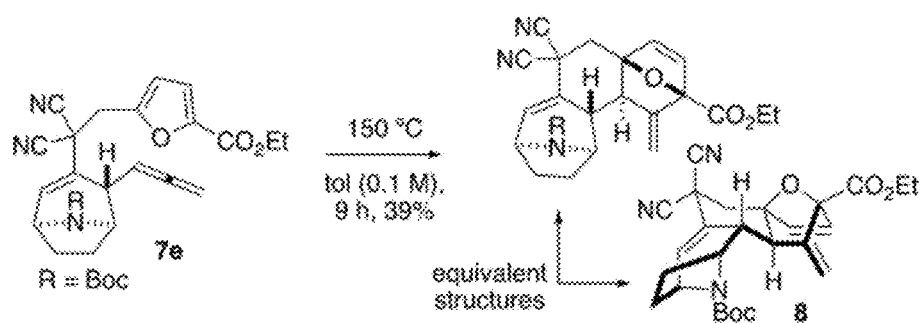
FIGS. 7A-7B show representative disclosed syntheses for the preparation of representative disclosed compounds.
Figure 7B:
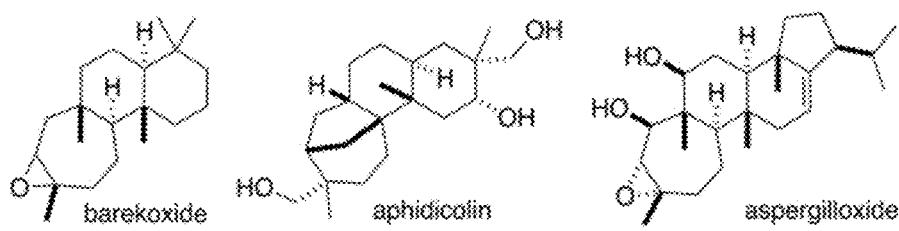
Figure 8A:
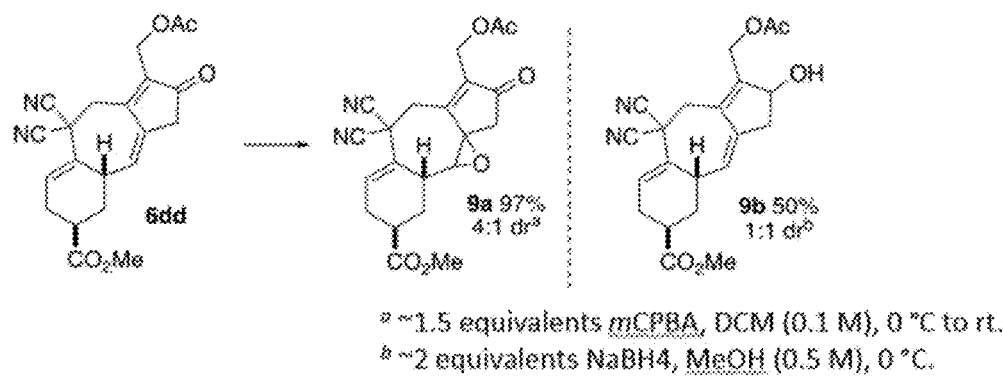
FIGS. 8A-8B show representative disclosed syntheses for the representative disclosed functional group interconversion reactions.
Figure 8B:
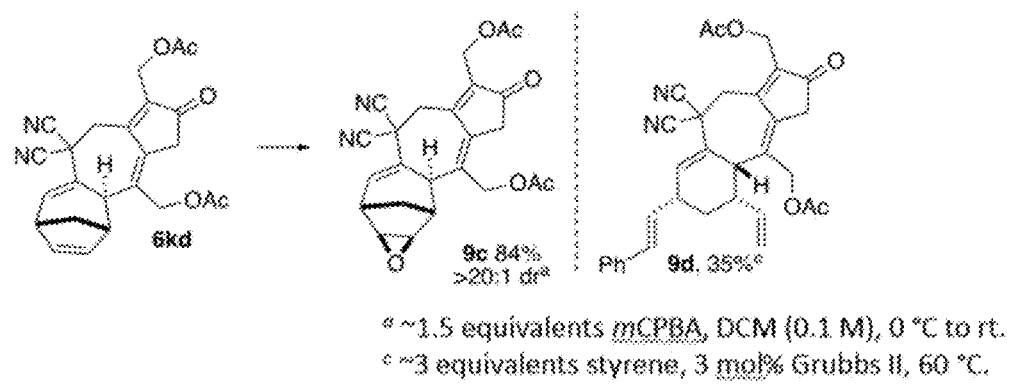

Scheme 6. An intramolecular Diels-Alder furan reaction. The reaction of furan-containing allene 7e with regard to intramolecular Diels-Alder furan (IMDAF) reactivity (Scheme 6; see FIG. 7A; e.g., see Ref. 17). It was surprising to find that thermal conditions could convert 7e to the functionally dense polycycloalkane 8 in 39% yield. 8 contains a 6/6/7 tricycloalkane framework, two-heteroatomic bridges, and numerous other functional groups and was prepared in four steps from inexpensive commercial materials. Notably, there are terpenoid natural products that bear a related 6/6/7 tricycloalkane tricycloalkane ring system (FIG. 7B; and e.g., see Ref. 18).

Scheme 7. Functional group interconversion reactions. The most reactive olefin toward epoxidation was the γ,δ-olefin on the conjugated dienone for substrate 6dd. For the more strained scaffold 6kd, the bicyclo[3.2.1]octene was most reactive yielding 9c. Also, the ketone could be reduced using NaBH₄ to prepare 9b. Finally, ring-opening/cross metathesis could be performed on the bicyclo[3.2.1]octene core yielding 9d.

In conclusion, the disclosed methods provide a new route to 6/7/5 tricycloalkane frameworks. The sequence hinged on the development of poorly understood 3,3-dicyano-1,5-enyne Cope rearrangement. The disclosed methods provide novel conditions for these reaction and take this reaction into novel chemical space well beyond the current limitations for this transformation. The disclosed methods provide novel methods for the synthesis of diverse linear 6/7/5 tricycloalkanes, as well as a highly complex 6/6/7 tricycloalkane, all in four steps from cycloalkanone, malononitrile, and two different alkyl electrophiles (propargyl-, allyl- and furan-containing electrophiles).

2. General Experimental

All commercial materials were used without further purification. $^1$H NMR and $^{13}$C NMR spectra were recorded in CDCl$_3$ (with CHCl$_3$ residual peak as an internal standard), DMSO-d6 (with DMSO-d5 residual peak as an internal standard), or toluene-d$_8$ (with toluene-d$_7$ residual peak as an internal standard) using a 500 MHz or 600 MHz spectrometer (see: (a) Gottlieb, H. E., et al. *J. Org. Chem.* 1997, 62, 7512; and (b) Fulmer, G. R., et al. *Organometallics* 2010, 29, 2176. Variable temperature NMR (80° C.) was used to record all samples run in DMSO-d$_6$ or toluene-d$_8$. All $^{13}$C NMR spectra were recorded with complete proton decoupling. HRMS data were recorded on Agilent Time of Flight 6200 spectrometer. Reaction progress was monitored by thin-layer chromatography (TLC) and visualized by UV light, phosphomolybdic acid stain, and KMnO$_4$ stain. Commercially available anhydrous DMF stored over molecular sieves was used for α-alkylation of Knoevenagel adducts and commercially available anhydrous methanol was used for NaBH$_4$ reduction. All other reactions (with the exception of Knoevenagel condensation reactions) were carried out using anhydrous solvents obtained dried by passing through activated alumina columns. Bicyclo[3.2.1]oct-6-en-3-one was prepared according to a previously published procedure (see Rudroff, F., et al. *Tetrahedron* 2016, 72(46), 7212).

3. General Procedure for Knoevenagel Condensation

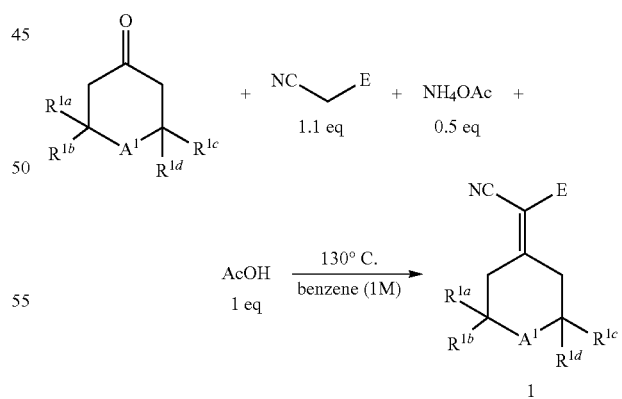

The ketone, malonate derivative (1.1 equivalents), ammonium acetate (0.5 equivalents), and acetic acid (1 equivalent) were dissolved in benzene (1.0 M with respect to the ketone) and refluxed at 130° C. using a Dean-Stark apparatus. When the ketone was fully consumed (monitored by TLC, 4-16 hrs.), the reaction mixture was cooled to room temperature and solvent was evaporated. The crude product was then filtered through a silica plug and then concentrated under vacuum. The pure products were isolated via column chromatography (hexane-ethyl acetate) unless otherwise noted. Using the foregoing method, compounds 1a-1f and 1l-1m were prepared, and are described in further detail herein below.

a. 2-CYCLOHEXYLIDENEMALONONITRILE (1A).

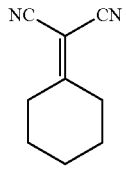

The compound was isolated as a colorless Oil, 95% yield, 7.07 g; and purified using 10% EtOAc in hexane; $R_f$=0.3 (10% EtOAc in hex). Analytical data were consistent with that in the reference (Longstreet, A. R., et al., *Org. Lett.* 2013, 15 (20), 5298).

b. METHYL 2-CYANO-2-CYCLOHEXYLIDENEACETATE (1B).

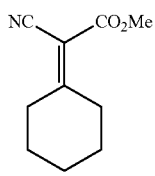

The compound was isolated as a light yellow oil, 43% yield, 3.88 g; and purified using gradient: 5%-15% EtOAc in hexane. $^1$H NMR (500 MHz, CDCl$_3$) δ 3.73 (s, 3H), 2.94-2.86 (t, J=6.1 Hz, 2H), 2.58 (t, J=6.4 Hz, 2H), 1.77-1.54 (m, 6H). $^{13}$C NMR (125 MHz, CDCl$_3$) δ 180.4, 162.2, 115.4, 101.4, 52.3, 36.7, 31.4, 28.5, 28.1, 25.4. HRMS (ESI-TOF) m/z: [M+H]$^+$ Calcd for C$_{10}$H$_{14}$NO$_2$ 180.1019; Found 180.1016. $R_f$=0.56 (20% EtOAc in hexane).

c. 2-(4-METHYLCYCLOHEXYLIDENE)MALONONITRILE (1C).

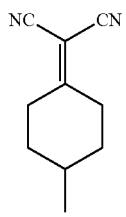

The compound was isolated as an orange oil, 100% conversion, used crude in next step, $^1$H NMR (300 MHz, CDCl$_3$) δ 3.08-2.94 (m, 2H), 2.44-2.27 (m, 2H), 2.08-1.96 (m, 2H), 1.75 (dddp, J=13.9, 10.3, 6.7, 3.3 Hz, 1H), 1.32- 1.16 (m, 2H), 0.98 (d, J=6.6 Hz, 3H). $^{13}$C NMR (125 MHz, CDCl$_3$) δ 184.9, 111.8, 82.8, 35.7, 34.2, 31.4, 20.9. HRMS (ESI-TOF) m/z: [M−H]$^−$ Calcd for C$_{10}$H$_{11}$N$_2$ 159.0928; Found 159.0926. $R_f$=0.30 (10% EtOAc in hexane).

d. ethyl 4-(DICYANOMETHYLENE)CYCLOHEXANE-1-CARBOXYLATE (1D).

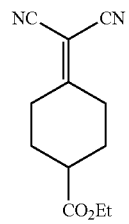

100% conversion, used crude in next step. $^1$H NMR (500 MHz, CDCl$_3$) δ 4.17 (q, J=7.1 Hz, 2H), 2.95 (dt, J=14.8, 5.1 Hz, 2H), 2.68 (tt, J=8.9, 4.1 Hz, 1H), 2.55 (ddd, J=14.8, 10.1, 4.9 Hz, 2H), 2.15 (dq, J=15.1, 5.4, 5.0 Hz, 2H), 1.93 (dtd, J=14.0, 9.7, 4.5 Hz, 2H), 1.27 (t, J=7.2 Hz, 3H). $^{13}$C NMR (125 MHz, CDCl$_3$) δ 182.5, 173.3, 111.5, 83.6, 61.0, 40.5, 32.6, 29.1, 14.2. HRMS (ESI-TOF) m/z: [M−NH$_4$]$^+$ Calcd for C$_{12}$H$_{18}$N$_3$O$_2$ 236.1394; Found 236.1405. $R_f$=0.23 (20% EtOAc in hexane)

e. TERT-BUTYL 3-(DICYANOMETHYLENE)-8-AZABICYCLO[3.2.1]OCTANE-8-CARBOXYLATE (1E).

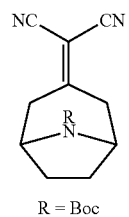

R = Boc

Tan solid, 100% conversion, used crude in next step. $^1$H NMR (500 MHz, CDCl$_3$) δ 4.45 (bs, 2H), 2.92 (d, J=15.6 Hz, 2H), 2.72 (d, J=49.6 Hz, 2H), 2.05 (bs, 2H), 1.55 (d, J=8.3 Hz, 2H), 1.48 (s, 9H). $^{13}$C NMR (125 MHz, CDCl$_3$) δ 179.0, 153.1, 111.3, 87.9, 81.0, 77.4, 77.2, 76.9, 54.0, 40.6, 40.0, 28.5. HRMS (ESI-TOF) m/z: [M+Na]$^+$ Calcd for C$_{15}$H$_{19}$N$_3$O$_2$Na 296.1369; Found 296.1365. $R_f$=0.28 (20% EtOAc in hexane)

f. 2-(BICYCLO[3.2.1]OCT-6-EN-3-YLIDENE)MALONONITRILE (1F).

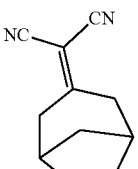

White solid, 57% yield, 1.4 g. Purified using 10% EtOAc in hexane. ¹H NMR (500 MHz, Chloroform-d) δ 5.97 (s, 2H), 2.97 (dd, J=15.4, 2.4 Hz, 2H), 2.91 (d, J=2.6 Hz, 2H), 2.57 (dd, J=18.4, 2.9 Hz, 2H), 2.08 (dtt, J=10.5, 5.2, 2.5 Hz, 1H), 1.68 (d, J=11.0 Hz, 1H). ¹³C NMR (125 MHz, cdcl₃) δ 67 183.4, 135.0, 111.6, 88.2, 42.5, 38.9, 37.2. HRMS (ESI-TOF) m/z: [M+Na]⁺ Calcd for $C_{11}H_{10}N_2Na$ 193.0736; Found 193.0734. $R_f$=0.4 (20% EtOAc in hexane).

g.
N-(4-(DICYANOMETHYLENE)CYCLOHEXYL)
ACETAMIDE (1L).

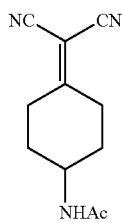

Orange solid, 97% yield, 6.3 g. Used without further purification. ¹H NMR (500 MHz, CD₃OD) δ 3.99 (tt, J=10.2, 4.1 Hz, 1H), 2.95 (dtd, J=14.7, 4.8, 1.6 Hz, 2H), 2.68-2.51 (m, 2H), 2.20-2.07 (m, 2H), 1.94 (m, 4H), 1.65-1.44 (m, 2H). ¹³C NMR (125 MHz, CD₃OD) δ 182.8, 171.3, 111.3, 82.5, 46.0, 31.6, 31.5, 21.2. HRMS (ESI-TOF) m/z: [M–Na]⁺ Calcd for $C_{11}H_{13}N_3ONa$ 226.0951; Found 226.0961.

h. 2-(1,4-DIOXASPIRO[4.5]DECAN-8-YLIDENE)
MALONONITRILE (1M).

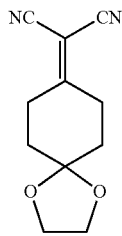 [SMILES: N#CC(C#N)=C1CCC2(CC1)OCCO2]

White solid, 80% yield, 5.2 g. Recrystallized in ethanol. $R_f$=0.42 (30% EtOAc in hex). Analytical data is consistent with that previously reported (Lahtigui, O., et al., *Angew. Chemie. Int*. Ed. 2016, 55 (51), 15792.).

4. Preparation of Propargyl Electrophiles
(Compounds 2, 2C, 2D, and 2F)

a. 4-HYDROXYBUT-2-YN-1-YL ACETATE (2).

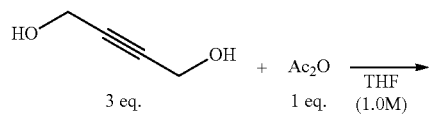

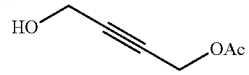

The diol (3 equivalents, 25.3 g, 293.86 mmol) and acetic anhydride (1 equivalent, 10 g, 97.95 mmol, 9.26 mL) were dissolved in THF (1.0 M with respect to the limiting reagent) and the solution was stirred at 40° C. for 18 hours. The solvent was then removed under reduced pressure and the crude product was filtered over a silica plug using 1:1 EtOAc-hexane to remove most of the excess diol. The product was purified using column chromatography (gradient: 20%→40% EtOAc in hexane). Pale yellow oil, 68% yield, 8.51 g. Analytical data is consistent with that previously reported (Pacheco, M. C.; Gouvemeur, V. *Org. Lett*. 2005, 7(7), 1267).

b. (3-BROMOPROP-1-YN-1-YL)BENZENE (2C).

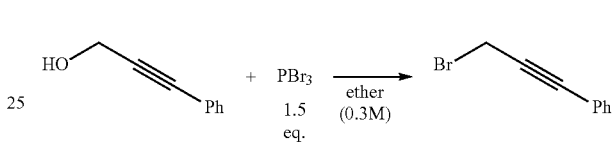

The propargyl alcohol (1.0 g, 7.57 mmol, 0.94 mL) was dissolved in 30 mL anhydrous ether and the solution was cooled to 0° C. PBr₃ (1.5 equivalents, 3.07 g, 11.35 mmol, 1.07 mL) was then added dropwise, and the solution was allowed to warm to room temperature. Upon completion of the reaction (monitored by TLC) the reaction mixture was added to ice and extracted with EtOAc. The organic layer was then washed with a saturated solution of NaHCO₃ and brine and dried over Na₂SO₄. The crude product was concentrated under reduced pressure and purified via column chromatography (15% EtOAc in hexane). Yellow oil, 61% yield, 900 mg. Analytical data is consistent with that previously reported (Vyas, D.; Hazra, C.; Oestreich, M. *Org. Lett*. 2011, 13 (16), 4462).

c. 4-BROMOBUT-2-YN-1-YL ACETATE (2D)

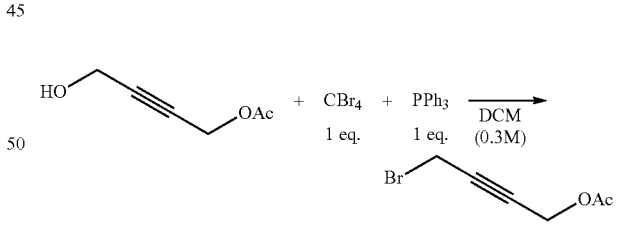

The propargyl alcohol (5 g, 39.02 mmol) was dissolved in 120 mL anhydrous DCM and CBr₄ (12.94 g, 39.02 mmol) was added to the solution. The reaction was then cooled to 0° C. and PPh₃ (10.24 g, 39.02 mmol) was added in small portions. After warming to room temperature, the reaction was stirred for 4 hours before quenching with 25 mL MeOH. The solvents were evaporated and the crude product was filtered through a silica plug (1:1 hexane-ethyl acetate). The product was then concentrated under reduced pressure and purified via column chromatography (10% ethyl acetate in hexane). Colorless oil, 73% yield, 5.46 g. Analytical data is consistent with that in the reference (Fischer, M., et al., *Eur. J. Org. Chem*. 2011, 2011 (9), 1645).

d. (2E,4E)-HEXA-2,4-DIEN-1-YL ACETATE (2F).

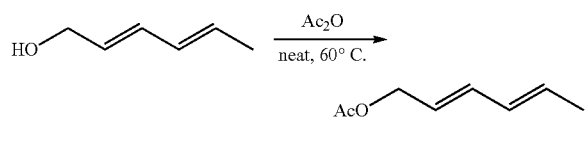

Sorbyl alcohol (1 g, 10.19 mmol, 1.12 mL) and acetic anhydride (3.12 g, 30.57 mmol, 2.89 mL) were heated to 60° C. neat for 5 hours. Upon completion of the reaction (monitored by TLC), the solution was taken up in ethyl acetate and washed with a saturated solution of NaHCO$_3$, then brine. The organic layer was dried over Na$_2$SO$_4$ and the solvent was removed under reduced pressure. Colorless oil, 99% yield, 1.42 g.

5. General Procedure for Decojugative α-Alkylation.

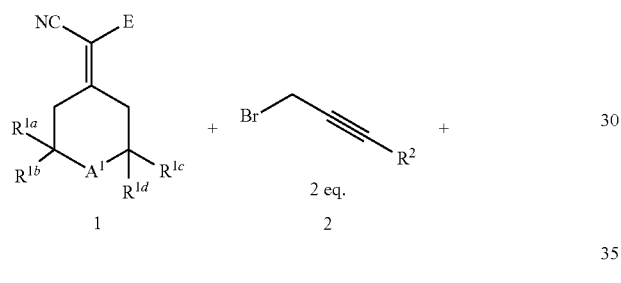

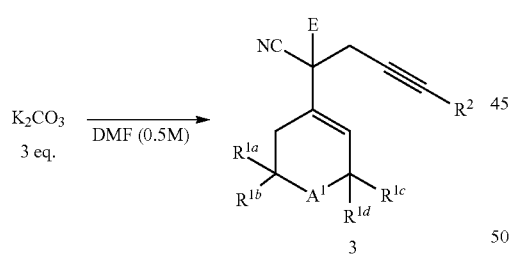

Knoevenagel adduct 1 and 2 equivalents of a propargyl bromide derivative 2 were dissolved in anhydrous DMF (0.5 M with respect to the limiting reagent). Finely ground K$_2$CO$_3$ (3 equivalents) was then added to the solution and stirred at room temperature until the limiting reagent was consumed (monitored by TLC; 30 min-2 hrs.). The solution was then diluted with EtOAc and washed with H$_2$O five times. The organic layer was then washed with brine and dried with Na$_2$SO$_4$. The solvent was removed under reduced pressure and the crude material purified via column chromatography (hexane-ethyl acetate) unless otherwise noted. Using the foregoing method, compounds 3a-3f and 3h-3m were prepared, and are described in further detail herein below.

a. 2-(CYCLOHEX-1-EN-1-YL)-2-(PROP-2-YN-1-YL)MALONONITRILE (3A).

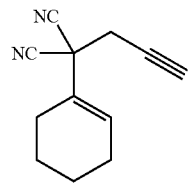

Pale yellow oil, 93% yield, 2.34 g. Purified using 10% EtOAc in hexane. $^1$H NMR (500 MHz, CDCl$_3$) δ 6.30 (dq, J=3.8, 2.0 Hz, 1H), 2.97 (d, J=2.6 Hz, 2H), 2.35 (t, J=2.5 Hz, 1H), 2.23-2.11 (m, 5H), 1.79-1.72 (m, 2H), 1.63 (pd, J=6.9, 6.2, 4.1 Hz, 2H). $^{13}$C NMR (125 MHz, CDCl$_3$) δ 131.0, 127.0, 113.9, 75.2, 74.9, 43.4, 28.8, 25.4, 24.5, 22.3, 21.3. HRMS (ESI-TOF) m/z: [M+H]$^+$ Calcd for C$_{12}$H$_{13}$N$_2$ 185.1073; Found 185.1080. [M+Na]$^+$ Calcd for C$_{12}$H$_{12}$N$_2$Na 207.0893; Found 207.0883. R$_f$=0.51 (20% EtOAc in hexane)

b. METHYL 2-CYANO-2-(CYCLOHEX-1-EN-1-YL)PENT-4-YNOATE (3B)

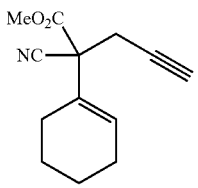

Pale yellow oil, 73% yield, 900 mg. Purified using 10% EtOAc in hexane. $^1$H NMR (500 MHz, CDCl$_3$) δ 6.11 (tt, J=3.9, 1.5 Hz, 1H), 3.84 (s, 3H), 2.98 (dd, J=16.7, 2.6 Hz, 1H), 2.83 (dd, J=16.8, 2.7 Hz, 1H), 2.21-2.07 (m, 3H), 2.08-1.94 (m, 2H), 1.74-1.50 (m, 4H). $^{13}$C NMR (125 MHz, CDCl$_3$) δ 167.1, 129.8, 128.8, 117.6, 77.6, 72.8, 54.8, 54.1, 25.7, 25.5, 24.8, 22.6, 21.5. HRMS: (ESI-TOF) m/z: [M+H]$^+$ Calcd for C$_{13}$H$_{16}$NO$_2$ 218.1176; Found 218.1184; [M+NH$_4$]$^+$ Calcd for C$_{13}$H$_{19}$N$_2$O$_2$ 235.1441; Found 235.1451; [M+Na]$^+$ Calcd for C$_{13}$H$_{15}$NO$_2$Na 240.0995; Found 240.1006. R$_f$=0.4 (20% EtOAc in hexane)

c. 2-(4-METHYLCYCLOHEX-1-EN-1-YL)-2-(PROP-2-YN-1-YL)MALONONITRILE (3C).

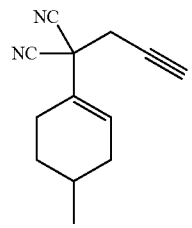

White solid, 90% yield, 1.12 g. Purified using 10% EtOAc in hexane. $^1$H NMR (500 MHz, CDCl$_3$) δ 6.27 (dq, J=4.4, 2.1 Hz, 1H), 3.02-2.92 (m, 2H), 2.36-2.33 (m, 1H), 2.29

(dtd, J=18.0, 4.9, 2.2 Hz, 1H), 2.18 (dh, J=8.7, 3.1, 2.5 Hz, 2H), 1.89-1.74 (m, 2H), 1.74-1.64 (m, 1H), 1.33 (dddd, J=13.1, 10.7, 8.8, 6.7 Hz, 1H), 0.99 (d, J=6.5 Hz, 3H). $^{13}$C NMR (125 MHz, CDCl$_3$) δ 130.55, 126.57, 113.83, 113.64, 75.05, 74.74, 43.00, 33.57, 30.20, 28.75, 27.37, 24.26, 21.05. HRMS: (ESI-TOF) m/z: [M+Na]$^+$ Calcd for C$_{13}$H$_{14}$N$_2$Na 221.1049; Found 221.1052. R$_f$=0.4 (15% EtOAc in hexane)

d. ETHYL 4-(1,1-DICYANOBUT-3-YN-1-YL)CYCLOHEX-3-ENE-1-CARBOXYLATE (3D).

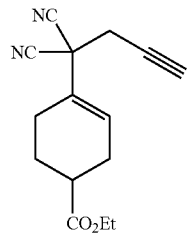

Pale yellow crystals, 84% yield, 12.61 g. Recrystalized in EtOH. $^1$H NMR (500 MHz, CDCl$_3$) δ 6.31 (dt, J=4.2, 2.1 Hz, 1H), 4.16 (q, J=7.1 Hz, 2H), 2.98 (d, J=2.6 Hz, 2H), 2.58 (dddd, J=11.1, 9.0, 5.9, 3.1 Hz, 1H), 2.45 (dt, J=8.6, 3.0 Hz, 2H), 2.35 (t, J=2.5 Hz, 1H), 2.32-2.19 (m, 2H), 2.15 (dq, J=13.0, 4.3 Hz, 1H), 1.83 (dddd, J=13.1, 10.6, 9.0, 5.9 Hz, 1H), 1.26 (t, J=7.1 Hz, 3H). $^{13}$C NMR (125 MHz, CDCl$_3$) δ 174.4, 129.3, 126.9, 113.6, 113.5, 75.4, 74.6, 60.9, 42.9, 38.1, 28.9, 27.6, 24.8, 23.7, 14.3. HRMS: (ESI-TOF) m/z: [M+Na]$^+$ Calcd for C$_{15}$H$_{16}$N$_2$O$_2$Na 279.1104; Found 279.1101. R$_f$=0.54 (30% EtOAc in hexane)

e. TERT-BUTYL 3-(1,1-DICYANOBUT-3-YN-1-YL)-8-AZABICYCLO[3.2.1]OCT-2-ENE-8-CARBOXYLATE (3E).

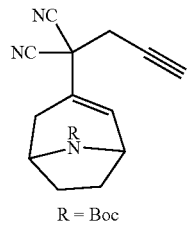

R = Boc

White solid, 95% yield, 2.16 g. Purified using 10% EtOAc in hexane. $^1$H NMR (500 MHz, DMSO-d$_6$) δ 6.56 (d, J=5.3 Hz, 1H), 4.42 (s, 1H), 4.33 (dd, J=7.8, 4.6 Hz, 1H), 3.31 (d, J=2.5 Hz, 2H), 3.25 (t, J=2.5 Hz, 1H), 2.81-2.73 (m, 1H), 2.14 (dq, J=13.9, 7.2 Hz, 1H), 2.02 (d, J=17.2 Hz, 1H), 1.90 (td, J=7.7, 3.8 Hz, 2H), 1.61 (dt, J=12.2, 7.7 Hz, 1H), 1.44 (d, J=7.6 Hz, 1H), 1.41 (s, 9H). $^{13}$C NMR (125 MHz, DMSO-d$_6$) δ 152.8, 134.5, 125.1, 113.4, 113.2, 78.7, 76.4, 75.6, 52.5, 51.0, 41.3, 33.1, 32.2, 28.5, 27.6, 26.8. HRMS (ESI-TOF) m/z: [M+H]$^+$ Calcd for C$_{18}$H$_{22}$N$_3$O$_2$ 334.1526; Found 334.1542. R$_f$=0.3 (20% EtOAc in hexane).

f. 2-(BICYCLO[3.2.1]OCTA-2,6-DIEN-3-YL)-2-(PROP-2-YN-1-YL)MALONONITRILE (3F).

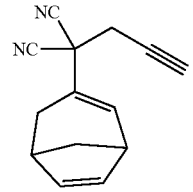 [SMILES: C#CCC(C#N)(C#N)C1=CC2C=CC(C1)C2]

White solid, 73% yield, 266 mg. Purified using 10% EtOAc in hexane. $^1$H NMR (500 MHz, CDCl$_3$) δ 6.69 (d, J=6.8 Hz, 1H), 6.22 (dd, J=5.6, 2.8 Hz, 1H), 5.81 (dd, J=5.6, 2.8 Hz, 1H), 2.98-2.89 (m, 4H), 2.43 (ddd, J=17.7, 5.3, 1.9 Hz, 1H), 2.34 (t, J=2.6 Hz, 1H), 1.99 (dt, J=9.6, 4.6 Hz, 1H), 1.92 (d, J=17.6 Hz, 1H), 1.66 (d, J=9.9 Hz, 1H). $^{13}$C NMR (125 MHz, CDCl$_3$) δ 139.0, 137.1, 131.2, 123.9, 113.6, 113.5, 75.3, 74.7, 42.8, 40.2, 38.6, 37.6, 28.9, 27.4. HRMS: (ESI-TOF) m/z: [M+Na]$^+$ Calcd for C$_{14}$H$_{12}$N$_2$Na 231.0893; Found 231.0884. R$_f$=0.43 (20% EtOAc in hexane)

g. TERT-BUTYL 3-(1,1-DICYANOPENT-3-YN-1-YL)-8-AZABICYCLO[3.2.1]OCT-2-ENE-8-CARBOXYLATE (3H).

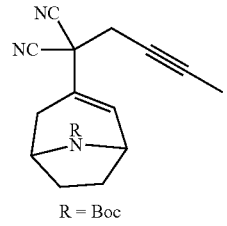

R = Boc

Yellow oil, 85% yield, 303 mg. Purified using 10% EtOAc in hexane. Note: isolated as a 6:1 mixture with unidentified byproduct. $^1$H NMR (500 MHz, DMSO-d$_6$) δ 6.54 (d, J=5.4 Hz, 1H), 4.43 (t, J=5.5 Hz, 1H), 4.34 (dd, J=7.6, 4.6 Hz, 1H), 3.21 (q, J=2.4 Hz, 2H), 2.76 (dd, J=17.6, 4.3 Hz, 1H), 2.15 (ddd, J=16.8, 9.7, 4.1 Hz, 1H), 2.01 (d, J=17.5 Hz, 1H), 1.89 (dd, J=6.1, 3.1 Hz, 1H), 1.84 (q, J=2.8 Hz, 3H), 1.79 (q, J=2.4 Hz, 1H), 1.61 (dt, J=12.9, 8.0 Hz, 1H), 1.42 (s, 9H). $^{13}$C NMR (125 MHz, DMSO-d$_6$) δ 152.9, 134.4, 125.3, 113.7, 113.5, 82.1, 78.7, 70.7, 52.5, 51.1, 41.7, 33.1, 32.3, 28.6, 27.6, 27.6, 27.4, 2.5. HRMS (ESI-TOF) m/z: [M+Na]$^+$ Calcd for C$_{19}$H$_{23}$N$_3$O$_2$Na 348.1682; Found 348.1694. R$_f$=0.31 (20% EtOAc in hexane)

h. TERT-BUTYL 3-(1,1-DICYANO-4-PHENYL-BUT-3-YN-1-YL)-8-AZABICYCLO[3.2.1]OCT-2-ENE-8-CARBOXYLATE (3I).

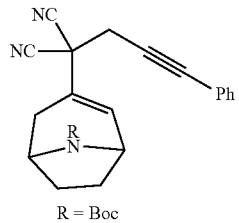

R = Boc

Yellow solid, 85% yield, 243 mg. Purified using 10% EtOAc in hexane. $^1$H NMR (500 MHz, DMSO-$d_6$) δ 7.52-7.34 (m, 5H), 6.63 (ddd, J=5.6, 2.0, 1.1 Hz, 1H), 4.46 (t, J=5.4 Hz, 1H), 4.35 (dd, J=7.0, 5.0 Hz, 2H), 3.59 (d, J=1.8 Hz, 2H), 2.87-2.78 (m, 1H), 2.20-2.05 (m, 2H), 1.94-1.78 (m, 2H), 1.68-1.60 (m, 1H), 1.40 (s, 9H). $^{13}$C NMR (125 MHz, DMSO-$d_6$) δ 152.8, 134.6, 131.0, 128.6, 128.2, 121.2, 113.5, 113.3, 85.4, 81.4, 78.7, 52.5, 51.0, 41.5, 33.1, 32.3, 28.6, 27.7, 27.6. HRMS (ESI-TOF) m/z: [M+Na]$^+$ Calcd for $C_{24}H_{25}N_3O_2Na$ 410.1839; Found 410.1840. *Note: sample was dissolved in MeOH. $R_f$=0.25 (20% EtOAc in hexane)

i. TERT-BUTYL 3-(5-ACETOXY-1,1-DICYANO-PENT-3-YN-1-YL)-8-AZABICYCLO[3.2.1]OCT-2-ENE-8-CARBOXYLATE (3J).

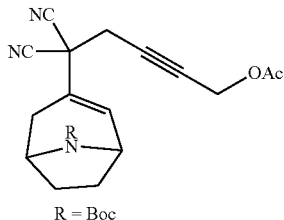

R = Boc

Pale yellow oil, 79% yield, 221 mg. Purified using gradient 10%→20% EtOAc in hexane. $^1$H NMR (500 MHz, DMSO-$d_6$) δ 6.55 (d, J=5.3 Hz, 1H), 4.72 (t, J=2.1 Hz, 2H), 4.43 (t, J=4.3 Hz, 1H), 4.34 (dt, J=7.9, 2.8 Hz, 1H), 3.39 (q, J=2.3 Hz, 2H), 2.81-2.71 (m, 1H), 2.19-2.09 (m, 1H), 2.04 (s, 3H), 2.02-1.97 (m, 1H), 1.90 (ddt, J=8.7, 5.2, 3.2 Hz, 2H), 1.61 (dt, J=13.2, 8.1 Hz, 1H), 1.41 (s, 9H). $^{13}$C NMR (125 MHz, DMSO-$d_6$) δ 169.76, 153.73, 135.50, 125.91, 114.18, 114.02, 81.33, 79.57, 78.91, 53.38, 51.93, 51.86, 41.98, 33.89, 33.10, 29.42, 28.45, 27.91, 20.64. HRMS (ESI-TOF) m/z: [M+H]$^+$ Calcd for $C_{21}H_{26}N_3O_4$ 384.1918; Found 384.1936; [M+Na]$^+$ Calcd for $C_{21}H_{25}N_3O_4Na$ 406.1737; Found 406.1754. $R_f$=0.13 (20% EtOAc in hexane)

j. 5-(BICYCLO[3.2.1]OCTA-2,6-DIEN-3-YL)-5,5-DICYANOPENT-2-YN-1-YL ACETATE (3K).

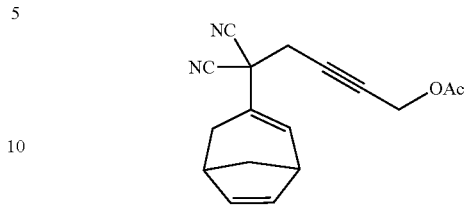

Yellow oil, 63% yield, 311 mg. Purified using 10% EtOAc in hexane. $^1$H NMR (500 MHz, CDCl$_3$) δ 6.68 (d, J=6.4 Hz, 1H), 6.21 (dt, J=5.7, 2.6 Hz, 1H), 5.80 (dt, J=5.7, 2.4 Hz, 1H), 4.69 (dd, J=14.5, 3.2 Hz, 2H), 2.94 (bs, 4H), 2.42 (ddt, J=17.7, 4.6, 2.3 Hz, 1H), 2.09 (d, J=3.1 Hz, 3H), 2.06-1.95 (m, 1H), 1.91 (d, J=17.6 Hz, 1H), 1.65 (dd, J=9.6, 2.4 Hz, 1H). $^{13}$C NMR (125 MHz, CDCl$_3$) δ 170.2, 139.0, 137.2, 131.3, 124.0, 113.6, 113.5, 81.3, 77.5, 52.0, 42.8, 40.2, 38.6, 37.7, 29.3, 27.4, 20.8. HRMS: (ESI-TOF) m/z: [M+H]$^+$ Calcd for $C_{17}H_{17}N_2O_2$ 281.1285; Found 281.1288. $R_f$=0.37 (20% EtOAc in hexane)

k. N-(4-(1,1-DICYANOBUT-3-YN-1-YL)CYCLO-HEX-3-EN-1-YL)ACETAMIDE (3L).

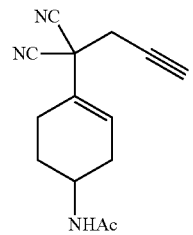 [SMILES: C#CCC(C#N)(C#N)C1=CCC(NC(C)=O)CC1]

Pale orange crystals, 72% yield, 1.7 g. Recrystalized in EtOH. $^1$H NMR (500 MHz, Methanol-$d_4$) δ 6.25 (ddt, J=4.6, 3.1, 1.5 Hz, 1H), 3.95 (dddd, J=10.4, 8.7, 5.5, 3.1 Hz, 1H), 3.25-3.13 (m, 2H), 2.85 (t, J=2.6 Hz, 1H), 2.59-2.49 (m, 1H), 2.35 (tdt, J=7.0, 4.2, 2.1 Hz, 2H), 2.17-1.93 (m, 5H), 1.69 (dddd, J=12.9, 10.5, 8.2, 6.9 Hz, 1H). $^{13}$C NMR (125 MHz, CD$_3$OD) δ 171.5, 127.9, 127.5, 113.8, 113.6, 75.2, 74.7, 43.9, 43.0, 30.7, 27.7, 27.4, 22.9, 21.3. HRMS: (ESI-TOF) m/z: [M+H]$^+$ Calcd for $C_{14}H_{16}N_3O$ 242.1288; Found 242.1293.

l. 2-(PROP-2-YN-1-YL)-2-(1,4-DIOXASPIRO[4.5]DEC-7-EN-8-YL)MALONONITRILE (3M).

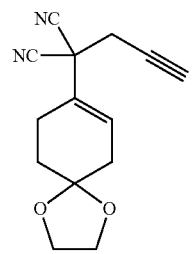 [SMILES: C#CCC(C#N)(C#N)C1=CCC2(CC1)OCCO2]

White solid, 96% yield, 5.9 g. Purified using 10% EtOAc in hexane. $^1$H NMR (500 MHz, CDCl$_3$) δ 6.19 (t, J=3.8 Hz, 1H), 3.98 (t, J=2.7 Hz, 4H), 2.98 (d, J=2.6 Hz, 2H), 2.45-2.36 (m, 5H), 1.85 (t, J=6.4 Hz, 2H). $^{13}$C NMR (126 MHz, cdcl3) δ 128.4, 126.9, 113.6, 106.5, 75.5, 74.7, 64.7, 43.0, 36.0, 30.9, 29.2, 24.1. HRMS: (ESI-TOF) m/z: [M+NH$_4$]$^+$ Calcd for C$_{14}$H$_{14}$N$_2$O$_2$Na 260.1394; Found 260.1390.

6. General Procedure for One-Pot Cope/α-Alkylation.

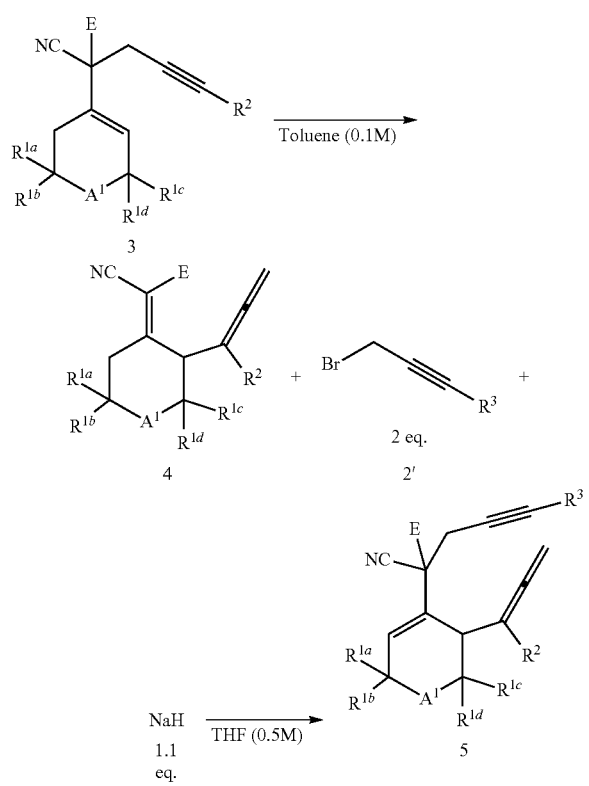

Enyne 3 was dissolved in toluene (unless otherwise specified) and N$_2$ was bubbled through the solution for five minutes. The solution was then heated using a pre-heated pie-block or oil bath in a screw cap pressure flask (temperatures and times are listed in Table 1). When the reaction was done, the solution was cooled to room temperature and the solvent was removed under reduced pressure. The percent conversion was calculated using $^1$H NMR (chemical shifts used for this determination are outlined in Table 1) and this was used to determine the stoichiometry for the propargylation step. The crude product from the Cope rearrangement was then re-dissolved in THF (0.5M with respect to allene 4) and added to a suspension of NaH (1.1 equivalent) in THF at 0° C. The propargyl bromide derivative 2' was then immediately added to the solution and the reaction was warmed to room temperature. Upon completion of the reaction (monitored by TLC), a saturated solution of NH$_4$Cl was added to quench the NaH and the crude material was taken up in ethyl acetate. The solution was then washed with H$_2$O and brine, dried with Na$_2$SO$_4$, and concentrated under reduced pressure. The compound was purified via column chromatography (hexane-ethyl acetate). Reaction temperatures, times, and conversion for enyne Cope rearrangement based on the enyne used in the reaction are given below in Table 7. Using the foregoing method, compounds 5aa, 5ac, 5aa, 5ad, 5bd, 5cd, 5dd, 5de, 5ed, 5fd, 5hd, 5id, 5jd, 5kd, 8a-8b, and 8e were prepared, and are described in further detail herein below.

TABLE 7

| Enyne | Temp (° C.) | Time (hrs.) | % conversion (3 to 4) | H$_{enyne}$ (ppm) | H$_{allene}$ (ppm) |
|---|---|---|---|---|---|
| 3a | 150 | 15 | 85 | 6.31 | 5.15, 4.88 |
| 3b | 170 | 6 | 37 | 6.11 | 5.17, 4.84 |
| 3c | 150 | 4.5 | 61 | 6.27 | 5.16, 4.88 |
| 3d | 150 | 1.5 | 56 | 6.34 | 5.23, 4.88 |
| 3e | 150 | 1 | 100 | 6.55 | 5.33, 4.86 |
| 3f | 150 | 2.5 | 91 | 6.68 | 5.22, 4.90 |
| 3h | 200 | 1.5 | 100 | 6.57 | 4.71 |
| 3i | 200 | 1.5 | 71 | 6.65 | 5.20 |
| 3j | 200 | 1.5 | 88 | 6.61 | 4.93 |
| 3k | 200 | 1.5 | 85 | 6.67 | 4.98 | a. 2-(6-(2λ5-PROPA-1,2-DIEN-1-YL)CYCLOHEX-1-EN-1-YL)-2-(PROP-2-YN-1-YL)MALONONITRILE (5AA).

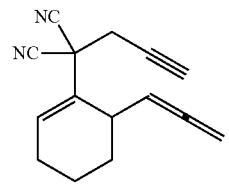

Pale yellow oil, 35% yield, 300 mg. Purified using 2% EtOAc in hexane, but could not be separated from unreacted enyne starting material. $^1$H NMR (500 MHz, CDCl$_3$) δ 6.36 (t, J=3.9 Hz, 1H), 5.19 (dd, J=14.8, 6.6 Hz, 1H), 4.83 (dt, J=6.5, 2.0 Hz, 2H), 3.12 (dd, J=16.6, 2.6 Hz, 1H), 3.07 (m, 1H), 3.01 (dd, J=16.7, 2.6 Hz, 1H), 2.35 (t, J=2.5 Hz, 1H), 2.28-2.10 (m, 2H), 1.85-1.55 (m, 4H). $^{13}$C NMR (125 MHz, CDCl$_3$) δ 209.2, 133.0, 128.9, 114.4, 114.2, 92.7, 77.2, 75.3, 75.1, 42.7, 35.8, 30.5, 29.8, 25.4, 16.8. HRMS (ESI-TOF) m/z: [M+H]$^+$Calcd for C$_{15}$H$_{15}$N$_2$ 223.1230; Found 223.1223. R$_f$=0.51 (20% EtOAc in hexane). Note: Cyclohexane was used as solvent for Cope rearrangement rather than toluene.

b. 2-(6-(2λ5-PROPRA-1,2-DIEN-1-YL)CYCLOHEX-1-EN-1-YL)-2-(BUT-2-YN-1-YL)MALONONITRILE (5AB).

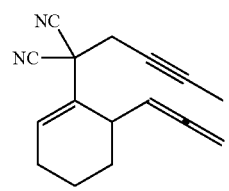

Pale yellow oil, 20% yield, 182 mg. Purified using 3% EtOAc in hexane, but could not be fully separated from minor impurities from the Cope rearrangement. $^1$H NMR (500 MHz, CDCl$_3$) δ 6.32 (dd, J=3.2, 3.5 Hz, 1H), 5.22-5.13 (m, 1H), 4.82 (dd, J=6.8, 2.5 Hz, 2H), 3.12-2.81 (m, 3H), 2.28-2.03 (m, 2H), 2.01-1.53 (m, 8H). $^{13}$C NMR (125 MHz, CDCl$_3$) δ 209.2, 132.5, 129.5, 114.8, 114.7, 92.8, 82.9, 77.4, 77.2, 77.2, 76.9, 70.6, 43.3, 35.8, 31.1, 29.9, 25.5, 16.9, 3.7. HRMS (ESI-TOF) mz: [M+H]$^+$ Calcd for C$_{16}$H$_{17}$N$_2$ 237.1386; Found 237.1386. R$_f$=0.39 (10% EtOAc in hexane). Note: Cyclohexane was used as solvent for Cope rearrangement rather than toluene.

c. 2-(6-(2λ5-PROPA-1,2-DIEN-1-YL)CYCLOHEX-1-EN-1-YL)-2-(3-PHENYLPROP-2-YN-1-YL)MALONONITRILE (5AC).

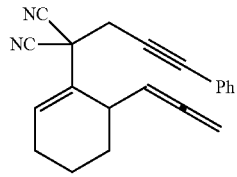

Pale yellow oil, 25% yield, 255 mg. Purified using 3% EtOAc in hexane. $^1$H NMR (600 MHz, CDCl$_3$) δ 7.50-7.41 (m, 2H), 7.38-7.28 (m, 3H), 6.41 (t, J=3.9 Hz, 1H), 5.23 (dt, J=8.0, 6.6 Hz, 1H), 4.86 (dtd, J=6.5, 3.6, 3.0, 1.8 Hz, 2H), 3.36 (d, J=16.7 Hz, 1H), 3.24 (d, J=16.7 Hz, 1H), 2.29-2.12 (m, 2H), 1.86-1.61 (m, 4H). $^{13}$C NMR (150 MHz, CDCl$_3$) δ 209.3, 132.9, 132.0, 129.2, 129.0, 128.5, 122.1, 114.7, 114.5, 92.8, 86.9, 80.6, 77.3, 43.0, 35.9, 31.6, 29.9, 25.5, 16.9. HRMS (ESI-TOF) m/z: [M+Na]$^+$ Calcd for C$_{21}$H$_{18}$N$_2$Na 321.1362; Found 321.1376. R$_f$=0.42 (10% EtOAc in hexane). Note: Cyclohexane was used as solvent for Cope rearrangement rather than toluene.

d. 5-(6-(2λ5-PROPA-1,2-DIEN-1-YL)CYCLOHEX-1-EN-1-YL)-5,5-DICYANOPENT-2-YN-1-YL ACETATE (5AD).

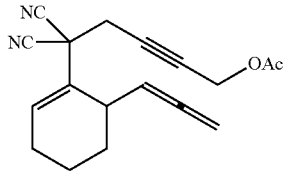

Pale yellow oil, 21% yield, 233 mg. Purified using gradient: 3% →10% EtOAc in hexane. $^1$H NMR (500 MHz, CDCl$_3$) δ 6.35 (t, J=3.9 Hz, 1H), 5.18 (q, J=7.0 Hz, 1H), 4.83 (dt, J=6.6, 2.0 Hz, 2H), 4.70 (t, J=2.1 Hz, 2H), 3.16 (dt, J=16.6, 2.1 Hz, 1H), 3.09-2.98 (m, 2H), 2.28-2.07 (m, 5H), 1.85-1.57 (m, 4H). $^{13}$C NMR (125 MHz, CDCl$_3$) δ 209.2, 170.2, 133.1, 129.0, 114.4, 114.2, 92.7, 80.9, 78.2, 77.3, 52.1, 42.7, 35.9, 30.9, 29.9, 25.5, 20.8, 16.8. HRMS (ESI-TOF) mz: [M+H]$^+$ Calcd for C$_{18}$H$_{19}$N$_2$O$_2$ 295.1441; Found 295.1444; [M+NH$_4$]$^+$ Calcd for C$_{18}$H$_{22}$N$_3$O$_2$ 312.1707; Found 312.1717; [M+Na]$^+$ Calcd for C$_{18}$H$_{18}$N$_2$O$_2$Na 317.1260; Found 317.1266. R$_f$=0.41 (20% EtOAc in hexane). Note: Cycohexane was used as solvent for Cope rearrangement rather than toluene.

e. METHYL 2-(6-(2λ5-PROPA-1,2-DIEN-1-YL)CYCLOHEX-1-EN-1-YL)-6-ACETOXY-2-CYANOHEX-4-YNOATE (5BD).

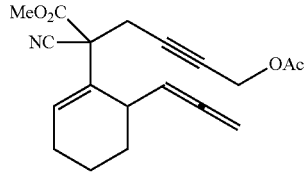

Pale yellow oil, 25% yield, 38 mg, d.r.=1:1.2. Purified using gradient: 5%→10% EtOAc in hexane. $^1$H NMR (500 MHz, CDCl$_3$): Diastereomer 1: δ 6.22 (s, 1H), 5.03 (dd, J=14.8, 6.8 Hz, 2H), 4.72 (m, 2H), 4.66 (m, 2H), 3.79 (s, 3H), 3.03-2.93 (m, 3H), 2.20-2.10 (m, 2H), 2.08 (s, 3H), 1.76-1.60 (m, 4H); Diastereomer 2: δ 6.10 (s, 1H), 5.13 (dd, J=14.9, 6.7 Hz, 2H), 4.74 (m, 2H), 4.66 (m, 2H), 3.82 (s, 3H), 3.09-2.93 (m, 3H), 2.20-2.10 (m, 2H), 2.08 (s, 3H), 1.76-1.60 (m, 4H). $^{13}$C NMR (125 MHz, CDCl$_3$): Diastereomer 1: δ 208.6, 170.3, 167.1, 131.5, 130.8, 117.8, 92.6, 80.7, 78.7, 76.5, 54.0, 53.9, 52.4, 34.8, 30.0, 27.1, 25.5, 20.9, 16.9; Diastereomer 2: δ 208.7, 170.3, 167.4, 131.5, 130.2, 117.8, 93.0, 80.7, 78.5, 76.5, 54.4, 54.0, 52.4, 36.0, 29.9, 27.7, 25.4, 20.9, 16.9. HRMS (ESI-TOF) m/z: [M+Na]$^+$ Calcd for C$_{19}$H$_{21}$NO$_4$Na 350.1363; Found 350.1380. R$_f$=0.33 (20% EtOAc in hexane).

f. 5,5-DICYANO-5-(4-METHYL-6-(2λ5-PROPA-1,2-DIEN-1-YL)CYCLOHEX-1-EN-1-YL)PENT-2-YN-1-YL ACETATE (5CD).

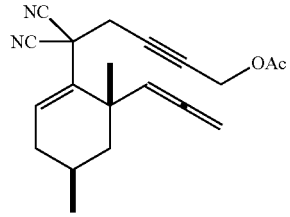

Yellow oil, 38% yield, 39 mg, d.r>20:1. Purified using 5% EtOAc in hexane. $^1$H NMR (500 MHz, CDCl$_3$) δ 6.30 (dd, J=4.8, 2.8 Hz, 1H), 5.20 (dd, J=14.6, 6.7 Hz, 1H), 4.84-4.79 (m, 2H), 4.68 (t, J=2.1 Hz, 2H), 3.15 (dt, J=16.6, 2.1 Hz, 1H), 3.08 (m, 1H), 3.02 (dt, J=16.6, 2.1 Hz, 1H), 2.30 (dt, J=18.7, 5.0 Hz, 1H), 2.08 (s, 3H), 1.87 (m, 1H), 1.79-1.70 (m, 2H), 1.47 (td, J=12.6, 5.1 Hz, 1H), 0.98 (d, J=6.6 Hz, 3H). $^{13}$C NMR (125 MHz, CDCl$_3$) δ 209.0, 170.2, 133.0, 128.9, 114.4, 114.2, 93.1, 81.0, 78.2, 77.4, 52.1, 42.5, 38.2, 36.6, 34.1, 31.1, 22.8, 21.5, 20.8. HRMS: (ESI-TOF) m/z: [M+Na]$^+$ Calcd for C$_{19}$H$_{20}$N$_2$O$_2$Na 331.1417; Found 331.1432; [2M+Na]$^+$ Calcd for C$_{19}$H$_{20}$N$_2$O$_2$ 639.2942; Found 639.2958. R$_f$=0.14 (10% EtOAc in hexane). Relative stereochemistry was determined by analysis of 6cd.

g. ETHYL 4-(5-ACETOXY-1,1-DICYANOPENT-3-YN-1-YL)-5-(2λ5-PROPA-1,2-DIEN-1-YL)CYCLOHEX-3-ENE-1-CARBOXYLATE (5DD).

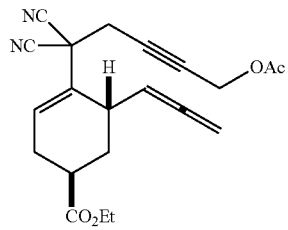

Yellow oil, 24% yield (679 mg)+29% recovered enyne starting material, d.r.>20:1. Purified using 15% EtOAc in hexane. $^1$H NMR (500 MHz, CDCl$_3$) δ 6.34 (dd, J=4.7, 3.0 Hz, 1H), 5.24 (q, J=6.8 Hz, 1H), 4.89 (qdd, J=11.2, 6.6, 2.1 Hz, 2H), 4.69 (t, J=2.0 Hz, 2H), 4.16 (q, J=7.2 Hz, 2H), 3.21-3.11 (m, 2H), 3.05 (dt, J=16.7, 2.1 Hz, 1H), 2.75 (dddd, J=13.3, 9.9, 6.1, 3.1 Hz, 1H), 2.51 (dt, J=19.1, 5.4 Hz, 1H), 2.39 (ddt, J=19.0, 10.7, 2.3 Hz, 1H), 2.10 (s, 4H), 1.86 (td, J=12.9, 4.9 Hz, 1H), 1.27 (t, J=7.2 Hz, 3H). $^{13}$C NMR (125 MHz, CDCl$_3$) δ 209.17, 174.62, 170.08, 131.14, 128.88, 114.06, 113.77, 92.12, 81.18, 78.04, 77.73, 60.85, 51.91, 41.96, 35.53, 33.86, 31.99, 31.24, 27.75, 20.64, 14.22. HRMS: (ESI-TOF) m/z: [M+Na]$^+$ Calcd for C$_{21}$H$_{22}$N$_2$O$_4$Na 367.1652; Found 367.1634. R$_f$=0.38 (30% EtOAc in hexane). Relative stereochemistry was assumed to be consistent with the results for 5cd.

h. ETHYL 4-(1,1-DICYANO-4-(TRIMETHYLSILYL)BUT-3-YN-1-YL)-5-(2λ5-PROPA-1,2-DIEN-1-YL)CYCLOHEX-3-ENE-1-CARBOXYLATE (5DE).

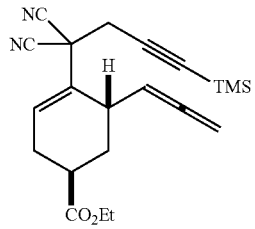

Pale yellow solid, 24% yield (641 mg)+37% recovered enyne starting material (744 mg), d.r.>20:1. Purified using 5% EtOAc in hexane. $^1$H NMR (500 MHz, CDCl$_3$) δ 6.33 (dd, J=4.7, 3.0 Hz, 1H), 5.24 (q, J=6.8 Hz, 1H), 4.96-4.83 (m, 2H), 4.17 (q, J=7.1 Hz, 2H), 3.21-3.16 (m, 1H), 3.12 (d, J=16.7 Hz, 1H), 3.02 (d, J=16.8 Hz, 1H), 2.75 (dtd, J=13.2, 6.4, 6.0, 3.1 Hz, 1H), 2.50 (dt, J=19.0, 5.5 Hz, 1H), 2.43-2.34 (m, 1H), 2.12 (dt, J=13.2, 2.8 Hz, 1H), 1.85 (td, J=12.9, 4.9 Hz, 1H), 1.28 (t, J=7.1 Hz, 3H), 0.18 (s, 9H). $^{13}$C NMR (125 MHz, CDCl$_3$) δ 209.34, 174.83, 130.96, 129.21, 114.32, 113.98, 110.13, 96.50, 93.12, 92.28, 78.17, 77.41, 77.16, 76.91, 60.98, 42.19, 35.71, 34.03, 32.40, 32.14, 27.87, 14.36, -0.20. HRMS: (ESI-TOF) m/z: [M+NH$_4$]$^+$ Calcd for C$_{21}$H$_{30}$N$_3$O$_2$Si 384.2102; Found 384.2090; [M+Na]$^+$ Calcd for C$_{21}$H$_{26}$N$_2$O$_2$SiNa 389.1656; Found 389.1648. R$_f$=0.5 (20% EtOAc in hexane). Relative stereochemistry was assumed to be consistent with the results for 5cd.

i. TERT-BUTYL 3-(5-ACETOXY-1,1-DICYANOPENT-3-YN-1-YL)-4-(2λ5-PROPA-1,2-DIEN-1-YL)-8-AZABICYCLO[3.2.1]OCT-2-ENE-8-CARBOXYLATE (5ED).

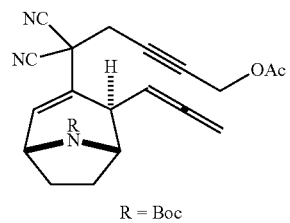

R = Boc

Pale yellow oil, 48% yield, 194 mg, d.r.>20:1. Purified using 10% EtOAc in hexane. $^1$H NMR (500 MHz, DMSO-d$_6$) δ 6.54 (d, J=5.4 Hz, 1H), 5.24 (dd, J=14.9, 6.6 Hz, 1H), 4.88 (ddd, J=11.0, 6.6, 1.6 Hz, 1H), 4.78 (ddd, J=11.0, 6.6, 1.6 Hz, 1H), 4.73 (t, J=2.1 Hz, 2H), 4.54 (t, J=5.6 Hz, 1H), 4.33 (d, J=7.8 Hz, 1H), 3.42 (ddt, J=30.0, 17.1, 2.1 Hz, 2H), 2.91 (d, J=8.1 Hz, 1H), 2.03 (s, 4H), 1.83 (t, J=10.7 Hz, 1H), 1.72 (dq, J=11.2, 6.0, 5.3 Hz, 1H), 1.65-1.57 (m, 1H), 1.40 (s, 9H). $^{13}$C NMR (125 MHz, DMSO-d$_6$) δ 209.3, 169.8, 152.8, 135.4, 127.7, 114.8, 114.4, 91.2, 81.3, 79.4, 79.2, 77.5, 57.4, 53.1, 51.9, 46.4, 40.6, 33.4, 29.7, 28.6, 27.9, 20.7. HRMS: (ESI-TOF) m/z: [M+H]$^+$ Calcd for C$_{24}$H$_{28}$N$_3$O$_4$ 444.1894; Found 444.1913. R$_f$=0.24 (20% EtOAc in hexane). Relative stereochemistry was determined by analysis of 9.

j. 5-(4-(2λ5-PROPA-1,2-DIEN-1-YL)BICYCLO[3.2.1]OCTA-2,6-DIEN-3-YL)-5,5-DICYANOPENT-2-YN-1-YL ACETATE (5FD).

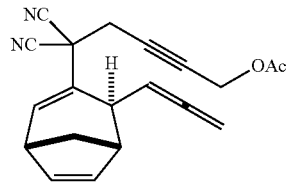

Pale yellow oil, 56% yield, 86 mg, d.r.>20:1. Purified using 7% EtOAc in hexane. $^1$H NMR (500 MHz, CDCl$_3$) δ 6.77 (d, J=6.6 Hz, 1H), 6.35 (dd, J=5.6, 2.9 Hz, 1H), 5.86 (dd, J=5.6, 2.9 Hz, 1H), 5.28 (dt, J=9.5, 6.6 Hz, 1H), 4.97-4.84 (m, 2H), 4.68 (t, J=2.1 Hz, 2H), 3.12 (dt, J=16.7, 2.1 Hz, 2H), 3.05 (dt, J=16.7, 2.1 Hz, 1H), 2.95 (m, 1H), 2.79 (m, 2H), 2.10 (s, 3H), 1.91-1.81 (m, 2H). $^{13}$C NMR (125 MHz, CDCl$_3$) δ 209.4, 170.2, 141.5, 140.0, 131.3, 125.8, 114.3, 114.1, 92.1, 81.1, 77.9, 77.2, 52.1, 46.0, 41.9, 39.7, 39.1, 36.2, 30.2, 20.8. HRMS: (ESI-TOF) m/z: [M+H]$^+$ Calcd for C$_{20}$H$_{19}$N$_2$O$_2$ 319.1441; Found 319.1447; [M+NH$_4$]$^+$ Calcd for C$_{20}$H$_{22}$N$_3$O$_2$ 336.1707; Found 336.1719; [M+Na]$^+$ Calcd for C$_{20}$H$_{18}$N$_2$O$_2$Na 341.1260; Found 341.1270. R$_f$=0.28 (20% EtOAc in hexane). Relative stereochemistry was determined by analysis of 10c k. TERT-BUTYL 3-(5-ACETOXY-1,1-DICYANO-PENT-3-YN-1-YL)-4-(3λ5-BUTA-2,3-DIEN-2-YL)-8-AZABICYCLO[3.2.1]OCT-2-ENE-8-CARBOXYLATE (5HD).

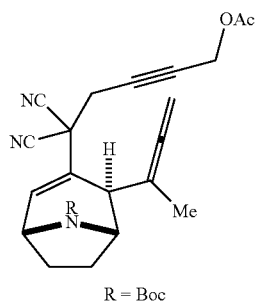

R = Boc

Pale yellow oil, 59% yield, 78 mg, d.r.>20:1. Purified using 20% EtOAc in hexane. $^1$H NMR (500 MHz, DMSO-d$_6$) δ 6.50 (d, J=5.3 Hz, 1H), 4.75 (m, 3H), 4.59 (ddd, J=9.9, 3.5, 1.9 Hz, 1H), 4.51 (t, J=5.5 Hz, 1H), 4.43 (d, J=7.7 Hz, 1H), 3.46 (dt, J=16.9, 2.1 Hz, 1H), 3.39 (dt, J=16.9, 2.1 Hz, 1H), 2.69 (d, J=2.2 Hz, 1H), 2.15-2.04 (m, 1H), 2.04 (s, 3H), 1.81 (h, J=3.3, 2.8 Hz, 4H), 1.74 (dq, J=11.4, 6.0, 5.4 Hz, 1H), 1.62 (dt, J=15.4, 8.3 Hz, 1H), 1.41 (s, 9H). $^{13}$C NMR (125 MHz, DMSO-d$_6$) δ 208.41, 169.83, 152.02, 134.34, 128.01, 114.97, 114.23, 99.22, 81.15, 79.46, 79.00, 77.12, 54.38, 51.94, 50.89, 36.84, 33.64, 30.92, 28.59, 27.95, 24.73, 20.70, 17.67. HRMS: (ESI-TOF) m/z: [M+Na]$^+$ Calcd for C$_{25}$H$_{29}$N$_3$O$_4$Na 458.2050; Found 458.2052. R$_f$=0.48 (50% EtOAc in hexane). Relative stereochemistry was determined by analysis of 9.

l. TERT-BUTYL 3-(5-ACETOXY-1,1-DICYANO-PENT-3-YN-1-YL)-4-(1-PHENYL-2λ5-PROPA-1,2-DIEN-1-YL)-8-AZABICYCLO[3.2.1]OCT-2-ENE-8-CARBOXYLATE (5ID).

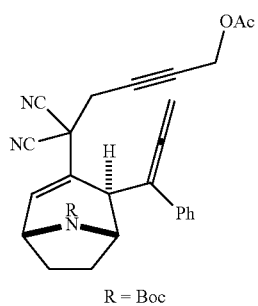

R = Boc

Yellow oil, 41% yield, 53 mg (+45% recovered starting material), d.r.>20:1. Purified using 20% EtOAc in hexane. $^1$H NMR (500 MHz, DMSO-d$_6$) δ 7.51 (d, J=7.8 Hz, 2H), 7.40 (t, J=7.8 Hz, 2H), 7.27 (t, J=7.4 Hz, 1H), 6.61 (d, J=5.3 Hz, 1H), 5.22 (d, J=12.2 Hz, 1H), 5.05 (d, J=12.0 Hz, 1H), 4.77 (t, J=2.1 Hz, 2H), 4.58 (t, J=5.3 Hz, 1H), 4.37 (d, J=8.0 Hz, 1H), 3.60-3.43 (m, 3H), 2.16-2.06 (m, 1H), 2.05 (s, 3H), 1.93-1.85 (m, 1H), 1.81-1.71 (m, 2H), 1.36-1.20 (bs, 9H). $^{13}$C NMR (125 MHz, DMSO-d$_6$) δ 209.4, 169.0, 151.1, 134.1, 128.0, 126.9, 126.6, 125.9, 114.1, 113.3, 105.3, 80.4, 78.6, 78.1, 54.5, 51.7, 51.1, 46.1, 40.0, 39.9, 39.7, 39.5, 39.4, 39.2, 39.0, 36.0, 32.9, 30.2, 27.5, 26.9, 19.8. HRMS: (ESI-TOF) m/z: [M+Na]$^+$ Calcd for C$_{30}$H$_{31}$N$_3$O$_4$Na 520.2207; Found 520.2232. R$_f$=0.28 (30% EtOAc in hexane). Relative stereochemistry was determined by analysis of 9.

m. TERT-BUTYL 3-(5-ACETOXY-1,1-DICYANO-PENT-3-YN-1-YL)-4-(1-ACETOXY-3l5-BUTA-2,3-DIEN-2-YL)-8-AZABICYCLO [3.2.1]OCT-2-ENE-8-CARBOXYLATE (5JD).

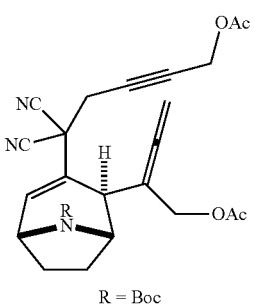

R = Boc

Yellow oil, 44% yield, 57 mg, d.r.>20:1. Purified using 25% EtOAc in hexane. $^1$H NMR (500 MHz, DMSO-d$_6$) δ 6.55 (d, J=5.3 Hz, 1H), 4.97 (dd, J=11.2, 2.1 Hz, 1H), 4.80 (dd, J=11.3, 1.9 Hz, 1H), 4.74 (s, 2H), 4.72 (dt, J=12.6, 2.5 Hz, 1H), 4.66 (dt, J=12.6, 2.5 Hz, 1H), 4.54 (t, J=5.5 Hz, 1H), 4.48 (d, J=7.9 Hz, 1H), 3.49 (dt, J=16.9.4, 2.0 Hz, 1H), 3.41 (dt, J=16.9, 1.9 Hz, 1H), 2.87 (s, 1H), 2.04 (m, 7H), 1.84 (t, J=10.4 Hz, 1H), 1.74 (dq, J=11.9, 6.2, 5.8 Hz, 1H), 1.62 (dt, J=15.2, 8.1 Hz, 1H), 1.41 (s, 9H). $^{13}$C NMR (125 MHz, DMSO-d$_6$) δ 208.86, 170.25, 169.83, 152.12, 135.18, 127.04, 114.88, 114.14, 100.30, 81.23, 79.54, 79.38, 79.19, 63.25, 55.23, 51.92, 47.10, 40.65, 40.48, 33.64, 30.52, 28.54, 27.78, 20.98, 20.69. HRMS: (DART) m/z: [M+H]$^+$ Calcd for C$_{27}$H$_{32}$N$_3$O$_6$ 494.2286; Found 494.2278. R$_f$=0.54 (50% EtOAc in hexane). Relative stereochemistry was determined by analysis of 9.

n. 2-(3-(5-ACETOXY-1,1-DICYANOPENT-3-YN-1-YL)BICYCLO[3.2.1]OCTA-3,6-DIEN-2-YL)-3λ5-BUTA-2,3-DIEN-1-YL ACETATE (5KD).

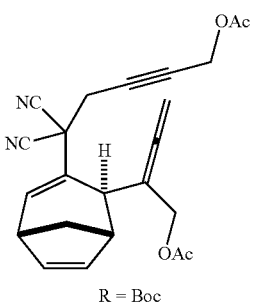

R = Boc

Yellow oil, 53% yield, 418 mg, d.r.>20:1. Purified using 15% EtOAc in hexane. $^1$H NMR (500 MHz, CDCl$_3$) δ 6.76 (dt, J=6.7, 1.0 Hz, 1H), 6.36 (dd, J=5.5, 2.8 Hz, 1H), 5.83 (dd, J=5.5, 3.0 Hz, 1H), 5.10 (m, 1H), 5.01 (m, 1H), 4.76-4.67 (m, 4H), 3.12 (dt, J=16.7, 2.1 Hz, 1H), 2.99 (dt, J=16.7, 2.1 Hz, 1H), 2.95-2.91 (m, 2H), 2.62 (p, J=1.3 Hz, 1H), 2.10 (d, J=5.0 Hz, 6H), 1.97 (d, J=10.3 Hz, 1H), 1.79

(dt, J=9.8, 4.7 Hz, 1H). $^{13}$C NMR (125 MHz, CDCl$_3$) δ 208.5, 170.8, 170.2, 142.3, 140.3, 131.1, 125.3, 114.4, 114.1, 101.6, 81.1, 80.5, 78.0, 64.3, 52.0, 44.7, 41.3, 40.7, 39.0, 35.4, 31.1, 21.1, 20.8. HRMS: (ESI-TOF) m/z: [M+Na]$^+$ Calcd for C$_{23}$H$_{22}$N$_2$O$_4$Na 413.1472; Found 413.1454. R$_f$=0.4 (30% EtOAc in hexane). Relative stereochemistry was determined by analysis of 10c.

o. TERT-BUTYL (E)-3-(1,1-DICYANO-4-PHENYLBUT-3-EN-1-YL)-4-(2λ5-PROPA-1,2-DIEN-1-YL)-8-AZABICYCLO[3.2.1] OCT-2-ENE-8-CARBOXYLATE (8A).

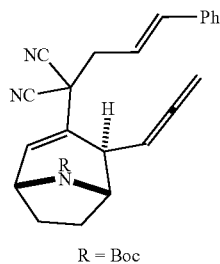

R = Boc

Pale yellow oil, 60% yield, 248 mg. Purified using 10% EtOAc in hexane. $^1$H NMR (500 MHz, DMSO-d$_6$) δ 7.45 (m, 2H), 7.41-7.35 (m, 2H), 7.33-7.28 (m, 1H), 6.78 (d, J=15.7 Hz, 1H), 6.55 (d, J=5.5 Hz, 1H), 6.17 (dt, J=15.7, 7.3 Hz, 1H), 5.29 (dt, J=8.2, 6.6 Hz, 1H), 4.91 (ddd, J=11.0, 6.7, 1.6 Hz, 1H), 4.83 (ddd, J=11.1, 6.6, 1.4 Hz, 1H), 4.57 (t, J=5.8, 1H), 4.36 (d, J=9.0, 1H), 3.18 (ddd, J=7.4, 2.5, 1.3 Hz, 2H), 2.95 (d, J=8.3, 1H), 2.12-2.01 (m, 1H), 1.81 (m, 1H), 1.73 (m, 1H), 1.62-1.53 (m, 1H), 1.42 (s, 9H). $^{13}$C NMR (125 MHz, DMSO-d$_6$) δ 208.4, 151.9, 136.5, 135.6, 134.0, 127.8, 127.4, 126.0, 119.9, 114.5, 114.1, 90.5, 78.6, 76.6, 56.6, 52.2, 45.7, 40.8, 32.6, 27.7, 27.6, 27.1. HRMS: (ESI-TOF) m/z: [M+Na]$^+$ Calcd for C$_{27}$H$_{29}$N$_3$O$_2$Na 450.2152; Found 450.2167. R$_f$=0.22 (20% EtOAc in hexane). Relative stereochemistry was determined by analysis of 9.

p. TERT-BUTYL (E)-3-(2-(Λ2-AZANYLIDENE)-1-CYANO-2λ3-ETHYLIDENE)-2-CINNAMYL-4-(2λ5-PROPA-1,2-DIEN-1-YL)-8-AZABICYCLO[3.2.1]OCTANE-8-CARBOXYLATE (8B).

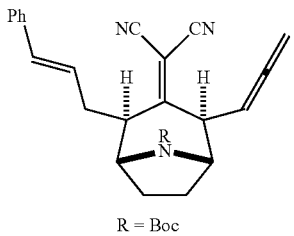

R = Boc

White solid, 23% yield, 94 mg. Purified using 10% EtOAc in hexane. $^1$H NMR (500 MHz, DMSO-d$_6$) δ 7.43-7.38 (m, 2H), 7.36-7.31 (m, 2H), 7.27-7.22 (m, 1H), 6.52 (d, J=15.8 Hz, 1H), 6.27 (dt, J=15.8, 7.2 Hz, 1H), 5.40 (td, J=6.7, 5.5 Hz, 1H), 5.02 (ddd, J=11.7, 6.8, 3.7 Hz, 1H), 4.95 (ddd, J=11.7, 6.7, 3.7 Hz, 1H), 4.47 (t, J=6.5 Hz, 2H), 3.68 (m, 1H), 2.99 (ddd, J=7.6, 6.1, 1.5 Hz, 1H), 2.66 (dddd, J=14.2, 8.6, 7.2, 1.3 Hz, 1H), 2.41-2.29 (m, 1H), 1.92 (ddt, J=7.3, 5.7, 2.5 Hz, 2H), 1.65-1.53 (m, 2H), 1.45 (s, 9H). $^{13}$C NMR (125 MHz, DMSO-d$_6$) δ 207.5, 180.9, 152.8, 136.5, 132.4, 128.1, 128.0, 127.7, 126.9, 126.0, 125.6, 111.1, 111.1, 89.0, 88.6, 79.1, 78.3, 56.6, 55.0, 50.2, 48.0, 36.9, 28.1, 27.7, 27.5. HRMS: (ESI-TOF) m/z: [M+Na]$^+$ Calcd for C$_{27}$H$_{29}$N$_3$O$_2$Na 450.2152; Found 450.2169. R$_f$=0.3 (20% EtOAc in hexane). Relative stereochemistry was determined by analysis of 8c.

q. TERT-BUTYL 3-(1,1-DICYANO-2-(5-(METHOXYCARBONYL)FURAN-2-YL)ETHYL)-4-(2λ5-PROPA-1,2-DIEN-1-YL)-8-AZABICYCLO[3.2.1]OCT-2-ENE-8-CARBOXYLATE (8E).

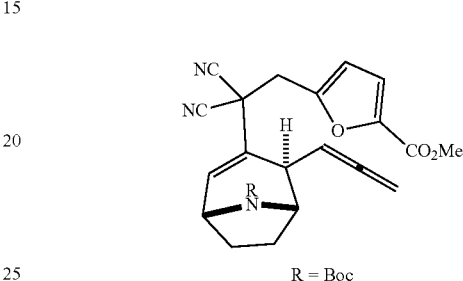

R = Boc

Colorless oil, 30% yield, 42.2 mg, d.r.>20:1. Purified using 25% EtOAc in hexane. $^1$H NMR (500 MHz, DMSO-d$_6$) δ 7.29 (d, J=3.4 Hz, 1H), 6.69 (d, J=3.5 Hz, 1H), 6.54 (d, J=5.5 Hz, 1H), 5.28 (q, J=7.1 Hz, 1H), 4.91 (dd, J=11.2, 6.7 Hz, 1H), 4.83 (dd, J=11.1, 6.7 Hz, 1H), 4.54 (t, J=5.7 Hz, 1H), 4.35 (d, J=8.0 Hz, 1H), 3.84 (d, J=11.6 Hz, 5H), 2.94 (d, J=8.4 Hz, 1H), 2.08-1.97 (m, 1H), 1.82-1.75 (m, 1H), 1.71 (dq, J=11.4, 6.0, 5.4 Hz, 1H), 1.56 (dt, J=14.8, 7.9 Hz, 1H), 1.42 (s, 9H). $^{13}$C NMR (125 MHz, DMSO-d$_6$) δ 209.30, 158.40, 152.25, 144.73, 135.29, 128.04, 119.49, 114.95, 114.50, 113.39, 91.28, 79.42, 77.55, 57.41, 52.15, 46.64, 40.82, 36.77, 33.25, 28.56, 27.85. HRMS: (ESI-TOF) m/z: [M+Na]$^+$ Calcd for C$_{25}$H$_{27}$N$_3$O$_5$Na 472.1843; Found 472.1846. R$_f$=0.32 (30% EtOAc in hexane). Relative stereochemistry was determined by analysis of 9.

r. TERT-BUTYL (E)-3-(2-(Λ2-AZANYLIDENE)-1-CYANO-2λ3-ETHYLIDENE)-2-((5-(METHOXYCARBONYL)FURAN-2-YL)METHYL)-4-(2λ5-PROPA-1,2-DIEN-1-YL)-8-AZABICYCLO[3.2.1] OCTANE-8-CARBOXYLATE (8F).

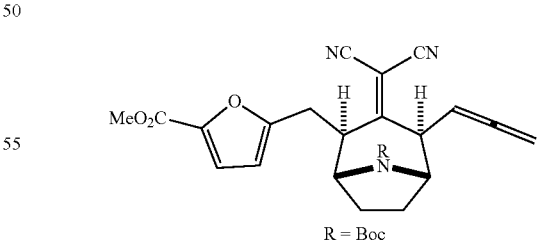

R = Boc

Yellow solid, 20% yield, 27.4 mg, d.r.>20:1. Purified using 25% EtOAc in hexane. $^1$H NMR (500 MHz, DMSO-d$_6$) δ 7.23 (d, J=3.6, 1H), 6.47 (d, J=3.4 Hz, 1H), 5.43 (m, 1.1 Hz, 1H), 5.11-5.00 (m, 2H), 4.49 (d, J=4.7 Hz, 1H), 4.42 (d, J=5.5 Hz, 1H), 3.81 (s, 3H), 3.70 (m, 1H), 3.22-3.13 (m, 2H), 2.92-2.82 (m, 1H), 1.97-1.88 (m, 2H), 1.68-1.53 (m, 2H), 1.44 (s, 9H). $^{13}$C NMR (125 MHz, DMSO-d$_6$) δ 207.5, 178.8, 157.8, 155.8, 152.9, 142.9, 118.8, 111.0, 110.3, 110.0, 89.5, 88.9, 79.3, 78.4, 56.7, 55.6, 51.0, 48.3, 47.9, 40.0, 39.9, 39.7, 39.5, 39.4, 39.2, 39.0, 31.6, 27.8, 27.6, 27.4. HRMS: (ESI-TOF) m/z: $[M+NH_4]^+$ Calcd for $C_{25}H_{31}N_4O_5$ 367.2289; Found 367.2310. $R_f$=0.48 (30% EtOAc in hexane). Relative stereochemistry was determined by analysis of 8c.

7. General Procedure for One-Pot Cope/Alkylidene Reduction/α-Alkylation

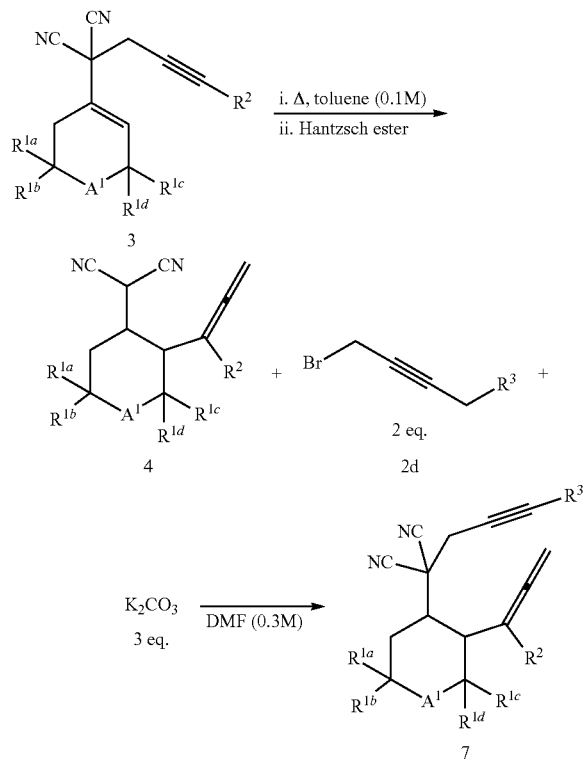

Enyne 3 was dissolved in toluene and 2 equivalents of Hantzsch ester were added. The solution was then heated using a pre-heated pie-block in a screw cap pressure flask (temperatures and times are listed in Table 2). When the reaction was done, the solution was cooled to room temperature and the solvent was removed under reduced pressure. The crude product from the Cope rearrangement was then re-dissolved in DMF (0.3 M with respect to allene 4) and added to a suspension of $K_2CO_3$ (3 equivalent) in DMF. The propargyl bromide derivative 2' was then immediately added to the solution and the reaction was warmed to room temperature. Upon completion of the reaction (monitored by TLC), the crude material was taken up in ethyl acetate. The solution was then washed with $H_2O$ (×3) and brine, dried with $Na_2SO_4$, and concentrated under reduced pressure. The compound was purified via column chromatography (hexane-ethyl acetate). Reaction temperatures, times, and conversion for enyne Cope rearrangement/alkylidene reduction based on the enyne used in the reaction are given below in Table 8. Using the foregoing method, compounds 7ad, 7dd, 7Ld, and 7md were prepared, and are described in further detail herein below.

TABLE 8

| Enyne | Temp (° C.) | Time (hrs.) |
|---|---|---|
| 3a | 140 | 4 |
| 3b | 130 | 16 |
| 3l | 130 | 16 |
| 3m | 130 | 16 | a. 5-(2-(2λ5-PROPA-1,2-DIEN-1-YL)CYCLO-HEXYL)-5,5-DICYANOPENT-2-YN-1-YL ACETATE (7AD).

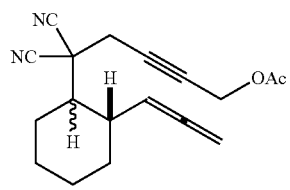

Pale yellow oil, 48% yield, 76 mg, 2:1 dr. Purified using 10% EtOAc in hexane. H NMR (500 MHz, $CDCl_3$) δ 5.44-5.11 (m, 1H), 4.94-4.76 (m, 2H), 4.76-4.71 (m, 2H), 3.25-2.81 (m, 2H), 2.33-2.17 (m, 1H), 2.12 (s, 4H), 2.05-1.81 (m, 3H), 1.81-1.45 (m, 2H), 1.43-1.22 (m, 4H). $^{13}C$ NMR (125 MHz, $CDCl_3$) δ 209.4, 208.8, 170.1, 115.0, 114.3, 93.0, 86.7, 80.9, 80.8, 77.9, 77.6, 76.0, 75.5, 52.0, 52.0, 46.2, 45.2, 42.5, 41.1, 36.5, 34.6, 32.7, 28.3, 27.8, 26.8, 25.8, 25.5, 25.0, 23.9, 20.7, 20.0. HRMS: (ESI-TOF) m/z: $[M+Na]^+$ Calcd for $C_{18}H_{20}N_2O_2Na$ 319.1417; Found 319.1422.

b. ETHYL 4-(5-ACETOXY-1,1-DICYANOPENT-3-YN-1-YL)-3-(2λ5-PROPA-1,2-DIEN-1-YL)CY-CLOHEXANE-1-CARBOXYLATE (7DD).

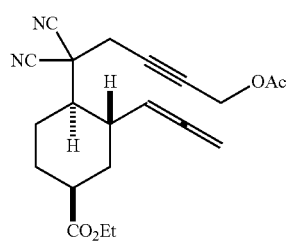

25%

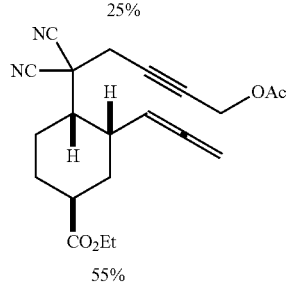

55%

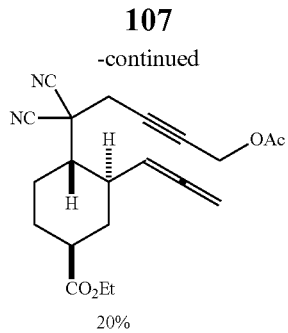

20%

Pale yellow oil, 49% yield, 70 mg, ~2:1:1 dr. Purified using 15% EtOAc in hexane. $^1$H NMR (500 MHz, CDCl$_3$) δ 5.41-5.08 (m, 1H), 4.96-4.78 (m, 2H), 4.70 (m, 2H), 4.26-4.08 (m, 2H), 3.28-2.89 (m, 2H), 2.78-1.87 (m, 9H), 1.77 (dtd, J=19.9, 13.1, 4.0 Hz, 1H), 1.68-1.44 (m, 2H), 1.42-1.16 (m, 5H). $^{13}$C NMR (125 MHz, cdcl3) δ 209.6, 208.9, 208.8, 174.7, 174.2, 173.8, 170.1, 114.8, 114.7, 114.5, 114.1, 114.0, 113.6, 92.5, 92.1, 86.1, 81.2, 81.1, 81.0, 77.8, 77.6, 77.3, 76.6, 76.5, 76.1, 60.7, 60.6, 52.0, 51.9, 45.5, 45.4, 44.3, 41.9, 41.6, 40.8, 40.6, 40.3, 38.1, 38.0, 37.1, 36.5, 36.0, 35.0, 34.6, 28.2, 28.0, 27.7, 27.6, 27.5, 27.0, 26.1, 24.5, 22.9, 20.7, 14.2. Relative stereochemistry and dr was determined using COSY, gHSQC, gHMBC, gHSQCTOCSY, and TOCSY. HRMS: (ESI-TOF) m/z: [M+Na]$^+$ Calcd for C$_{21}$H$_{24}$N$_2$O$_4$Na 391.1628; Found 391.1637.

c. 5-(4-ACETAMIDO-2-(2λ5-PROPA-1,2-DIEN-1-YL)CYCLOHEXYL)-5,5-DICYANOPENT-2-YN-1-YL ACETATE (7LD).

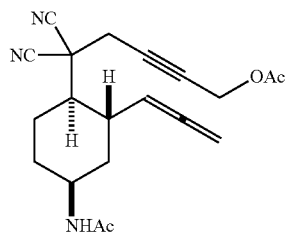

Pale yellow oil, 68% yield, >20:1 dr. Purified using 100% EtOAc. $^1$H NMR (500 MHz, CDCl$_3$) δ 5.90 (d, J=7.1 Hz, 1H), 5.12 (dt, J=9.2, 6.6 Hz, 1H), 4.88 (dddd, J=33.2, 11.3, 6.6, 1.2 Hz, 2H), 4.71 (t, J=2.1 Hz, 2H), 4.20 (dp, J=8.0, 3.9 Hz, 1H), 3.21 (dt, J=17.0, 2.1 Hz, 1H), 3.09 (dt, J=16.9, 2.1 Hz, 1H), 2.58-2.39 (m, 1H), 2.16-1.81 (m, 10H), 1.73-1.46 (m, 2H). $^{13}$C NMR (125 MHz, CDCl$_3$) δ 208.8, 170.3, 169.9, 114.9, 114.3, 92.4, 81.4, 77.6, 77.4, 77.1, 77.0, 76.9, 52.1, 45.3, 43.7, 40.6, 37.3, 37.0, 28.9, 28.2, 23.6, 23.1, 20.8. Relative stereochemistry determined using HSQC, HMBC, and TOCSY (2.46, 5.12, and 5.90 ppm). HRMS: (ESI-TOF) m/z: [M+Na]$^+$ Calcd for C$_{20}$H$_{23}$N$_3$O$_3$Na 376.1647; Found 376.1647.

d. 5-(7-(2λ5-PROPA-1,2-DIEN-1-YL)-1,4-DIOXASPIRO[4.5]DECAN-8-YL)-5,5-DICYANOPENT-2-YN-1-YL ACETATE (7MD).

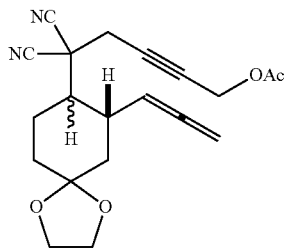

Pale yellow oil, 57% yield, 83 mg, 1.5:1 dr. Purified using 20% EtOAc in hexane. $^1$H NMR (500 MHz, CDCl$_3$) δ 5.78-5.12 (m, 1H), 4.99-4.68 (m, 4H), 4.13-3.90 (m, 4H), 3.32-2.87 (m, 2H), 2.73-2.20 (m, 1H), 2.17-1.81 (m, 7H), 1.74-1.57 (m, 2H), 1.27 (s, 1H). $^{13}$C NMR (125 MHz, CDCl$_3$) δ 209.0, 209.0, 170.1, 114.8, 114.7, 114.0, 113.7, 107.3, 106.8, 91.9, 87.9, 81.1, 81.0, 77.7, 77.5, 76.6, 75.1, 64.6, 64.6, 64.5, 64.1, 52.0, 52.0, 45.3, 44.2, 42.2, 40.4, 40.2, 39.9, 39.7, 37.3, 34.4, 34.0, 27.9, 26.9, 25.8, 21.9, 20.7. HRMS: (ESI-TOF) m/z: [M+Na]$^+$ Calcd for C$_{20}$H$_{22}$N$_2$O$_4$Na 377.1472; Found 377.1483.

8. General Procedure for One-Pot Cope Rearrangement/Tsuj-Trost Allylation.

Enyne 3e was dissolved in toluene (0.1 M with respect to the enyne) and N$_2$ was bubbled through the solution for five minutes. The solution was then heated to 150° C. for 1 hour using microwave irradiation. When the reaction was done, the solution was cooled to room temperature and the solvent was removed under reduced pressure. The crude product from the Cope rearrangement was then re-dissolved in THF (0.5 M with respect to allene 4e) and added to a suspension of NaH (1.1 equivalent) in THF at 0° C. The allyl acetate electrophile (2 eq) and Pd(PPh$_3$)$_4$ (5 mol %) were then added to the solution and the reaction was warmed to room temperature. Upon completion of the reaction (monitored by TLC, 30 min-2 hours), a saturated solution of NH$_4$Cl was added to quench the NaH and the crude material was extracted with ethyl acetate. The organic layer was then washed with H$_2$O and brine, dried with Na$_2$SO$_4$, and concentrated under reduced pressure. The compound was then purified via column chromatography (hexane-ethyl acetate).

a. TERT-BUTYL (Z)-3-(2-(λ2-AZANYLIDENE)-1-CYANO-2λ3-ETHYLIDENE)-2-(1-PHENYLALLYL)-4-(2λ5-PROPA-1,2-DIEN-1-YL)-8-AZABICYCLO[3.2.1]OCTANE-8-CARBOXYLATE (8C).

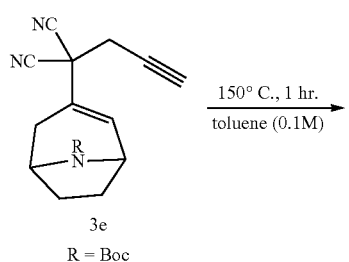

3e
R = Boc

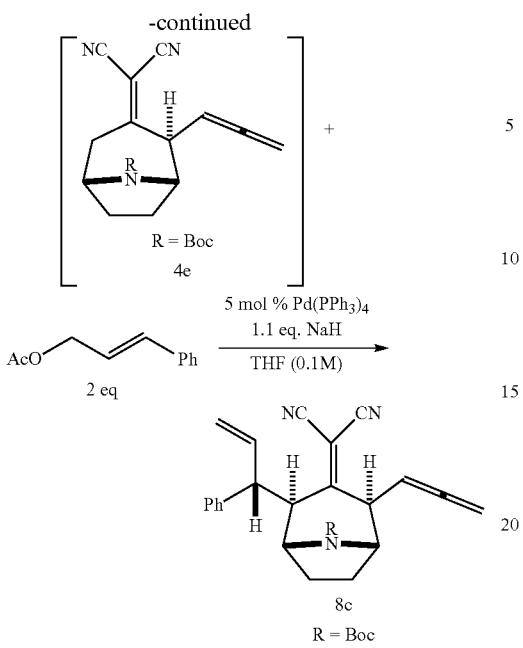

Colorless oil, 61% yield, 83 mg, d.r>20:1. Purified using 10% EtOAc in hexane. $^1$H NMR (500 MHz, DMSO-$d_6$) δ 7.42-7.37 (m, 2H), 7.35-7.32 (m, 2H), 7.31-7.27 (m, 1H), 5.91 (ddd, J=17.0, 10.2, 9.0 Hz, 1H), 5.39 (q, J=6.9 Hz, 1H), 5.11-5.03 (m, 2H), 5.01-4.89 (m, 2H), 4.49 (d, J=7.0 Hz, 1H), 4.08 (d, J=7.1 Hz, 1H), 3.74-3.65 (m, 2H), 3.27 (d, J=11.2 Hz, 1H), 1.86-1.68 (m, 2H), 1.62-1.45 (m, 2H), 1.37 (s, 9H). $^{13}$C NMR (125 MHz, DMSO-$d_6$) δ 209.1, 180.2, 154.5, 141.5, 138.7, 129.3, 128.5, 127.4, 117.7, 112.7, 111.9, 90.5, 88.6, 80.2, 78.6, 58.6, 55.7, 55.5, 53.7, 49.0, 28.6, 28.4, 28.1. HRMS: (ESI-TOF) m/z: [M+Na]$^+$ Calcd for $C_{27}H_{29}N_3O_2Na$ 450.1252; Found 450.2171. $R_f$=0.6 (30% EtOAc in hexane).

Note: Relative stereochemistry generated during the allylation is inferred by comparison to the product of the Cope rearrangement of 8a (reaction details shown below). This was done based on results previously published by our group[7] regarding the diastereoselective Cope rearrangement and NOE confirming the stereochemistry of the ring.

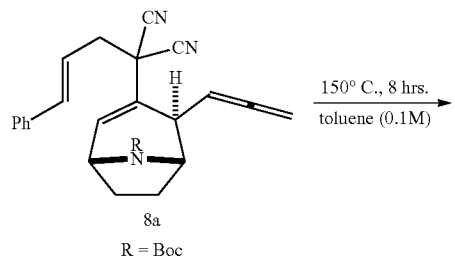

Procedure: Enyne 8a (30 mg, 70.17 μmol) was dissolved in toluene (0.1 M) and $N_2$ was bubbled through the solution for five minutes. The solution was then heated to 150° C. for 8 hours using microwave irradiation. When the reaction was done, the solution was cooled to room temperature and the solvent was removed under reduced pressure. The crude product was purified via column chromatography (10% EtOAc in hexane) to afford 8c in 71% yield (21.3 mg).

b. TERT-BUTYL 3-((3E,5E)-1,1-DICYANO-HEPTA-3,5-DIEN-1-YL)-4-(2λ5-PROPA-1,2-DIEN-1-YL)-8-AZABICYCLO[3.2.1] OCT-2-ENE-8-CARBOXYLATE (8D).

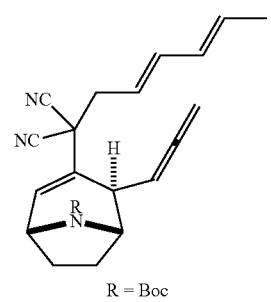

Yellow oil, 41% yield, 52 mg. Purified using 10% EtOAc in hexane. $^1$H NMR (500 MHz, DMSO-$d_6$) δ 6.49 (d, J=5.4 Hz, 1H), 6.33 (dd, J=15.1, 10.3 Hz, 1H), 6.19-6.09 (m, 1H), 5.80 (dq, J=13.8, 6.7 Hz, 1H), 5.51 (dt, J=14.9, 7.2 Hz, 1H), 5.26 (dt, J=8.1, 6.6 Hz, 1H), 4.89 (ddd, J=11.0, 6.7, 1.6 Hz, 1H), 4.81 (ddd, J=11.1, 6.6, 1.4 Hz, 1H), 4.55 (t, J=5.4 Hz, 1H), 4.35 (d, J=7.7 Hz, 1H), 3.00 (dd, J=7.4, 3.4 Hz, 2H), 2.89 (d, J=8.0 Hz, 1H), 2.06 (dddd, J=13.2, 10.5, 7.9, 2.3 Hz, 1H), 1.86-1.78 (m, 1H), 1.78-1.69 (m, 4H), 1.62-1.51 (m, 1H), 1.47-1.36 (m, 9H). $^{13}$C NMR (125 MHz, DMSO-$d_6$) δ 208.4, 151.9, 136.9, 133.8, 130.5, 130.1, 127.5, 120.3, 114.5, 114.1, 90.5, 78.5, 76.5, 56.6, 54.3, 45.7, 40.9, 40.6, 40.0, 39.9, 39.8, 39.7, 39.6, 39.5, 39.4, 39.4, 39.2, 39.0, 32.6, 27.7, 27.1, 17.2. HRMS: (ESI-TOF) m/z: [M+Na]$^+$ Calcd for $C_{24}H_{29}N_5O_2Na$ 414.2152; Found 414.2155. $R_f$=0.4 (20% EtOAc in hexane). Relative stereochemistry was determined by analysis of 8.

9. General Procedure for Pauson-Khand Reaction.

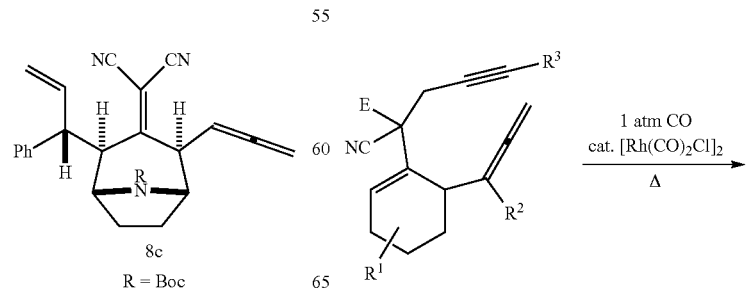

-continued

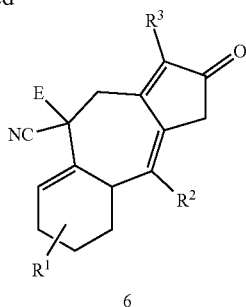

6

Procedure 1: A flame-dried Schlenk flask was charged with 5 mol % [Rh(CO)$_2$Cl]$_2$ and the flask was evacuated and refilled with CO gas. The allenyne 5 and toluene (0.01 M with respect to 5) were then added to the flask and a full balloon of CO gas was bubbled through the solution. The balloon was then replaced with a second full balloon of CO gas and the reaction was heated to 90° C. When the reaction was complete (monitored by TLC, 6-18 hrs) the solution was cooled to room temperature and solvent was removed under reduced pressure. The product was purified using column chromatography (hexane-ethyl acetate).

Procedure 2: A flame-dried Schlenk flask was charged with a solution of allenyne 5 in p-xylenes (0.005 M) under nitrogen. A full balloon of CO was then bubbled through the solution before being replaced with a second balloon of CO. The [Rh(CO)$_2$Cl]$_2$ catalyst (10 mol %) was then added to the reaction under an atmosphere of CO gas. The reaction was then heated to 110° C. using a preheated oil bath. Upon completion of the reaction (monitored by TLC, 6-18 hrs) the solution was cooled to room temperature and solvent was removed under reduced pressure. The product was purified using column chromatography (hexane-ethyl acetate).

Using the foregoing methods, compounds 6aa, 6cd, 6dd, 6de, 6ed, 6hd, 6jd, 6kd, and 6md were prepared, and are described in further detail herein below.

a. 2-OXO-2,4a,5,6,7,10-HEXAHYDROBENZO[F]AZULENE-9,9(3H)-DICARBONITRILE (6AA).

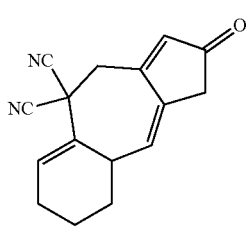 [SMILES: N#CC1(C#N)CC2=CC(=O)CC2=CC2CCCC=C21]

Orange oil, 52% yield via procedure 2, 47 mg (30% yield via procedure 1). Purified using 40% EtOAc in hexane. $^1$H NMR (500 MHz, CDCl$_3$) δ 6.40 (t, J=3.9 Hz, 1H), 6.26 (s, 1H), 5.74 (s, 1H), 3.67 (d, J=15.5 Hz, 1H), 3.46 (s, 1H), 3.35 (d, J=15.5 Hz, 1H), 3.05 (dd, J=30.2, 21.1 Hz, 2H), 2.19 (m, 2H), 1.88 (dt, J=8.1, 3.8 Hz, 2H), 1.73 (dp, J=13.9, 4.7 Hz, 1H), 1.58 (tt, J=13.5, 7.5 Hz, 1H). $^{13}$C NMR (125 MHz, CDCl$_3$) δ 203.4, 162.0, 136.3, 136.2, 132.7, 132.2, 131.2, 114.7, 114.4, 41.9, 39.9, 39.5, 35.4, 29.7, 25.3, 18.0. HRMS: (ESI-TOF) m/z: [M+H]$^+$ Calcd for C$_{16}$H$_{15}$N$_2$O 251.1179; Found 251.1173; [M+Na]$^+$ Calcd for C$_{16}$H$_{14}$N$_2$ONa 273.0998; Found 273.1010. R$_f$=0.53 (50% EtOAc in hexane)

b. (9,9-DICYANO-6-METHYL-2-OXO-2,3,3A,4,4A,5,6,7,9,10-DECAHYDROBENZO[F]AZULEN-1-YL)METHYL ACETATE (6CD).

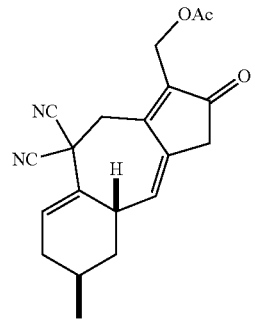

Yellow oil, 32% yield, 35 mg, d.r>20:1 (via procedure 1). Purified using 20% EtOAc in hexane. $^1$H NMR (500 MHz, CDCl$_3$) δ 6.35 (dd, J=5.0, 2.3 Hz, 1H), 5.84 (d, J=3.3 Hz, 1H), 4.88 (d, J=12.9 Hz, 1H), 4.80 (d, J=13.0 Hz, 1H), 3.69 (d, J=15.5 Hz, 1H), 3.61 (d, J=15.5 Hz, 1H), 3.53 (s, 1H), 3.14-2.99 (m, 2H), 2.28 (dt, J=17.9, 4.6 Hz, 1H), 2.07 (s, 3H), 1.89 (dt, J=14.3, 2.5 Hz, 1H), 1.81 (dt, J=10.4, 2.4 Hz, 1H), 1.78-1.68 (m, 2H), 1.58 (td, J=12.5, 5.1 Hz, 1H), 1.03 (d, J=6.0 Hz, 3H). $^{13}$C NMR (125 MHz, CDCl$_3$) δ 201.83, 170.72, 159.66, 141.10, 135.96, 134.64, 132.14, 130.96, 114.77, 114.67, 54.42, 40.61, 38.97, 37.74, 36.94, 35.45, 33.74, 23.87, 21.35, 20.86. HRMS: (ESI-TOF) m/z: [M+H]$^+$ Calcd for C$_{20}$H$_{21}$N$_2$O$_3$ 337.1547; Found 337.1541. HSQC, HMBC, and NOESY used to determine relative stereochemistry.

c. ETHYL 1-(ACETOXYMETHYL)-9,9-DICYANO-2-OXO-2,3,4A,5,6,7,9,10-OCTAHYDROBENZO[F]AZULENE-6-CARBOXYLATE (6DD).

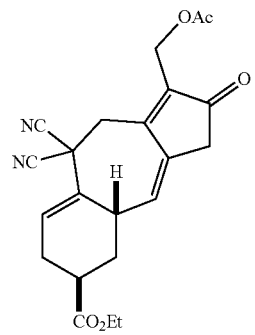

Orange solid, 41-44% yield (26-220 mg) (via procedure 1). Purified using 40% EtOAc in hexane. $^1$H NMR (500 MHz, CDCl$_3$) δ 6.39 (t, J=3.8 Hz, 1H), 5.84 (d, J=3.2 Hz, 1H), 4.88 (d, J=13.0 Hz, 1H), 4.81 (d, J=13.0 Hz, 1H), 4.18 (q, J=7.2 Hz, 2H), 3.70 (d, J=15.5 Hz, 1H), 3.64 (d, J=15.6 Hz, 2H), 3.12 (d, J=21.1 Hz, 1H), 3.05 (d, J=21.6 Hz, 1H), 2.64-2.55 (m, 1H), 2.50 (dt, J=19.0, 5.4 Hz, 1H), 2.47-2.39

(m, 1H), 2.26 (dt, J=13.7, 2.8 Hz, 1H), 2.07 (s, 3H), 1.98 (td, J=13.0, 5.2 Hz, 1H), 1.28 (t, J=7.1 Hz, 3H). $^{13}$C NMR (125 MHz, CDCl$_3$) δ 201.6, 174.0, 170.8, 159.1, 141.8, 136.9, 132.8, 131.3, 130.6, 114.6, 114.4, 61.2, 54.5, 40.8, 39.1, 37.2, 35.1, 34.9, 32.1, 27.8, 21.0, 14.3. HRMS (ESI-TOF) m/z: [M+H]$^+$ Calcd for C$_{22}$H$_{23}$N$_2$O$_5$ 395.1601; Found 395.1593; [M+Na]$^+$ Calcd for C$_{22}$H$_{22}$N$_2$O$_5$Na 417.1421; Found 417.1418. R$_f$=0.42 (50% EtOAc in hexane). Relative stereochemistry is assumed to be consistent with 6cd.

d. ETHYL 9,9-DICYANO-2-OXO-1-(TRIMETHYLSILYL)-2,3,4A,5,6,7,9,10-OCTAHYDROBENZO[F]AZULENE-6-CARBOXYLATE (6DE).

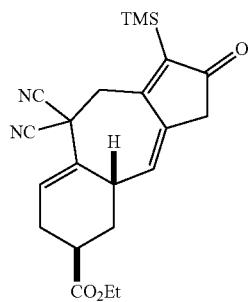

Orange oil, 48% yield, 52 mg (via procedure 1). Purified using 20% EtOAc in hexane. $^1$H NMR (500 MHz, CDCl$_3$) δ 6.37 (s, 1H), 5.74 (s, 1H), 4.20 (qd, J=7.0, 6.4, 1.2 Hz, 2H), 3.74-3.48 (m, 3H), 3.03 (dd, J=23.3, 20.5 Hz, 2H), 2.72-2.57 (m, 1H), 2.57-2.34 (m, 2H), 2.32-2.22 (m, 1H), 1.96 (m, 1H), 1.30 (t, J=7.0 3H), 0.33 (s, 9H). $^{13}$C NMR (125 MHz, CDCl$_3$) δ 207.9, 174.2, 166.5, 150.0, 140.5, 131.7, 130.3, 130.0, 114.9, 77.4, 77.2, 76.9, 61.1, 42.1, 39.1, 37.6, 34.8, 33.9, 32.1, 27.7, 14.3, −0.2. HRMS: (ESI-TOF) m/z: [M+Na]$^+$ Calcd for C$_{22}$H$_{26}$N$_2$O$_3$SiNa 417.1605; Found 417.1613. R$_f$=0.58 (40% EtOAc in hexane). Relative stereochemistry is assumed to be consistent with 6cd.

e. TERT-BUTYL 1-(ACETOXYMETHYL)-10,10-DICYANO-2-OXO-3,4A,5,6,7,8,10,11-OCTAHYDRO-2H-5,8-EPIMINOCYCLO PENTA[B]HEPTALENE-12-CARBOXYLATE (6ED).

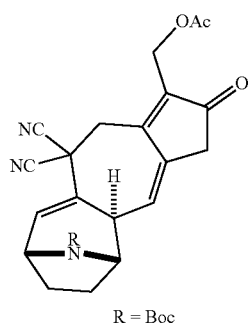

Orange solid, 75% yield, 68 mg (via procedure 1). Purified using 35% EtOAc in hexane. $^1$H NMR (500 MHz, DMSO-d$_6$) δ 6.63 (d, J=5.5 Hz, 1H), 6.13 (d, J=3.3 Hz, 1H), 4.80 (s, 2H), 4.58 (d, J=8.0 Hz, 1H), 4.54 (t, J=5.7 Hz, 1H), 4.01 (d, J=15.7 Hz, 1H), 3.78 (d, J=15.7 Hz, 1H), 3.63 (s, 1H), 3.17 (d, J=21.2 Hz, 1H), 2.97 (d, J=21.3 Hz, 1H), 2.20-2.10 (m, 1H), 2.00 (s, 3H), 1.88 (dd, J=11.8, 9.2 Hz, 1H), 1.78 (ft, J=11.7, 6.4 Hz, 1H), 1.73-1.64 (m, 1H), 1.41 (s, 9H). $^{13}$C NMR (125 MHz, DMSO-d$_6$) δ 200.8, 169.5, 159.8, 140.0, 134.5, 133.6, 130.7, 130.0, 114.5, 114.5, 79.0, 59.2, 56.2, 53.6, 44.9, 39.8, 37.5, 34.4, 32.2, 27.6, 27.1, 20.0. HRMS (ESI-TOF) m/z: [M+H]$^+$ Calcd for C$_{25}$H$_{28}$N$_3$O$_5$ 450.2023; Found 450.2012; [M+Na]$^+$ Calcd for C$_{25}$H$_{27}$N$_3$O$_5$Na 472.1843; Found 472.1837. R$_f$=0.2 (40% EtOAc in hexane). Relative stereochemistry was determined based on analysis of 8.

f. TERT-BUTYL 1-(ACETOXYMETHYL)-10,10-DICYANO-4-METHYL-2-OXO-3,4A,5,6,7,8,10,11-OCTAHYDRO-2H-5,8-EPIMINO CYCLOPENTA[B]HEPTALENE-12-CARBOXYLATE (6HD).

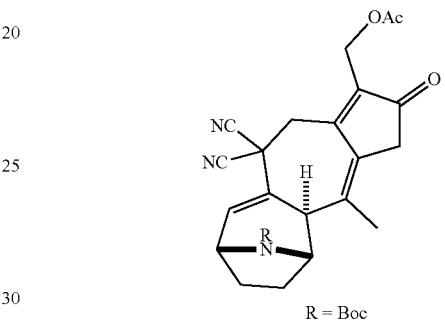

Brown oil, 29% yield, 15.4 mg (via procedure 1). Purified using 40% EtOAc in hexane. $^1$H NMR (500 MHz, DMSO-d$_6$) δ 6.67 (dd, J=5.7, 1.3 Hz, 1H), 4.81 (d, J=8.6 Hz, 1H), 4.77 (s, 2H), 4.56 (t, J=5.4 Hz, 1H), 4.04 (d, J=16.5 Hz, 1H), 3.69 (d, J=16.5 Hz, 1H), 3.57 (s, 1H), 3.17 (d, J=21.1 Hz, 1H), 2.94 (d, J=21.1 Hz, 1H), 2.16-2.06 (m, 4H), 2.00 (s, 3H), 1.91-1.86 (m, 1H), 1.77-1.66 (m, 2H), 1.38 (s, 9H). $^{13}$C NMR (125 MHz, DMSO-d$_6$) δ 6199.9, 169.5, 160.6, 153.0, 138.7, 138.1, 133.9, 130.9, 129.4, 114.6, 114.5, 79.2, 59.2, 53.9, 53.8, 53.0, 49.3, 40.7, 37.7, 36.5, 32.3, 27.5, 20.0, 19.5. HRMS (ESI-TOF) m/z: [M+Na]$^+$ Calcd for C$_{26}$H$_{29}$N$_3$O$_5$Na 486.1999; Found 486.2012. R$_f$=0.43 (50% EtOAc in hexane). Relative stereochemistry was determined based on analysis of 8.

g. (12-(TERT-BUTOXYCARBONYL)-10,10-DICYANO-2-OXO-3,4A,5,6,7,8,10,11-OCTAHYDRO-2H-5,8-EPIMINOCYCLOPENTA[B]HEPTALENE-1,4-DIYL)BIS(METHYLENE) DIACETATE (6JD).

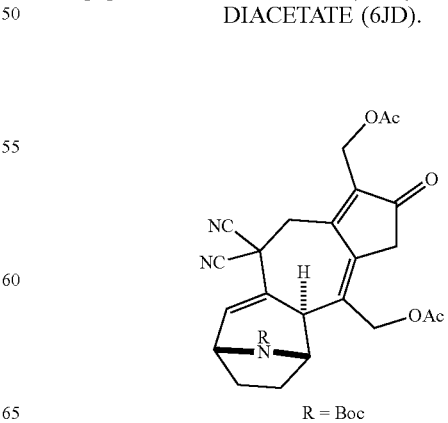

Orange solid, 59% yield via procedure 2, 56 mg (44% yield via procedure 1). Purified using 40% EtOAc in hexane. Note: Use of toluene-d$_8$ was required to obtain NMR spectra at 80° C., as DMSO-de resulting in rapid decomposition of the compound. $^1$H NMR (500 MHz, Toluene-d$_8$) δ 6.19 (d, J=5.5 Hz, 1H), 5.09 (d, J=13.1 Hz, 1H), 4.87 (d, J=7.8 Hz, 1H), 4.69 (d, J=14.0 Hz, 2H), 4.54 (d, J=13.0 Hz, 1H), 4.25 (s, 1H), 3.30-2.96 (m, 4H), 2.62 (d, J=4.6 Hz, 1H), 1.94-1.66 (m, 7H), 1.53-1.43 (m, 2H), 1.30 (d, J=4.7 Hz, 9H), 1.21 (dt, J=15.3, 8.0 Hz, 1H). $^{13}$C NMR (125 MHz, Toluene-d$_8$e) δ 198.3, 169.9, 169.6, 157.6, 154.1, 142.5, 137.7, 137.4, 135.2, 134.6, 130.4, 129.4, 129.2, 129.0, 128.8, 128.6, 128.3, 128.1, 127.9, 125.7, 125.4, 125.2, 125.0, 115.0, 114.4, 80.5, 63.9, 54.9, 54.8, 54.4, 49.7, 41.0, 39.5, 39.1, 33.4, 28.9, 28.4, 21.4, 20.9, 20.7, 20.6, 20.4, 20.3, 20.2, 20.2, 20.1, 20.0. HRMS (ESI-TOF) m/z: [M+Na]$^+$ Calcd for C$_{28}$H$_{31}$N$_3$O$_7$Na 544.2054; Found 544.2068. R$_f$=0.42 (50% EtOAc in hexane). Relative stereochemistry was determined based on analysis of 8.

h. (10,10-DICYANO-2-OXO-3,4A,5,8,10,11-HEXAHYDRO-2H-5,8-METHANOCYCLOPENTA[B]HEPTALENE-1,4-DIYL)BIS (METHYLENE) DIACETATE (6KD).

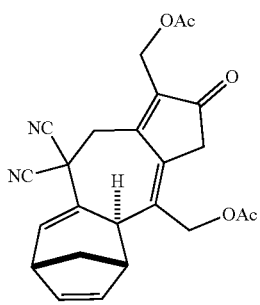

Orange solid, 50% yield, 200 mg (via procedure 2). Purified using 30% EtOAc in hexane. $^1$H NMR (500 MHz, CDCl$_3$) δ 6.89 (d, J=6.9 Hz, 1H), 6.41 (dd, J=5.5, 2.8 Hz, 1H), 5.91 (dd, J=5.5, 3.1 Hz, 1H), 4.89-4.76 (m, 4H), 3.69 (d, J=17.0 Hz, 1H), 3.49 (d, J=17.0 Hz, 1H), 3.42-3.31 (m, 2H), 3.19-3.07 (m, 2H), 2.98 (dt, J=6.7, 3.5 Hz, 1H), 2.07 (d, J=9.8 Hz, 6H), 1.91 (dt, J=9.9, 4.7 Hz, 1H), 1.57 (d, J=10.2 Hz, 1H). $^{13}$C NMR (125 MHz, CDCl$_3$) δ 199.8, 170.7, 170.5, 159.5, 142.0, 141.7, 139.0, 138.0, 134.5, 131.1, 126.9, 114.6, 113.8, 63.6, 54.7, 42.9, 41.6, 41.1, 40.0, 38.9, 38.9, 37.1, 20.8, 20.8. HRMS (ESI-TOF) m/z: [2M+Na]$^+$ Calcd for C$_{48}$H$_{44}$N$_4$O$_{10}$Na 859.2950; Found 859.2971. R$_f$=0.37 (40% EtOAc in hexane). Relative stereochemistry was determined based on analysis of 9c.

i. (9,9-DICYANO-2-OXO-2,4A,5,7,8,8A,9,10-OCTAHYDRO-3H-SPIRO[BENZO[F]AZULENE-6,2'-[1,3]DIOXOLAN]-1-YL)METHYL ACETATE (6MD).

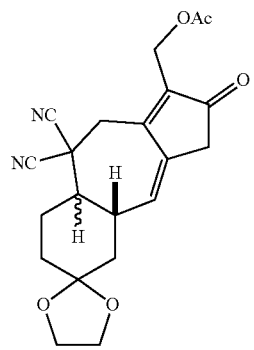

Pale yellow oil, 50% yield, 25 mg (via procedure 2). Purified using 40% EtOAc in hexane. $^1$H NMR (500 MHz, CDCl$_3$) δ 5.94-5.65 (m, 1H), 4.94-4.78 (m, 2H), 4.09-3.91 (m, 5H), 3.79-3.31 (m, 2H), 3.25-3.06 (m, 2H), 2.98-2.55 (m, 1H), 2.48-1.85 (m, 9H), 1.76-1.60 (m, 2H). $^{13}$C NMR (125 MHz, CDCl$_3$) δ 201.8, 201.4, 170.8, 170.7, 160.1, 158.7, 141.2, 140.8, 133.4, 133.3, 132.7, 132.3, 115.1, 115.0, 114.7, 112.7, 107.0, 106.9, 65.0, 64.9, 64.7, 64.5, 54.7, 54.6, 47.6, 45.8, 42.1, 42.0, 42.0, 40.8, 40.3, 39.3, 39.2, 38.0, 37.9, 34.5, 34.2, 34.0, 29.8, 22.6, 20.9, 20.8. HRMS (ESI-TOF) m/z: [M+Na]$^+$ Calcd for C$_{21}$H$_{22}$N$_2$O$_5$Na 405.1437; Found 405.1437.

10. Procedure for Diels Alder Cycloaddition of 8e: Preparation of 12-(tert-butyl) 2-methyl 6,6-dicyano-1-methylene-5,6,8,9,10,11,11a,11b-octahydro-8,11-epimino-2,4a-epoxycyclohepta[a]naphthalene-2,12(1h)-dicarboxylate (9)

8e (70 mg, 0.155 mmol) was dissolved in 1.6 mL toluene and sealed in a microwave tube. The solution was then heated to 150° C. for 9 hours using a microwave reactor. The solvent was then evaporated and the crude product was purified via column chromatography (25% EtOAc in hexane).

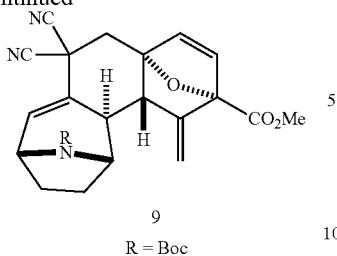

9
R = Boc

White solid, 39% yield, 27 mg. $^1$H NMR (500 MHz, DMSO-d$_6$) δ 6.62 (d, J=5.4 Hz, 2H), 6.59 (d, J=5.6 Hz, 1H), 6.28 (d, J=5.4 Hz, 1H), 5.45 (s, 1H), 5.26 (d, J=1.6 Hz, 1H), 4.68-4.61 (m, 2H), 3.85 (s, 3H), 3.24 (d, J=15.0 Hz, 1H), 2.97 (d, J=15.0 Hz, 1H), 2.32 (d, J=10.9 Hz, 1H), 2.23-2.13 (m, 2H), 1.97 (ddd, J=11.5, 8.8, 2.1 Hz, 1H), 1.80 (ddt, J=12.8, 11.5, 6.6 Hz, 1H), 1.50 (dt, J=13.3, 7.8 Hz, 1H), 1.41 (s, 9H). $^{13}$C NMR (125 MHz, DMSO-d$_6$) δ 167.2, 153.2, 148.4, 137.8, 136.7, 131.3, 127.4, 114.8, 114.4, 107.3, 90.6, 86.2, 80.1, 53.2, 52.8, 47.2, 45.9, 37.5, 37.4, 33.7, 30.9, 29.2, 28.6.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A compound, wherein the compound has a formula represented by a structure selected from:

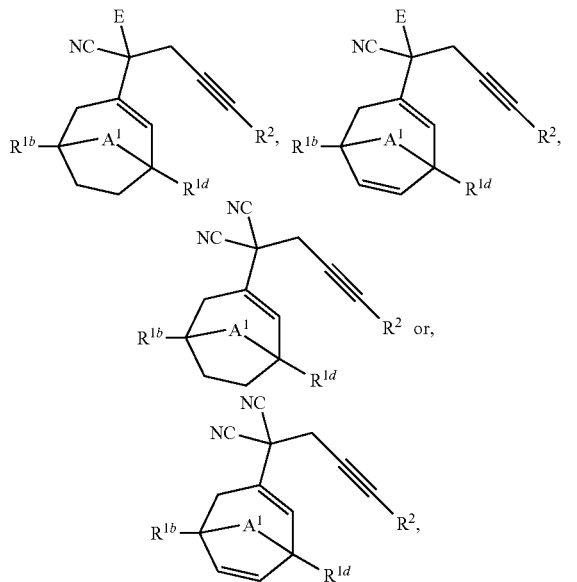

wherein E is —(C=O)OR$^{10}$, wherein R$^{10}$ is C1-C6 alkyl; wherein each of R$^{1b}$ and R$^{1d}$ is independently hydrogen, C1-C6 alkyl, aryl, or —(CH$_2$)$_m$(C=O)OR$^{11}$, wherein m is an integer selected from 0, 1, 2, and 3, and wherein R$^{11}$ is C1-C6 alkyl;

wherein R$^2$ is hydrogen, C1-C6 alkyl, aryl, or —(CH$_2$)$_n$(C=O)OR$^{12}$, wherein n is an integer selected from 0, 1, 2, and 3, and wherein R$^{12}$ is C1-C6 alkyl;

wherein A$^1$ is —C(R$^{20}$)(R$^{21}$)—, —NR$^{22}$— or —CH$_2$—, wherein R$^{20}$ is hydrogen, C1-C6 alkyl, or —(CH$_2$)$_p$(C=O)OR$^{30}$, wherein R$^{30}$ is C1-C6 alkyl; and wherein p is an integer selected from 0, 1, 2, and 3, wherein R$^{21}$ is hydrogen, C1-C6 alkyl, or —(CH$_2$)$_q$(C=O)OR$^{31}$, wherein R$^{31}$ is C1-C6 alkyl; and wherein q is an integer selected from 0, 1, 2, and 3, and wherein R$^{22}$ is C1-C6 alkyl, or —(C=O)OR$^{32}$; and wherein R$^{32}$ is C1-C6 alkyl.

2. The compound of claim 1, wherein E is —(C=O)OCH$_3$.

3. The compound of claim 1, wherein each of R$^{1b}$ and R$^{1d}$ is independently hydrogen, methyl, phenyl, or —CH$_2$(C=O)OCH$_3$.

4. The compound of claim 1, wherein R$^2$ is hydrogen, methyl, phenyl, or —CH$_2$(C=O)OCH$_3$.

5. The compound of claim 1, wherein A$^1$ is —CH$_2$— or —CHCH$_3$.

6. The compound of claim 1, wherein the compound has a formula represented by structure:

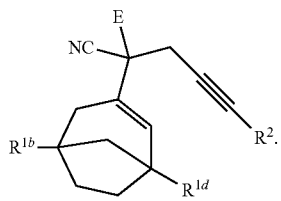

7. The compound of claim 1, wherein the compound has a formula represented by structure:

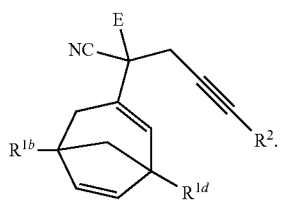

8. The compound of claim 1, wherein the compound has a formula represented by structure:

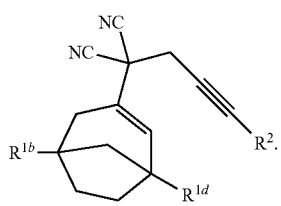

9. The compound of claim 1, wherein the compound has a formula represented by structure

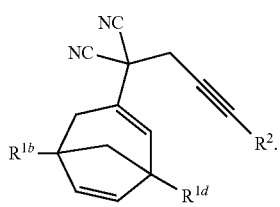

10. The compound of claim 1, wherein the compound has a formula represented by structure:

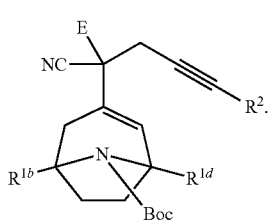

11. The compound of claim 1, wherein the compound has a formula represented by structure:

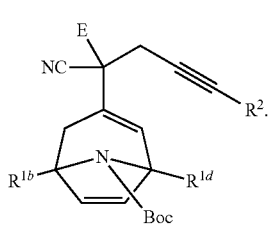

12. The compound of claim 1, wherein the compound has a formula represented by structure:

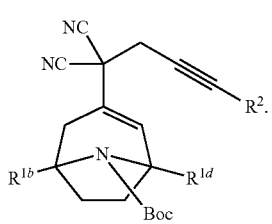

13. The compound of claim 1, wherein the compound has a formula represented by structure:

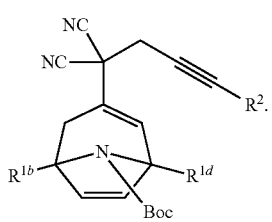

14. The compound of claim 1, wherein the compound has a formula represented by structure:

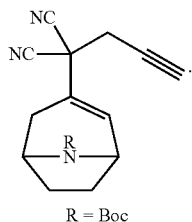

15. The compound of claim 1, wherein the compound has a formula represented by structure:

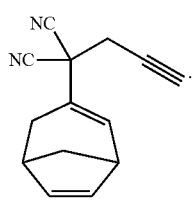 [SMILES: C#CCC(C#N)(C#N)C1=CC2C=CC(C1)C2]

16. The compound of claim 1, wherein the compound has a formula represented by structure

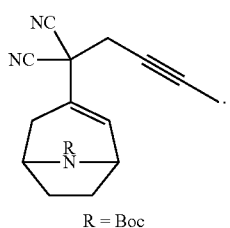

17. The compound of claim 1, wherein the compound has a formula represented by structure:

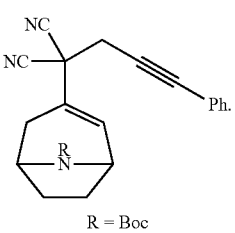

18. The compound of claim 1, wherein the compound has a formula represented by structure:

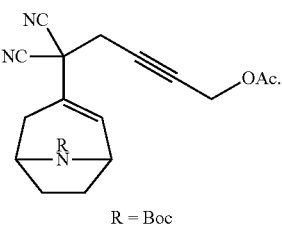

19. The compound of claim 1, wherein the compound has a formula represented by structure:

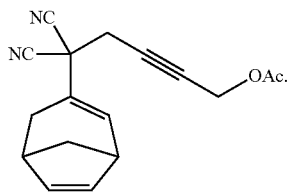 [SMILES: CC(=O)OCC#CCC(C#N)(C#N)C1=CC2C=CC(C1)C2]
* * * * *